(12) United States Patent
Uehira et al.

(10) Patent No.: US 8,293,146 B2
(45) Date of Patent: Oct. 23, 2012

(54) OPTICAL FILM AND PHASE DIFFERENCE PLATE, AND LIQUID CRYSTAL COMPOUND

(75) Inventors: Shigeki Uehira, Minami-ashigara (JP); Michitaka Matsuumi, Minami-ashigara (JP); Mamoru Sakurazawa, Minami-ashigara (JP); Masaki Okazaki, Minami-ashigara (JP); Naoyuki Nishikawa, Haibara-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 951 days.

(21) Appl. No.: 12/160,252

(22) PCT Filed: Feb. 7, 2007

(86) PCT No.: PCT/JP2007/052543
§ 371 (c)(1),
(2), (4) Date: Jul. 8, 2008

(87) PCT Pub. No.: WO2007/091716
PCT Pub. Date: Aug. 16, 2007

(65) Prior Publication Data
US 2009/0159857 A1 Jun. 25, 2009

(30) Foreign Application Priority Data

Feb. 7, 2006 (JP) ................... 2006-030004
Sep. 27, 2006 (JP) ................... 2006-263335

(51) Int. Cl.
G02F 1/335 (2006.01)
C07D 339/06 (2006.01)
C09K 19/34 (2006.01)
G02B 1/08 (2006.01)

(52) U.S. Cl. .......................... 252/585; 549/32
(58) Field of Classification Search .......... 532/1; 540/1; 548/304.4, 305.1, 561.1; 585/27; 252/585; 549/32

See application file for complete search history.

(56) References Cited

U.S. PATENT DOCUMENTS

| | | | |
|---|---|---|---|
| 3,694,211 A * | 9/1972 | Sato et al. ................ | 430/512 |
| 6,565,974 B1 | 5/2003 | Uchiyama et al. | |
| 2004/0029040 A1 | 2/2004 | Watanabe et al. | |
| 2004/0141121 A1 * | 7/2004 | Tanaka et al. ............. | 349/117 |
| 2004/0222403 A1 | 11/2004 | Sasada et al. | |
| 2008/0309860 A1 * | 12/2008 | Nimura et al. ............ | 349/117 |

FOREIGN PATENT DOCUMENTS

| | | |
|---|---|---|
| JP | 10-068816 A | 3/1998 |
| JP | 10-090521 A | 4/1998 |
| JP | 2002-156528 A | 5/2002 |
| JP | 2002-296421 A | 10/2002 |
| JP | 2004-054266 A | 2/2004 |
| JP | 2004-066585 A | 3/2004 |
| JP | 2004-231638 A | 8/2004 |
| JP | 2005-017574 A | 1/2005 |
| JP | 2005-242293 A | 9/2005 |
| JP | 2008-20896 A | 1/2008 |
| WO | WO 00/26705 A1 | 5/2000 |
| WO | WO 02/093213 A1 | 11/2002 |
| WO | WO 2005/111676 A1 * | 11/2005 |

OTHER PUBLICATIONS

Form PCT/ISA/210 (International Search Report) dated May 29, 2007.
Official Action (Notice of Reasons for Rejection) issued Apr. 10, 2012 in corresponding Japanese Application No. 2007-028239, and an English translation thereof.

* cited by examiner

*Primary Examiner* — Angela Ortiz
*Assistant Examiner* — J. L. Yang
(74) *Attorney, Agent, or Firm* — Buchanan Ingersoll & Rooney PC

(57) ABSTRACT

An optical film, which has been subjected to an orientation treatment, containing a low-molecular weight compound, in which a birefringence $\Delta n(550\,nm)$ is larger than zero (0) in an orientation direction, and the optical film satisfies the following expressions (1) and (2); and a phase difference plate, a polarizing plate and a liquid crystal display using the same:

$0.5 < \Delta n(450\,nm)/\Delta n(550\,nm) < 1.0$; and   Expression (1)

$1.05 < \Delta n(630\,nm)/\Delta n(550\,nm) < 1.5$.   Expression (2)

14 Claims, No Drawings

OPTICAL FILM AND PHASE DIFFERENCE PLATE, AND LIQUID CRYSTAL COMPOUND

TECHNICAL FIELD

The present invention relates to a novel compound which can provide a film with reverse wavelength dispersion when the compound is added to the film. Also, the present invention relates to an optical film containing such a compound. In addition, the present invention relates to a phase difference plate (retardation film) having reverse wavelength dispersion of birefringence, such as a broadband λ/4 plate. Further, the present invention relates to a polarizing plate and a liquid crystal display using the phase difference plate.

BACKGROUND ART

Phase difference plates used in liquid crystal displays have been widely used for attaining high contrast ratios and improving color shift phenomena at wide view angles in color TFT liquid crystal displays of various kinds of display modes, and the like. The types of the phase difference plates include, for example, a ¼ wavelength plate (hereinafter, abbreviated to as "λ/4 plate") that converts linearly polarized light into circularly polarized light, and a ½ wavelength plate (hereinafter, abbreviated as "λ/2 plate") that rotates the polarization vibration surface of linearly polarized light by 90°. Conventional phase difference plates are capable of adjusting monochromatic light to a phase difference of λ/4 or λ/2 with respect to light wavelength. However, the conventional phase difference plates have a problem in that white light, which is a synthesized wave and coexists with light beam in visible light region, is converted into colored polarized light due to distributions for polarization states at the respective wavelengths. This is caused by the fact that a material constituting a phase difference plate has wavelength dispersion (chromatic dispersion property) for phase difference.

For solving such a problem, various kinds of broadband phase difference plates capable of providing a uniform phase difference with respect to a wide-wavelength light have been proposed. For instance, there is disclosed a phase difference plate obtained by bonding a ¼ wavelength plate where the phase difference of birefringent light is ¼ wavelength with a ½ wavelength plate where the phase difference of birefringent light is ½ wavelength, while intersecting their optical axes (see, for example, JP-A-10-68816 ("JP-A" means unexamined published Japanese patent application)). In addition, there is disclosed a phase difference plate constructed of at least two phase difference plates having optical phase difference values of 160 to 320 nm, which are laminated at an angle that allows slow phase axes thereof to be neither parallel nor perpendicular to each other (see, for example, JP-A-10-90521).

However, for manufacturing the above phase difference plates, a complicated process is required for regulating the optical directions (optical axes and slow phase axes) of the two polymer films. The optical direction of the polymer film typically corresponds to the perpendicular or horizontal direction of a sheet or roll film. The polymer film having an optical axis or a slow phase axis in the diagonal direction of a sheet or roll is difficult to be industrially produced in large quantities. Further, it is necessary to set the optical directions of the two polymer films at an angle which does allow them to be neither parallel nor perpendicular to each other. Therefore, phase difference plates should be manufactured by carrying out the steps of obtaining chips by cutting two different polymer films at predetermined angles and then bonding the chips together, to give the phase difference plates. The steps of bonding chips and so on are complicated in operation and cause a decrease in quality due to axial displacement and a decrease in yield, while increasing costs and facilitating deterioration by contamination. In addition, it is also difficult to strictly regulate the optical phase difference values of polymer films, and the qualities thereof may tend to be decreased and so on.

For solving such a problem, there is proposed a method of manufacturing a broadband λ/4 plate with a single phase difference plate, without a lamination of phase difference plates (see, for example, WO00/26705).

The method can be preceded by mono-axial orienting using a polymer film obtained by copolymerizing a monomer unit of a polymer having positive refractive index anisotropy with a monomer unit of a polymer having a negative birefringence. Since the oriented polymer film has reverse wavelength dispersion characteristics, it is possible to prepare a broadband λ/4 plate using one phase difference film, thereby solving the above problems. However, the obtained phase difference values are within a narrow range, so many films should be laminated otherwise the sufficient optical characteristics cannot be obtained. As a result, a polarizing plate to be prepared is made thick and heavy. In addition, in the step of laminating films, there are needs of preventing the optical axes from being displaced, preventing exogenous materials from contamination, and the like. Further, there is also a problem that the producing method is complicated.

Further, in JP-A-2005-242293, a reverse dispersion wavelength film is formed by applying a polymerizable liquid crystal compound onto the upper layer of a cellulose acylate film, drying and polymerizing the compound, peeling a hardened film thus obtained, and stretching only the cellulose acylate film by 20% at 150° C. However, the method also has a problem that this manufacturing process is complicated.

DISCLOSURE OF INVENTION

It is a subject of the present invention to provide a novel compound, and a phase difference plate having reverse wavelength dispersion of birefringence, such as a broadband λ/4 plate, which can be produced using the compound by a simple production process. In addition, another subject of the present invention is to provide a liquid crystal composition, a phase difference plate, and an elliptical polarizing plate, using such a novel compound.

The inventors of the present invention have intensively studied and investigated for solving the aforesaid problems. As a result, the inventors of the present invention have found that the wavelength dispersion of a film can be converted into reverse dispersion by only adding a given material to a given film and stretching (orienting) the given film, and have finally completed the present invention.

According to the present invention, there is provided the following means:
(1) An optical film, which has been subjected to an orientation treatment, comprising at least one low-molecular weight compound,
wherein a birefringence $\alpha n(550 \text{ nm})$ is larger than zero (0) in an orientation direction, and
wherein the optical film satisfies the following expressions (1) and (2):

$$0.5 < \Delta n(450 \text{ nm})/\Delta n(550 \text{ nm}) < 1.0; \text{ and} \qquad \text{Expression (1)}$$

$$1.05 < \Delta n(630 \text{ nm})/\Delta n(550 \text{ nm}) < 1.5; \qquad \text{Expression (2)}$$

(2) The optical film according to the above item (1), wherein the low-molecular weight compound has a molecular weight of 100 to 1,500;
(3) The optical film according to the above item (1) or (2), wherein the low-molecular weight compound is contained in an amount of 0.1 to 50 mass % with respect to the mass of the film;
(4) The optical film according to any one of the above items (1) to (3), wherein the optical film satisfies the following expressions (1') and (2'):

$$0.7 < \Delta n(450 \text{ nm})/\Delta n(550 \text{ nm}) < 0.9; \text{ and} \qquad \text{Expression (1')}$$

$$1.05 < \Delta n(630 \text{ nm})/\Delta n(550 \text{ nm}) < 1.25; \qquad \text{Expression (2')}$$

(5) The optical film according to any one of the above items (1) to (4), wherein the low-molecular weight compound is a compound represented by formula (I):

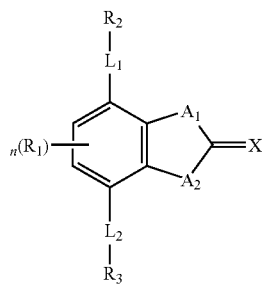

Formula (I)

wherein $L_1$ and $L_2$ each independently represent a single bond or a divalent linking group; $A_1$ and $A_2$ each independently represent a group selected from the group consisting of —O—, —NR— (in which R represents a hydrogen atom or a substituent), —S—, and —CO—; $R_1$, $R_2$ and $R_3$ each independently represent a substituent; X represents a nonmetallic atom belonging to any of Groups 14 to 16, and may have a hydrogen atom or a substituent; and n represents an integer of 0 to 2;
(6) The optical film according to any one of the above items (1) to (5), wherein the low-molecular weight compound is a compound represented by formula (II):

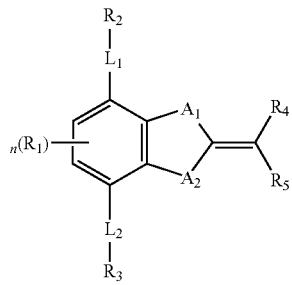

Formula (II)

wherein $L_1$ and $L_2$ each independently represent a single bond or a divalent linking group; $A_1$ and $A_2$ each independently represent a group selected from the group consisting of —O—, —NR— (in which R represents a hydrogen atom or a substituent), —S—, and —CO—; $R_1$, $R_2$, $R_3$, $R_4$ and $R_5$ each independently represent a substituent; and n represents an integer of 0 to 2;
(7) The optical film according to the above item (5) or (6), wherein the compound represented by formula (I) or (II) is a compound showing liquid crystallinity;
(8) The optical film according to any one of the above items (5) to (7), wherein $R_2$ and $R_3$ each independently represent a benzene ring having a substituted or unsubstituted benzoyloxy group at the 4-position, a benzene ring having a substituted or unsubstituted cyclohexyl group at the 4-position, a cyclohexane ring having a substituted or unsubstituted benzene ring at the 4-position, or a cyclohexane ring having a substituted or unsubstituted cyclohexyl group at the 4-position;
(9) The optical film according to any one of the above items (1) to (8), which is formed of a polymer composition comprising a cellulose compound as a main component;
(10) The optical film according to the above item (9), wherein the cellulose compound is a cellulose acylate;
(11) A phase difference plate, comprising the optical film according to any one of the above items (1) to (10);
(12) A polarizing plate, comprising the phase difference plate according to the above item (11);
(13) A liquid crystal display, comprising the phase difference plate according to the above item (11) or the polarizing plate according to the above item (12);
(14) A compound represented by formula (II):

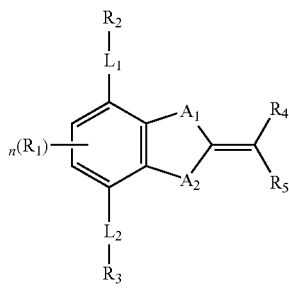

Formula (II)

wherein $L_1$ and $L_2$ each independently represent a single bond or a divalent linking group; $A_1$ and $A_2$ each independently represent a group selected from the group consisting of —O—, —NR— (in which R represents a hydrogen atom or a substituent), —S—, and —CO—; $R_1$, $R_2$, $R_3$, $R_4$ and $R_5$ each independently represent a substituent; and n represents an integer of 0 to 2;
(15) The compound according to the above item (14), which shows liquid crystallinity;
(16) The compound according to the above item (14) or (15), wherein R2 and R3 each independently represent a benzene ring having a substituted or unsubstituted benzoyloxy group at the 4-position, a benzene ring having a substituted or unsubstituted cyclohexyl group at the 4-position, a cyclohexane ring having a substituted or unsubstituted benzene ring at the 4-position, or a cyclohexane ring having a substituted or unsubstituted cyclohexyl group at the 4-position; and
(17) A liquid crystal composition, comprising the compound according to any one of the above items (14) to (16).

Please note that in the above items, Δn(450 mm), Δn(550 nm) and Δn(630 nm) each means birefringent of the film at a wavelength of 450 nm, 550 nm and 630 nm, respectively.

Other and further features and advantages of the invention will appear more fully from the following description.

BEST MODE FOR CARRYING OUT THE INVENTION

Hereinafter, the present invention will be described in detail. The constitutional requirements described below may be embodied on the basis of the representative embodiments of the present invention. However the present invention is not limited to such embodiments.

In the present specification, "to" denotes a range including numerical values described before and after it as a minimum value and a maximum value.

[Low-Molecular Weight Compound]

In a film prepared by subjecting a polymer composition to an orientation treatment such as stretching, for realizing the wavelength dispersion of birefringence $\Delta n$ where the birefringence $\Delta n(550\ nm)$ is a positive value with respect to the orientation direction and the birefringence $\Delta n$ at given wavelengths satisfies the following equations (1) and (2), it is necessary to appropriately adjust the direction of a transition moment and absorption wavelengths in the orientation direction (hereinafter, referred to as TD direction) and the direction perpendicular to the TD direction (hereinafter, referred to as MD direction).

$$0.5 < \Delta n(450\ nm)/\Delta n(550\ nm) < 1.0 \qquad \text{Equation (1)}$$

$$1.05 < \Delta n(630\ nm)/\Delta n(550\ nm) < 1.5 \qquad \text{Equation (2)}$$

Here, $\Delta n(450\ nm)$, $\Delta n(550\ nm)$ and $\Delta n(630\ nm)$ are also referred to as blue light (450 nm), green light (550 nm), and red light (630 nm), respectively. It is necessary to adjust retardation to the optimum at each wavelength for improving view angle characteristics. In the present invention, when positive birefringence is applied to the most important green (550 nm), the preferable ranges of the blue (450 nm) and red (630 nm) are within the ranges of the expressions (1) and (2). If the value of $\Delta n(450\ nm)/\Delta n(550\ nm)$ is too small, the retardation of the optimal blue light becomes too large with respect to the optimal green light, resulting in poor view angle characteristics. On the other hand, if it is too large, the retardation of the optimal blue light becomes too small with respect to the optimal green light, resulting in poor view angle characteristics. In addition, if the value of $\Delta n(630\ nm)/\Delta n(550\ nm)$ is too small, the retardation of the optimal red light becomes too small with respect to the optimal green light, resulting in poor view angle characteristics. On the other hand, if it is too large, the retardation of the optimal red light becomes too large with respect to the optimal green light, resulting in poor view angle characteristics. Further, it is preferable that the values of $\Delta n(450\ nm)/\Delta n(550\ nm)$ and $\Delta n(630\ nm)/\Delta n(550\ nm)$ be within the ranges defined by the expressions (1') and (2').

$$0.7 < \Delta n(450\ nm)/\Delta n(550\ nm) < 0.9 \qquad \text{Expression (1')}$$

$$1.05 < \Delta n(630\ nm)/\Delta n(550\ nm) < 1.25 \qquad \text{Expression (2')}$$

$\Delta n$ is a value obtained by subtracting the refractive index in the MD direction from the refractive index in the TD direction. Thus, in the present invention, when the wavelength dispersion of the refractive index in the MD direction tends downward compared with one in the TD direction (the slope of $\Delta n$ when smaller wavelengths are on the left side and larger wavelengths are on the right side), the subtracted value satisfies the following expressions (3) and (4).

$$1 > |\Delta n(450\ nm)/\Delta n(550\ nm)| \qquad \text{Expression (3)}$$

$$1 < |\Delta n(630\ nm)/\Delta n(550\ nm)| \qquad \text{Expression (4)}$$

The wavelength dispersion of the refractive index is, as represented by the Lorentz-Lorenz expression, closely related to the absorption of a substance. Thus, for allowing the wavelength dispersion in the MD direction to tend downward, when the absorption transition wavelength in the MD direction is shifted to a longer wavelength region than one in the TD direction, a film satisfying the expressions (3) and (4) can be designed. For instance, in a polymer material subjected to a stretching treatment, the MD direction thereof is perpendicular to a molecular chain. Shifting the absorption transition wavelength in the wide direction of the polymer to a longer wavelength region is very difficult for the polymer material.

According to the present invention, by adding a low-molecular weight compound to a polymer material and orientating the polymer material, a film satisfying the expressions (3) and (4) can be designed as far as the absorption transition wavelength of the low-molecular weight compound is in the longer wavelength region in the polymer wide direction (MD direction).

When the refractive index of the low-molecular weight compound in the TD direction is larger than one in the MD direction, there is no problem in that the birefringence $\Delta n(550\ nm)$ of the film to the TD direction is positive. Meanwhile, when the refractive index of the low-molecular weight compound in the MD direction is larger than one in the TD direction, there is no problem as far as the refractive index of the polymer material is large in the TD direction and the birefringence $\Delta n(550\ nm)$ of the film is positive.

Birefringence ($\Delta n$) is described in detail in, for example, "Ekisho Binran (Handbook of Liquid crystal), p. 201, 2000 (published by MARUZEN Co., Ltd.). Birefringence $\Delta n$ is generally dependent on temperature. The $\Delta n$ values defined in the present invention may be measured at any temperature, but the $\Delta n$ values of the optical film of the present invention are measured at a temperature of preferably −20 to 120° C.

The molecular weight of the low-molecular weight compound to be used in the present invention is preferably 100 to 1,500.

In the present invention, the above low-molecular weight compound is preferably a compound represented by formula (I), more preferably a compound represented by formula (II).

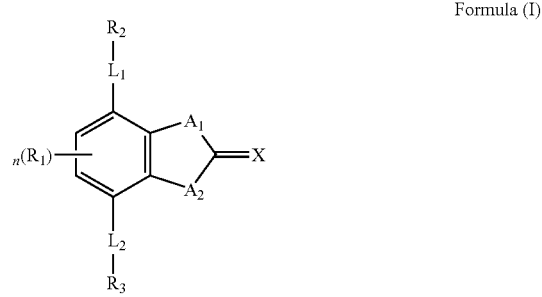

Formula (I)

In formula (I), $L_1$ and $L_2$ each independently represent a single bond or a divalent linking group; $A_1$ and $A_2$ each independently represent a group selected from the group consisting of —O—, —NR— (in which R represents a hydrogen atom or a substituent), —S—, and —CO—; $R_1$, $R_2$ and $R_3$ each independently represent a substituent; X represents a nonmetallic atom belonging to any of Groups 14 to 16, and may have a hydrogen atom or a substituent; and n represents an integer of 0 to 2.

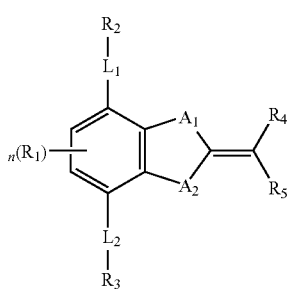

Formula (II)

In formula (II), $L_1$ and $L_2$ each independently represent a single bond or a divalent linking group; $A_1$ and $A_2$ each independently represent a group selected from the group consisting of —O—, —NR— (in which R represents a hydrogen atom or a substituent), —S—, and —CO—; $R_1$, $R_2$, $R_3$, $R_4$ and $R_5$ each independently represent a substituent; and n represents an integer of 0 to 2.

In formulas (I) or (II), preferable examples of the divalent linking group represented by $L_1$ and $L_2$ include the following groups.

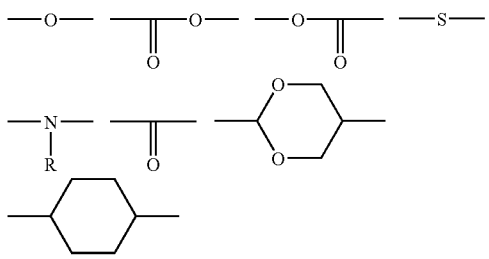

More preferable examples include —O—, —COO—, and —OCO—.

In formulas (I) and (II), $R_1$ is a substituent. When there are two or more $R_1$'s, they may be the same or different, or may form a ring. Specific examples of the substituent include a halogen atom (e.g., a fluorine atom, a chlorine atom, a bromine atom, an iodine atom), an alkyl group (preferably an alkyl group having 1 to 30 carbon atoms, e.g., a methyl group, an ethyl group, a n-propyl group, an isopropyl group, a t-butyl group, a n-octyl group, a 2-ethylhexyl group), a cycloalkyl group (preferably a substituted or unsubstituted cycloalkyl group having 3 to 30 carbon atoms, e.g., a cyclohexyl group, a cyclopentyl group, a 4-n-dodecylcyclohexyl group), a bicycloalkyl group (preferably a substituted or unsubstituted bicycloalkyl group having 5 to 30 carbon atoms, that is, a monovalent group obtained by removing one hydrogen atom from a bicycloalkane having 5 to 30 carbon atoms, e.g., a bicyclo[1,2,2]heptane-2-yl group, a bicyclo[2,2,2]octane-3-yl group), an alkenyl group (preferably a substituted or unsubstituted alkenyl group having 2 to 30 carbon atoms, e.g., a vinyl group, an allyl group), a cycloalkenyl group (preferably a substituted or unsubstituted cycloalkenyl group having 3 to 30 carbon atoms, that is, a monovalent group obtained by removing one hydrogen atom from a cycloalkene having 3 to 30 carbon atoms, e.g., a 2-cyclopentene-1-yl group, a 2-cyclohexene-1-yl group), a bicycloalkenyl group (a substituted or unsubstituted bicycloalkenyl group, preferably a substituted or unsubstituted bicycloalkenyl group having 5 to 30 carbon atoms, that is, a monovalent group obtained by removing one hydrogen atom from a bicycloalkene having one double bond, e.g., a bicyclo[2,2,1]hepto-2-ene-1-yl group, a bicyclo[2,2,2]octo-2-ene-4-yl group), an alkynyl group (preferably a substituted or unsubstituted alkynyl group having 2 to 30 carbon atoms, e.g., an ethynyl group, a propargyl group), an aryl group (preferably a substituted or unsubstituted aryl group having 6 to 30 carbon atoms, e.g., a phenyl group, a p-tolyl group, a naphthyl group), a heterocyclic group (preferably a 5- or 6-membered substituted or unsubstituted heterocyclic group, that is a monovalent group obtained by removing one hydrogen atom from an aromatic or non-aromatic heterocyclic compound, more preferably a 5- or 6-membered aromatic heterocyclic group having 3 to 30 carbon atoms, e.g., a 2-furyl group, a 2-thienyl group, a 2-pyrimidinyl group, a 2-benzothiazolyl group), a cyano group, a hydroxyl group, a nitro group, a carboxyl group, an alkoxy group (preferably a substituted or unsubstituted alkoxy group having 1 to 30 carbon atoms, e.g., a methoxy group, an ethoxy group, an isopropoxy group, a t-butoxy group, a n-octyloxy group, a 2-methoxyethoxy group), an aryloxy group (preferably a substituted or unsubstituted aryloxy group having 6 to 30 carbon atoms, e.g., a phenoxy group, a 2-methylphenoxy group, a 4-tert-butylphenoxy group, a 3-nitrophenoxy group, a 2-tetradecanoylaminophenoxy group), a silyloxy group (preferably a silyloxy group having 3 to 20 carbon atoms, e.g., a trimethylsilyloxy group, a tert-butyldimethylsilyloxy group), a heterocyclic oxy group (preferably a substituted or unsubstituted heterocyclic oxy group having 2 to 30 carbon atoms, e.g., a 1-phenyltetrazole-5-oxy group, a 2-tetrahydropyranyloxy group), an acyloxy group (preferably a formyloxy group, a substituted or unsubstituted alkylcarbonyloxy group having 2 to 30 carbon atoms, and a substituted or unsubstituted arylcarbonyloxy group having 6 to 30 carbon atoms, e.g., a formyloxy group, an acetyloxy group, a pivaloyloxy group, a stealoyloxy group, a benzoyloxy group, a p-methoxyphenylcarbonyloxy group), a carbamoyloxy group (preferably a substituted or unsubstituted carbamoyloxy group having 1 to 30 carbon atoms, e.g., an N,N-dimethylcarbamoyloxy group, an N,N-diethylcarbamoyloxy group, a morpholinocarbonyloxy group, an N,N-di-n-octylaminocarbonyloxy group, an N-n-octylcarbamoyloxy group), an alkoxycarbonyloxy group (preferably a substituted or unsubstituted alkoxycarbonyloxy group having 2 to 30 carbon atoms, e.g., a methoxycarbonyloxy group, an ethoxycarbonyloxy group, a tert-butoxycarbonyloxy group, a n-octylcarbonyloxy group), an aryloxycarbonyloxy group (preferably a substituted or unsubstituted aryloxycarbonyloxy group having 7 to 30 carbon atoms, e.g., a phenoxycarbonyloxy group, a p-methoxyphenoxycarbonyloxy group, a p-n-hexadecyloxyphenoxycarbonyloxy group), an amino group (preferably an amino group, a substituted or unsubstituted alkylamino group having 1 to 30 carbon atoms, and a substituted or unsubstituted anilino group having 6 to 30 carbon atoms, e.g., an amino group, a methylamino group, a dimethylamino group, an anilino group, an N-methyl-anilino group, a diphenylamino group), an acylamino group (preferably a formylamino group, a substituted or unsubstituted alkylcarbonylamino group having 1 to 30 carbon atoms, and a substituted or unsubstituted arylcarbonylamino group having 6 to 30 carbon atoms, e.g., a formylamino group, an acetylamino group, a pivaloylamino group, a lauroylamino group, a benzoylamino group), an aminocarbonylamino group (preferably a substituted or unsubstituted aminocarbonylamino group having 1 to 30 carbon atoms, e.g., a carbamoylamino group, an N,N-dimethylaminocarbonylamino group, an N,N-diethylaminocarbonylamino group, a morpholinocarbonylamino group), an alkoxycarbonylamino group (preferably a substituted or unsubstituted alkoxycarbonylamino group having 2 to 30 carbon atoms, e.g., a methoxycarbonylamino group, an ethoxycarbonylamino group, a tert-butoxycarbonylamino group, a n-octadecyloxycarbonylamino group, an N-methyl methoxycarbonylamino group), an aryloxycarbonylamino group (preferably a substituted or unsubstituted aryloxycarbonylamino group having 7 to 30 carbon atoms, e.g., a phenoxycarbonylamino group, a p-chlorophenoxycarbonylamino group, a m-n-octyloxyphenoxycarbonylamino group), a sulfamoyl amino group (preferably a substituted or unsubstituted sulfamoylamino group having 0 (zero) to 30 carbon atoms, e.g., a sulfamoylamino group, an N,N-dimethylaminosulfonylamino group, an N-n-octylaminosulfonylamino group), an alkyl- or aryl-sulfonylamino group (preferably a substituted or unsubstituted alkylsulfonylamino group having 1 to 30 carbon atoms, a substituted or unsubstituted arylsulfonylamino group having 6 to 30 carbon atoms, e.g., a methylsulfonylamino group, a butylsulfonylamino group, a phenylsulfonylamino group, a 2,3,5-trichlorophenylsulfonylamino group, a p-methylphenylsulfonylamino group), a mercapto group, an alkylthio group (preferably a substituted or unsubstituted alkylthio group having 1 to 30 carbon atoms, e.g., a methylthio group, an ethylthio group, a n-hexadecylthio group), an arylthio group (preferably a substituted or unsubstituted arylthio group having 6 to 30 carbon atoms, e.g., a phenylthio group, a p-chlorophenylthio group, a m-methoxyphenylthio group), a heterocyclic thio group (preferably a substituted or unsubstituted heterocyclic thio group having 2 to 30 carbon atoms, e.g., a 2-benzothiazolylthio group, a 1-phenyltetrazol-5-yl thio group), a sulfamoyl group (preferably a substituted or unsubstituted sulfamoyl group having 0 (zero) to 30 carbon atoms, e.g., an N-ethylsulfamoyl group, an N-(3-dodecyloxypropyl)sulfamoyl group, an N,N-dimethylsulfamoyl group, an N-acetylsulfamoyl group, an N-benzoylsulfamoyl group, an N—(N'-phenylcarbamoyl)sulfamoyl group), a sulfo group, an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g., a methylsulfinyl group, an ethylsulfinyl group, a phenylsulfinyl group, a p-methylphenylsulfinyl group), an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g., a methylsulfonyl group, an ethylsulfonyl group, a phenylsulfonyl group, a p-methylphenylsulfonyl group), an acyl group (preferably a formyl group, a substituted or unsubstituted alkylcarbonyl group having 2 to 30 carbon atoms, or a substituted or unsubstituted arylcarbonyl group having 7 to 30 carbon atoms, e.g., an acetyl group, a pivaloylbenzoyl group), an aryloxycarbonyl group (preferably a substituted or unsubstituted aryloxycarbonyl group having 7 to 30 carbon atoms, e.g., a phenoxycarbonyl group, an o-chlorophenoxycarbonyl group, a m-nitrophenoxycarbonyl group, a p-tert-butylphenoxycarbonyl group), an alkoxycarbonyl group (preferably a substituted or unsubstituted alkoxycarbonyl group having 2 to 30 carbon atoms, e.g., a methoxycarbonyl group, an ethoxycarbonyl group, a tert-butoxycarbonyl group, a n-octadecyloxycarbonyl group), a carbamoyl group (preferably a substituted or unsubstituted carbamoyl group having 1 to 30 carbon atoms, e.g., a carbamoyl group, an N-methylcarbamoyl group, an N,N-dimethylcarbamoyl group, an N,N-di-n-octylcarbamoyl group, an N-(methylsulfonyl)carbamoyl group), an aryl- or heterocyclic-azo group (preferably a substituted or unsubstituted arylazo group having 6 to 30 carbon atoms or a substituted or unsubstituted heterocyclic azo group having 3 to 30 carbon atoms, e.g., a phenylazo group, a p-chlorophenylazo group, a 5-ethylthio-1,3,4-thiadiazole-2-yl azo group), an imido group (preferably an N-succinimido group, an N-phthalimido group), a phosphino group (preferably a substituted or unsubstituted phosphino group having 2 to 30 carbon atoms, e.g., a dimethylphosphino group, a diphenylphosphino group, a methylphenoxyphosphino group), a phosphinyl group (preferably a substituted or unsubstituted phosphinyl group having 2 to 30 carbon atoms, e.g., a phosphinyl group, a dioctyloxyphosphinyl group, a diethoxyphosphinyl group), a phosphinyloxy group (preferably a substituted or unsubstituted phosphinyloxy group having 2 to 30 carbon atoms, e.g., a diphenoxyphosphinyloxy group, a dioctyloxyphosphinyloxy group), a phosphinylamino group (preferably a substituted or unsubstituted phosphinylamino group having 2 to 30 carbon atoms, e.g., a dimethoxyphosphinylamino group, a dimethylaminophosphinylamino group), and a silyl group (preferably a substituted or unsubstituted silyl group having 3 to 30 carbon atoms, e.g., a trimethylsilyl group, a tert-butyldimethylsilyl group, a phenyldimethylsilyl group).

Of the above-mentioned substituents, those substituents which have hydrogen atom(s) may be further substituted with the above groups in place of the hydrogen atom(s). Examples of such functional groups include an alkylcarbonylaminosulfonyl group, an arylcarbonylaminosulfonyl group, an alkylsulfonylaminocarbonyl group, and an arylsulfonylaminocarbonyl group. Examples thereof include methylsulfonylaminocarbonyl, p-methylphenylsulfonylaminocarbonyl, acetylaminosulfonyl, and benzoylaminosulfonyl.

$R^1$ is preferably a halogen atom, an alkyl group, an alkenyl group, an aryl group, a heterocyclic group, a hydroxyl group, a carboxyl group, an alkoxy group, an aryloxy group, an acyloxy group, a cyano group or amino group; and more preferably a halogen atom, an alkyl group, a cyano group or an alkoxy group.

$R_2$ and $R_3$ each independently represent a substituent. Examples thereof include those of $R_1$ described above. For obtaining the effects of the present invention, the low-molecular weight compound for use in the present invention used for an optical film is preferably oriented with a higher degree of ordered orientation. When the low-molecular weight compound for use in the present invention is the compound represented by formula (I) or (II), $R_2$ and $R_3$ exert larger influences on the order of orientation. For raising the degree of ordered orientation, the compound represented by formula (I) or (II) preferably shows liquid crystallinity. Further, from a view point of raising the degree of ordered orientation, preferably, $R_2$ and $R_3$ each independently represent a substituted or unsubstituted benzene ring or a substituted or unsubstituted cyclohexane ring. $R_2$ and $R_3$ each more preferably represent a benzene ring having a substituent or a cyclohexane ring having a substituent, further preferably a benzene ring having a substituent at the 4-position or a cyclohexane ring having a substituent at the 4-position, still more preferably a benzene ring having a substituted or unsubstituted benzoyloxy group at the 4-position, a benzene ring having a substituted or unsubstituted cyclohexyl group at the 4-position, a cyclohexane ring having a substituted or unsubstituted benzene ring at the 4-position, or a cyclohexane ring having a substituted or unsubstituted cyclohexane at the 4-position. Among them, preferable is a cyclohexane ring having a substituted or unsubstituted cyclohexyl group at the 4-position. Further, more preferable is a benzene ring having, at the 4-position, a benzoyloxy group having a substituent at the 4-position; a benzene ring having, at the 4-position, a cyclohexyl group having a substituent at the 4-position; a cyclohexane ring having, at the 4-position, a benzene ring having a substituent at the 4-position; or a cyclohexane group having, at the 4-position, a cyclohexyl group having a substituent at the 4-position. Most preferable is a cyclohexane ring having, at the 4-position, a cyclohexyl group having a substituent at the 4-position. The substituent of the cyclohexyl group having a substituent at the 4-position is preferably, but not particularly limited to, an alkyl group.

In addition, even though there are stereoisomeric forms, cis- and trans-forms, for the cyclohexane ring having a substituent at the 4-position, the present invention is not limited to any of them and a mixture of them may be also available. However, the trans-cyclohexane ring is preferable.

$R_4$ and $R_5$ each independently represent a substituent. Examples thereof include those of $R_1$ described above. The substituent is preferably an electron-withdrawing substituent having a Hammett substituent constant $\sigma_p$ value of more than zero (0), and it more preferably has an electron-withdrawing substituent having an $\sigma_p$ value of 0 to 1.5. Examples of such a substituent include a trifluoromethyl group, a cyano group, a carbonyl group and a nitro group. $R_4$ and $R_5$ may be bonded together to form a ring.

Herein, Hammett's substituent constants $\sigma_p$ and $\sigma_m$ are described in detail in such books as "Hammett Soku—Kozo to Hannousei—," written by Naoki Inamoto (Maruzen); "Shin-jikken Kagaku-koza 14/Yukikagoubutsu no Gosei to Hanno V," page 2605 (edited by Nihonkagakukai, Maruzen); "Riron Yukikagaku Kaisetsu," written by Tadao Nakaya, page 217 (Tokyo Kagakudojin); and "Chemical Review" (Vol. 91), pages 165 to 195 (1991).

$A_1$ and $A_2$ each independently represent a group selected from the group consisting of —O—, —NR— (in which R is a hydrogen atom or a substituent), —S—, and —CO—. Preferably, they are —O—, —NR— (in which R represents a substituent, for example, any of those exemplified for $R_1$ described above), or —S—.

X represents a nonmetal atom of any of Groups 14 to 16 in the periodic table of elements. X may have a hydrogen atom or a substituent. X is preferably =O, =S, =NR', or =C(R')R' (in which R' represents a substituent, for example, any of those exemplified for $R_1$).

n represents an integer of 0 to 2, preferably 0 or 1.

Specific examples of the compound represented by formula (I) or (II) are shown below, but the invention is not meant to be limited to those. In the following description, when the exemplified compounds shown below are referred to, a number X put in parentheses, that is, (X) attached to the exemplified compound is used to express the compound as "exemplified compound (X)", unless otherwise specified.

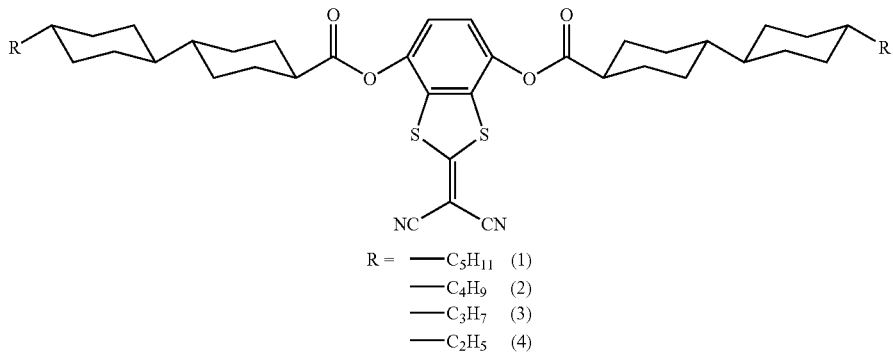

R = —$C_5H_{11}$ (1)
—$C_4H_9$ (2)
—$C_3H_7$ (3)
—$C_2H_5$ (4)

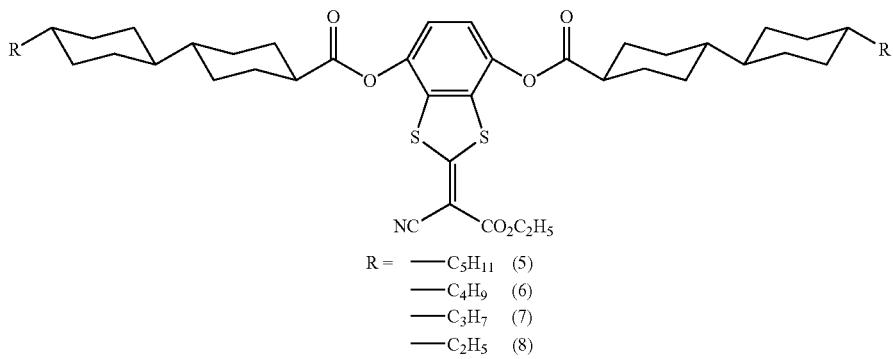

R = —$C_5H_{11}$ (5)
—$C_4H_9$ (6)
—$C_3H_7$ (7)
—$C_2H_5$ (8)

-continued
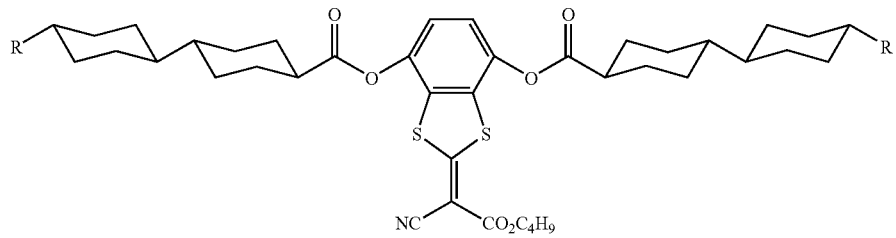
R = —C$_5$H$_{11}$ (9)
—C$_4$H$_9$ (10)
—C$_3$H$_7$ (11)
—C$_2$H$_5$ (12)
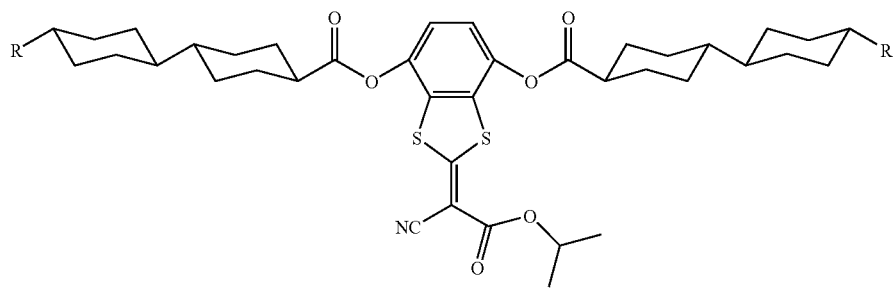
R = —C$_5$H$_{11}$ (13)
—C$_4$H$_9$ (14)
—C$_3$H$_7$ (15)
—C$_2$H$_5$ (16)
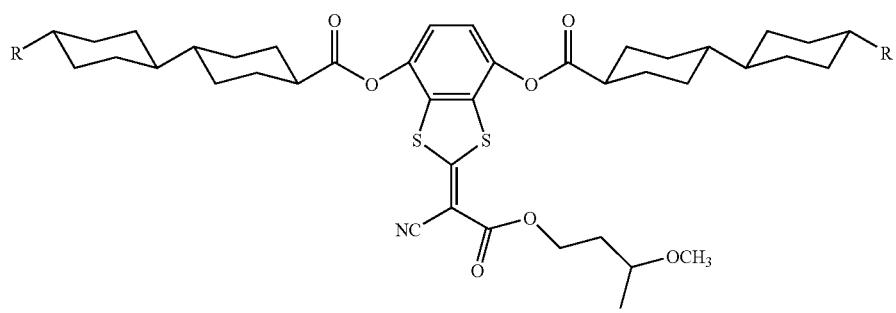
R = —C$_5$H$_{11}$ (17)
—C$_4$H$_9$ (18)
—C$_3$H$_7$ (19)
—C$_2$H$_5$ (20)
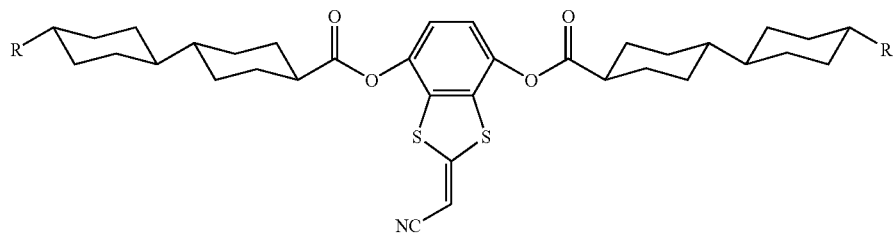
R = —C$_5$H$_{11}$ (21)
—C$_4$H$_9$ (22)
—C$_3$H$_7$ (23)
—C$_2$H$_5$ (24)

-continued
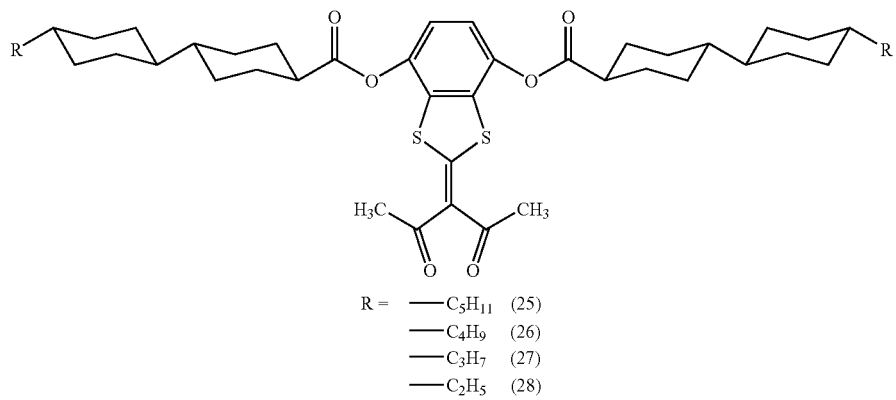
R = —C₅H₁₁ (25)
—C₄H₉ (26)
—C₃H₇ (27)
—C₂H₅ (28)
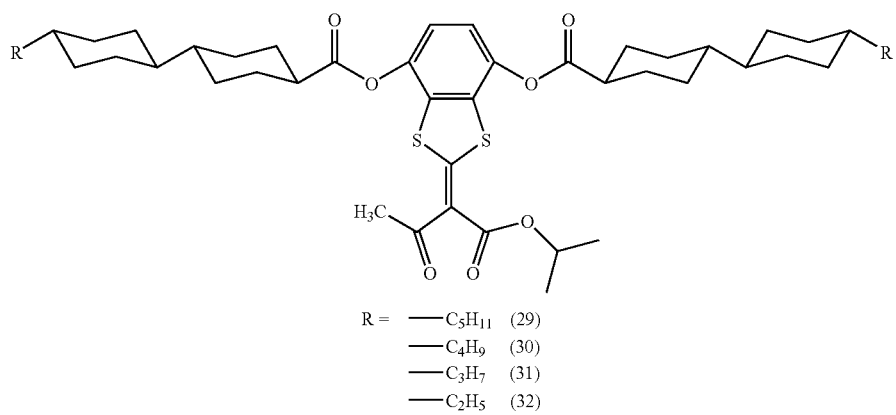
R = —C₅H₁₁ (29)
—C₄H₉ (30)
—C₃H₇ (31)
—C₂H₅ (32)
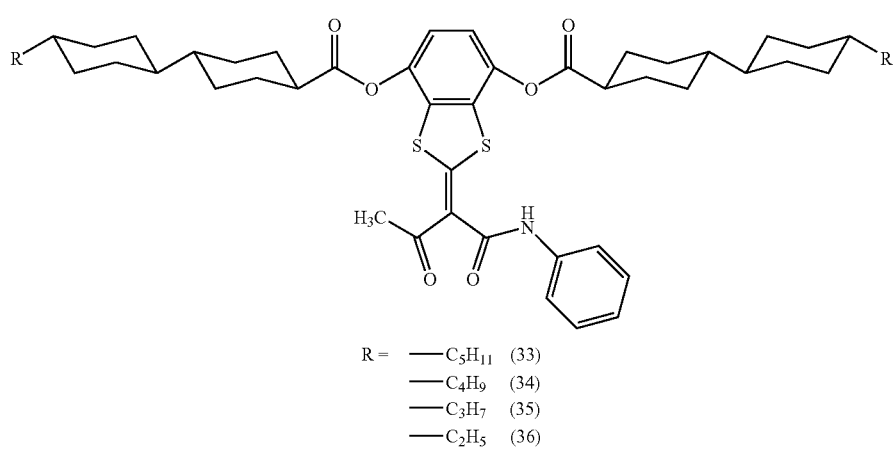
R = —C₅H₁₁ (33)
—C₄H₉ (34)
—C₃H₇ (35)
—C₂H₅ (36)
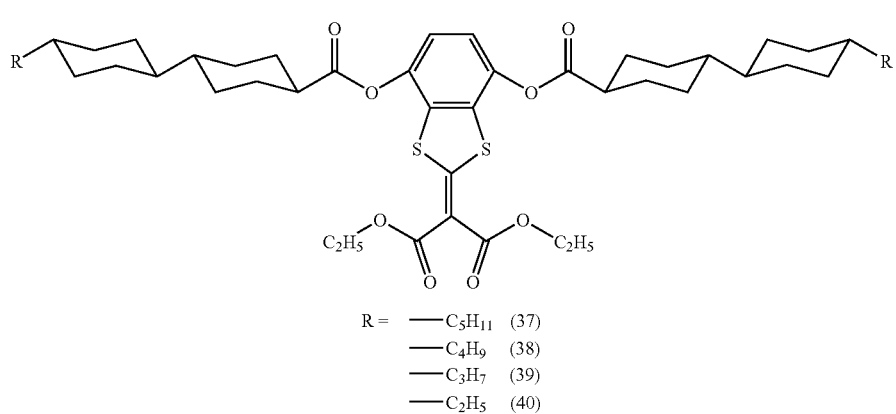
R = —C₅H₁₁ (37)
—C₄H₉ (38)
—C₃H₇ (39)
—C₂H₅ (40)

-continued
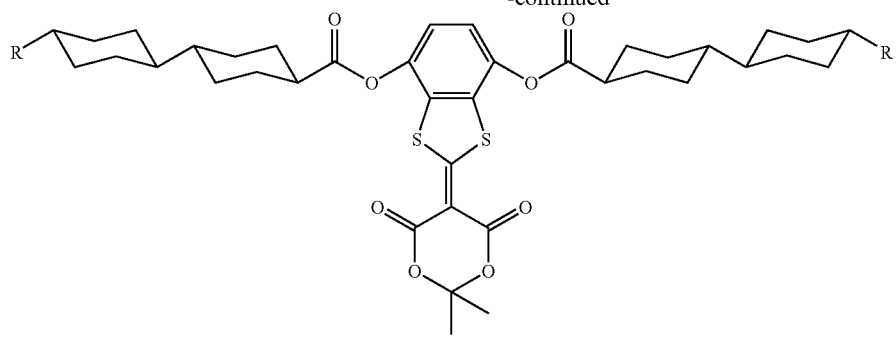
R = —C$_5$H$_{11}$ (41)
—C$_4$H$_9$ (42)
—C$_3$H$_7$ (43)
—C$_2$H$_5$ (44)
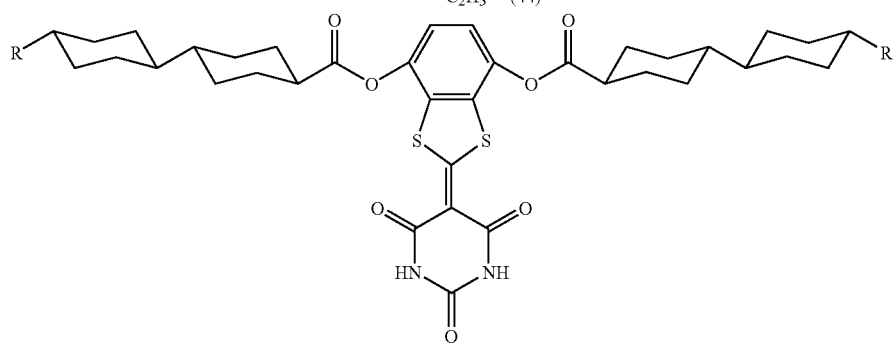
R = —C$_5$H$_{11}$ (45)
—C$_4$H$_9$ (46)
—C$_3$H$_7$ (47)
—C$_2$H$_5$ (48)
(49)
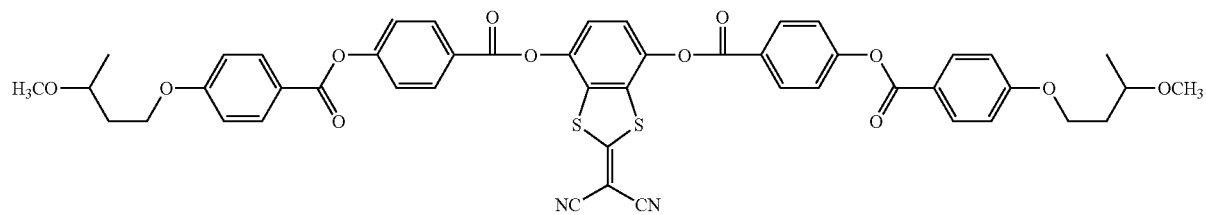
(50)
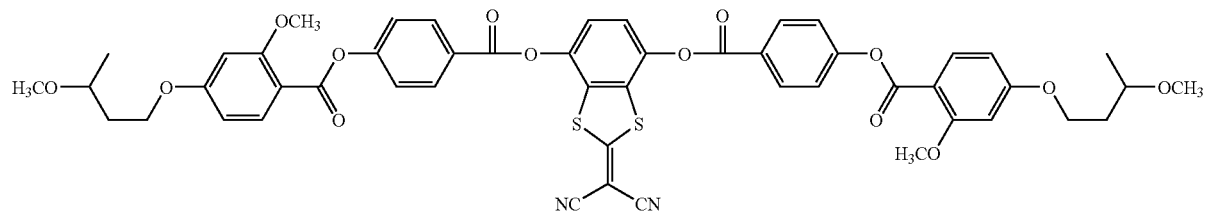
(51)
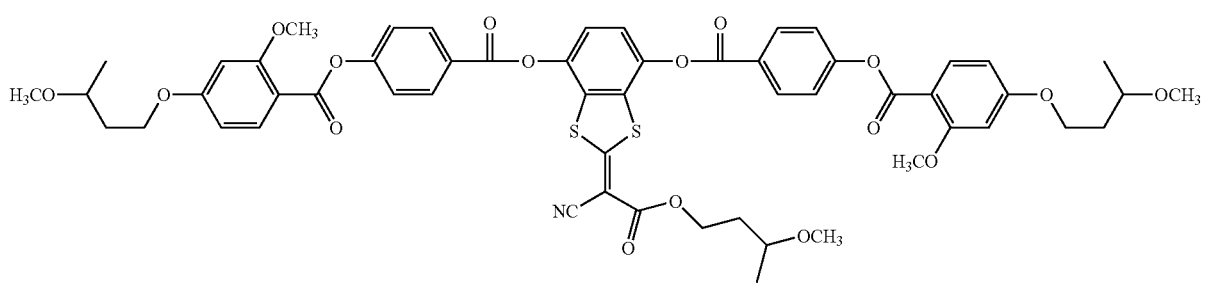

-continued
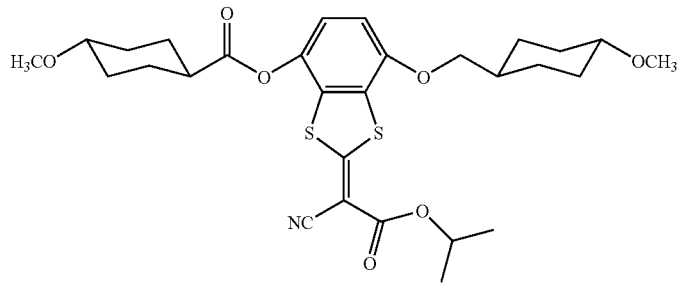
(52)
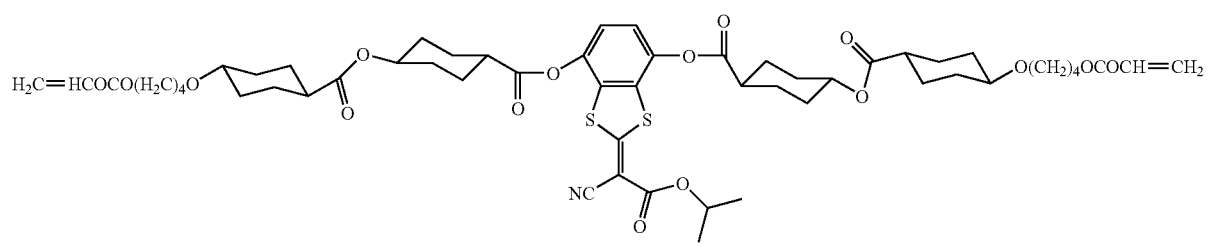
(53)
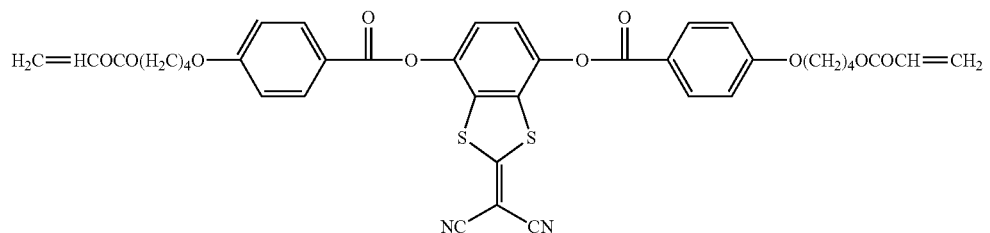
(54)
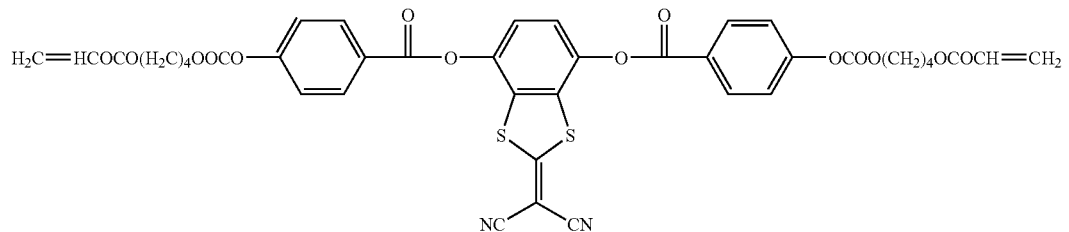
(55)
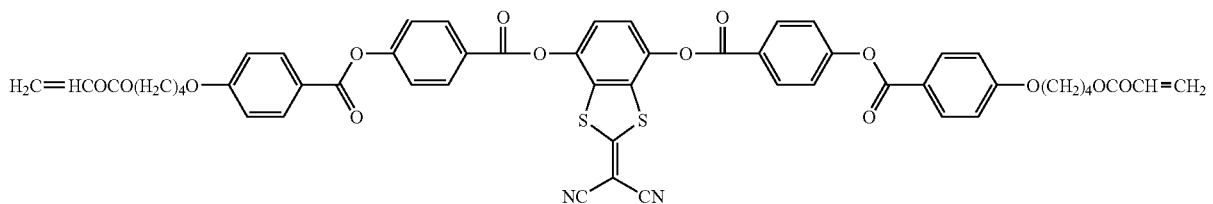
(56)
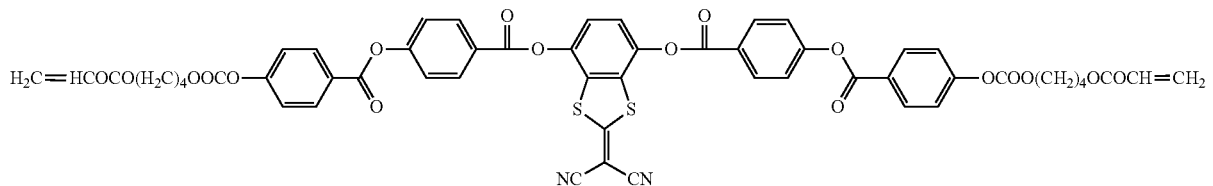
(57)

-continued
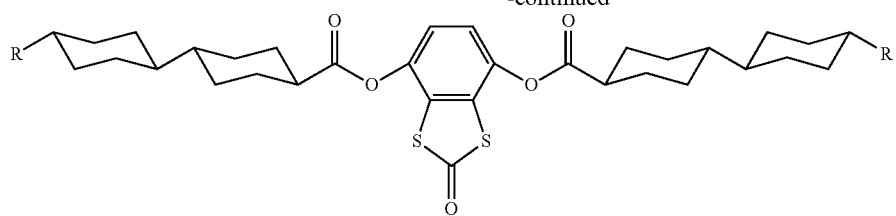
R = —C$_5$H$_{11}$ (58)
—C$_4$H$_9$ (59)
—C$_3$H$_7$ (60)
—C$_2$H$_5$ (61)
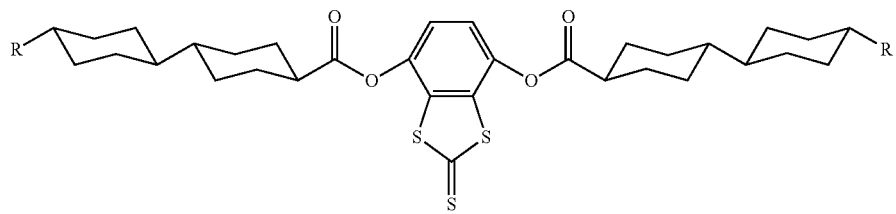
R = —C$_5$H$_{11}$ (62)
—C$_4$H$_9$ (63)
—C$_3$H$_7$ (64)
—C$_2$H$_5$ (65)
(66)
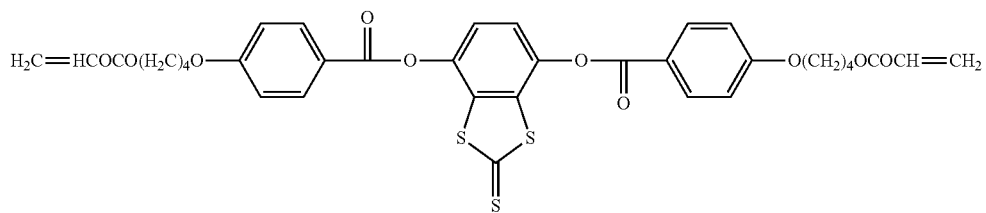
(67)
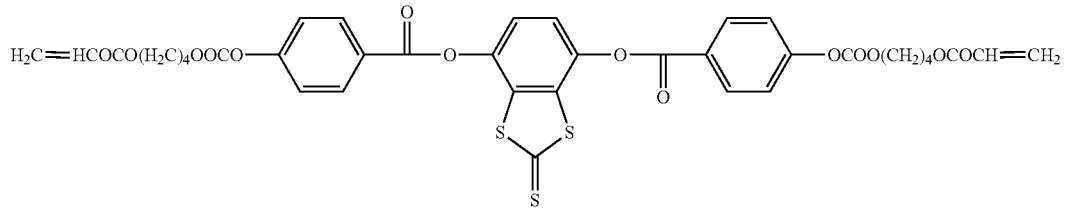
(68)
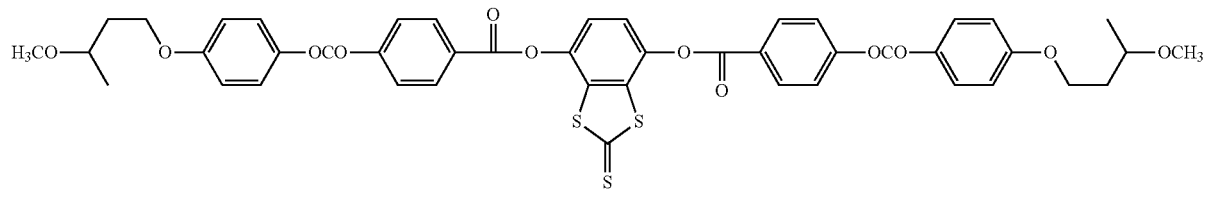
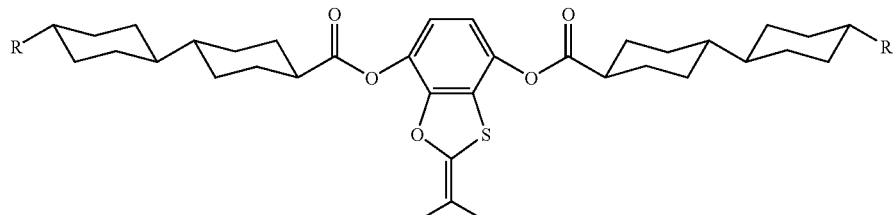
R = —C$_5$H$_{11}$ (69)
—C$_4$H$_9$ (70)
—C$_3$H$_7$ (71)
—C$_2$H$_5$ (72)

-continued
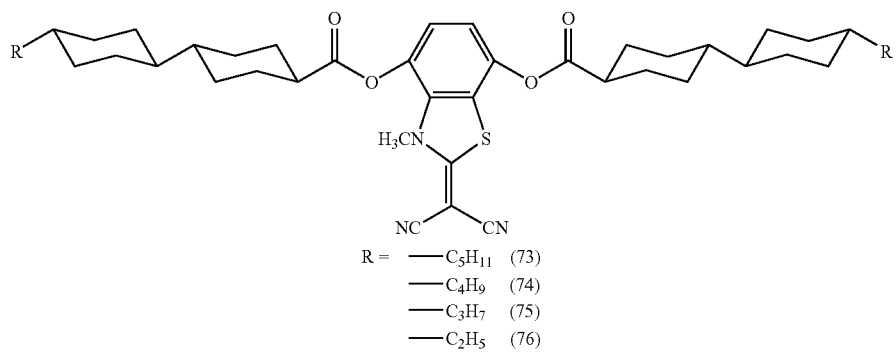
R = —C₅H₁₁ (73)
—C₄H₉ (74)
—C₃H₇ (75)
—C₂H₅ (76)
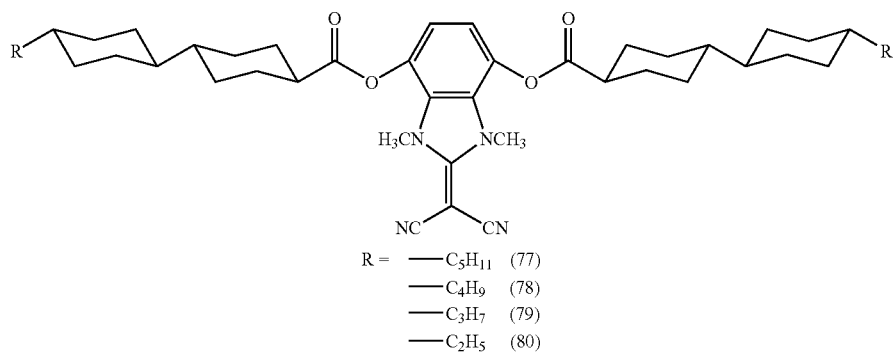
R = —C₅H₁₁ (77)
—C₄H₉ (78)
—C₃H₇ (79)
—C₂H₅ (80)
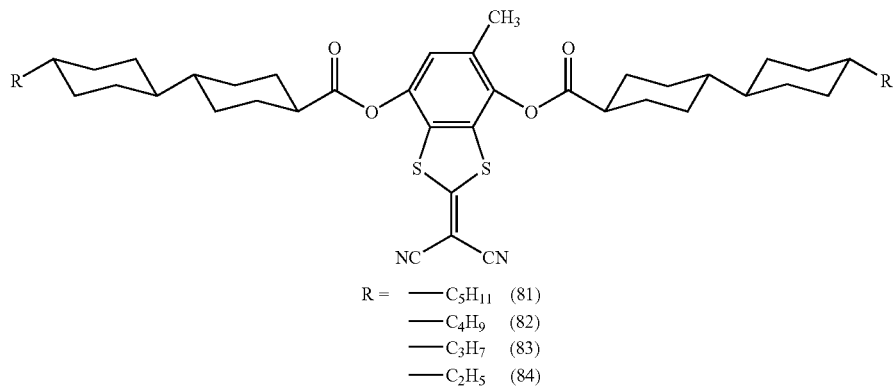
R = —C₅H₁₁ (81)
—C₄H₉ (82)
—C₃H₇ (83)
—C₂H₅ (84)
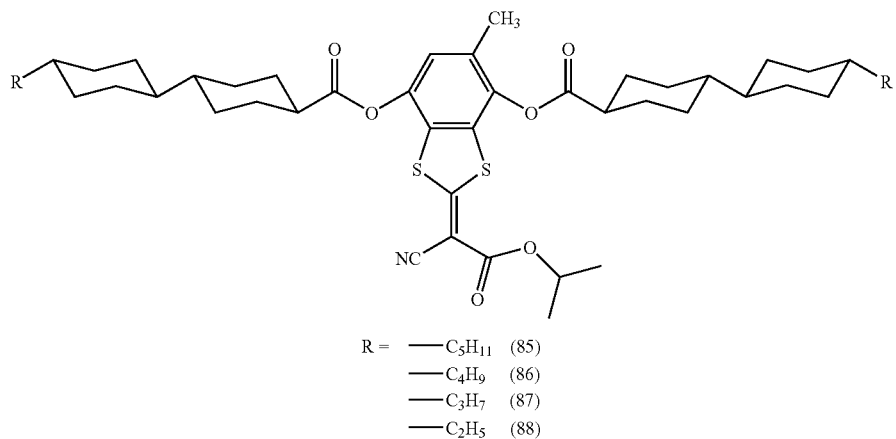
R = —C₅H₁₁ (85)
—C₄H₉ (86)
—C₃H₇ (87)
—C₂H₅ (88)

-continued
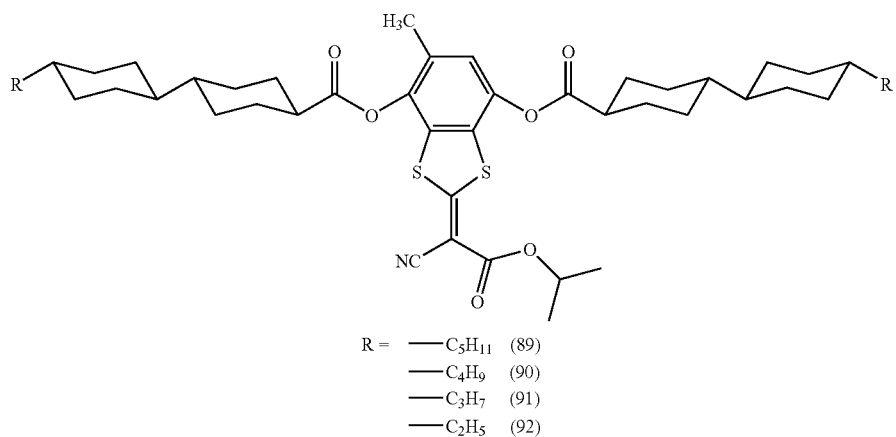
R = —C₅H₁₁ (89)
—C₄H₉ (90)
—C₃H₇ (91)
—C₂H₅ (92)
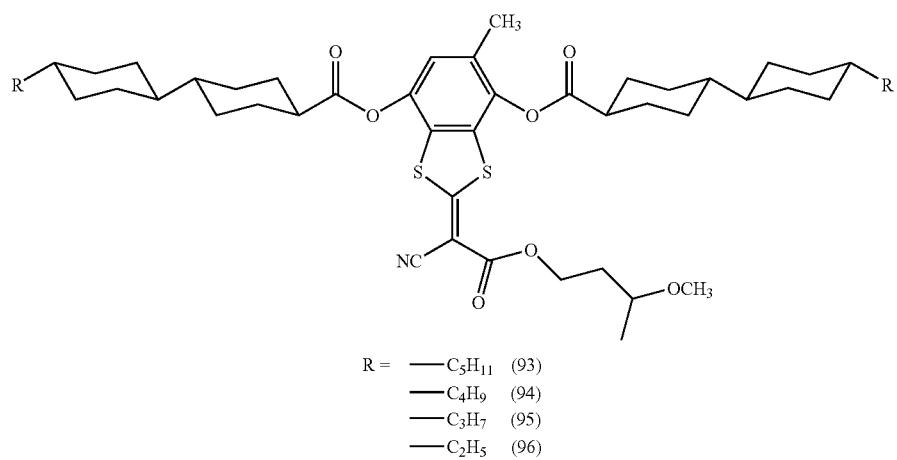
R = —C₅H₁₁ (93)
—C₄H₉ (94)
—C₃H₇ (95)
—C₂H₅ (96)
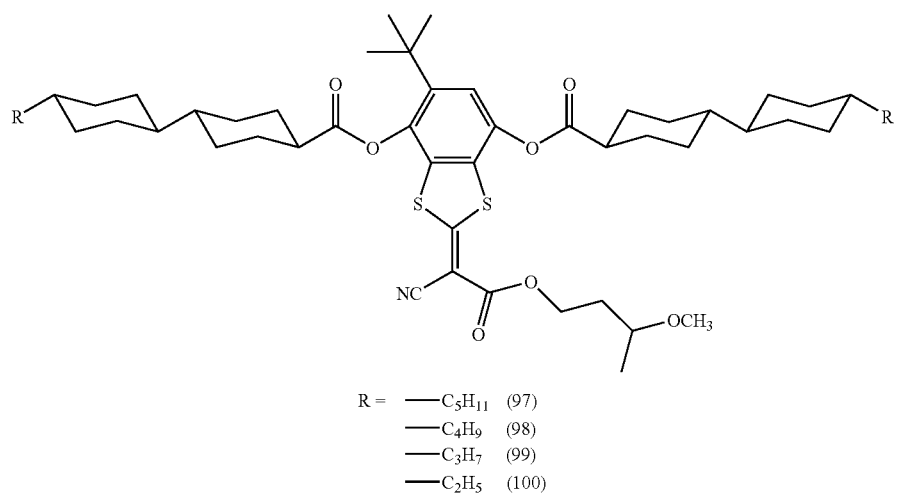
R = —C₅H₁₁ (97)
—C₄H₉ (98)
—C₃H₇ (99)
—C₂H₅ (100)

-continued
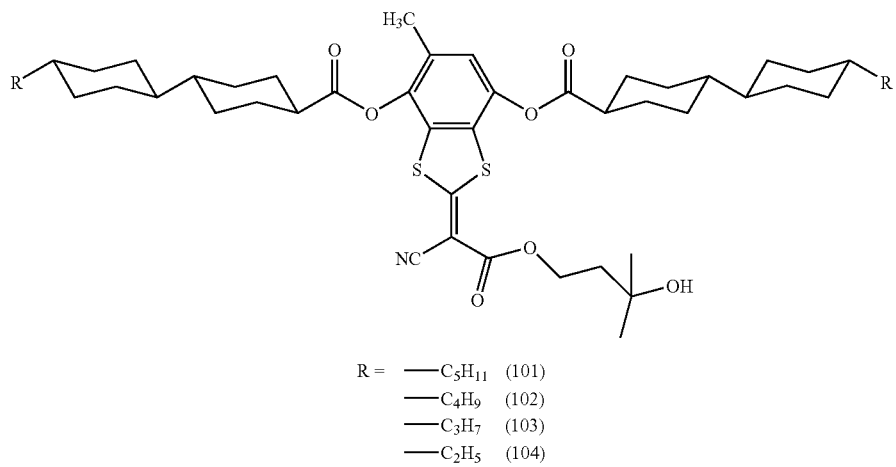
R = —C₅H₁₁ (101)
—C₄H₉ (102)
—C₃H₇ (103)
—C₂H₅ (104)
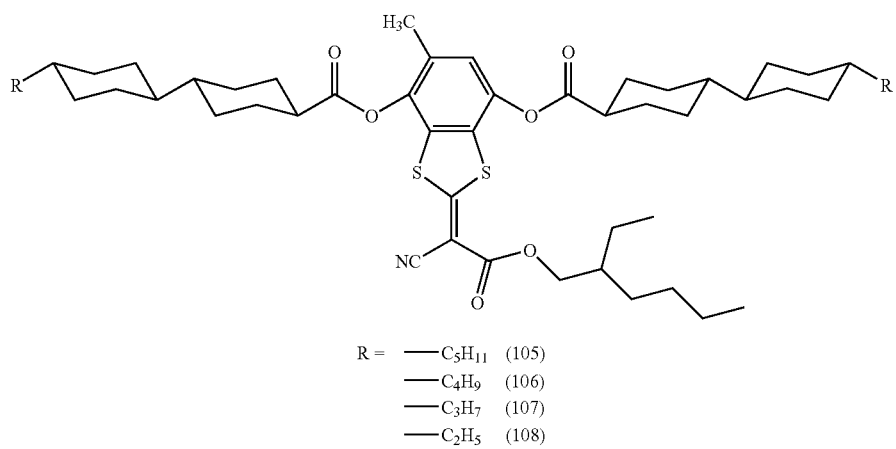
R = —C₅H₁₁ (105)
—C₄H₉ (106)
—C₃H₇ (107)
—C₂H₅ (108)
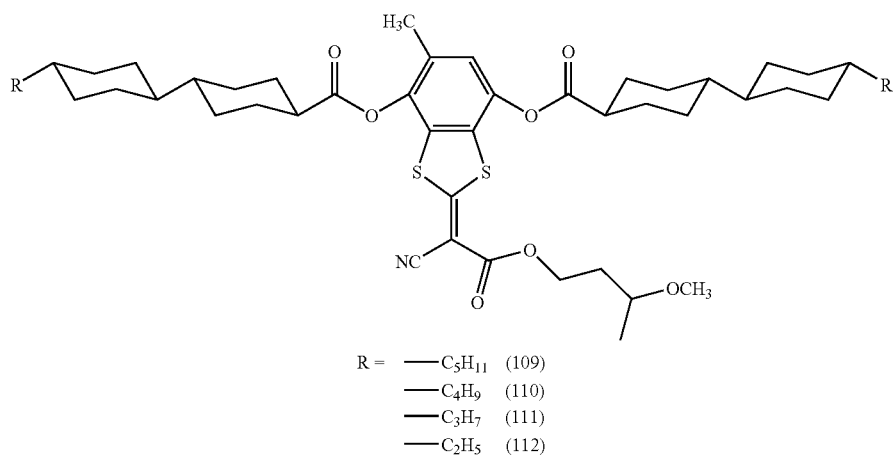
R = —C₅H₁₁ (109)
—C₄H₉ (110)
—C₃H₇ (111)
—C₂H₅ (112)

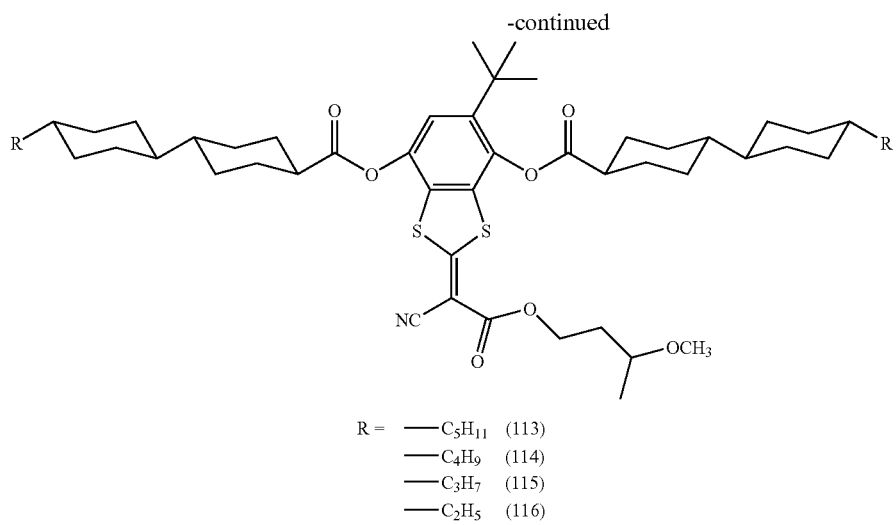
R = —C₅H₁₁ (113)
—C₄H₉ (114)
—C₃H₇ (115)
—C₂H₅ (116)
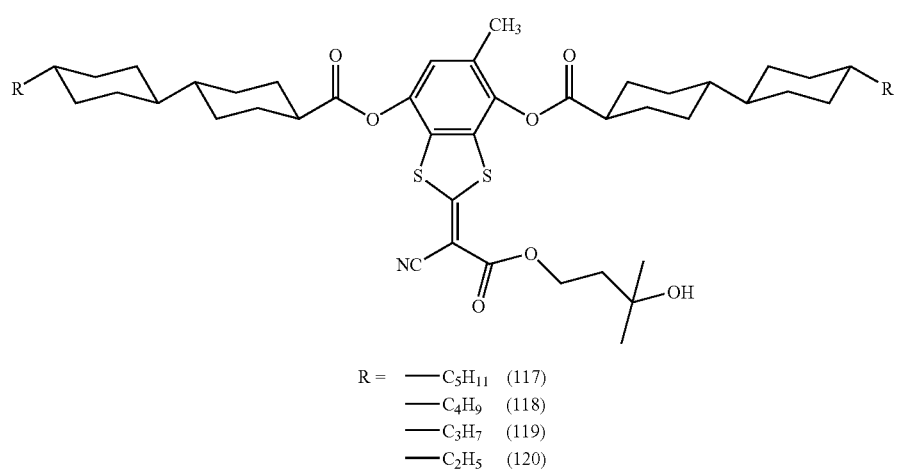
R = —C₅H₁₁ (117)
—C₄H₉ (118)
—C₃H₇ (119)
—C₂H₅ (120)
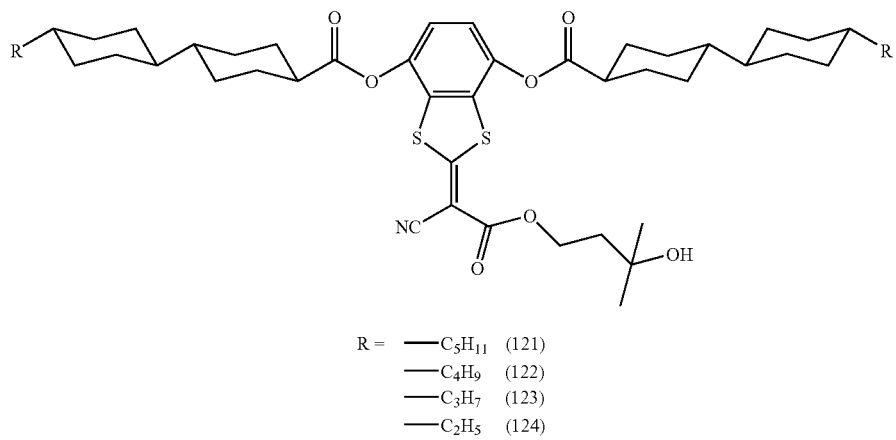
R = —C₅H₁₁ (121)
—C₄H₉ (122)
—C₃H₇ (123)
—C₂H₅ (124)

-continued
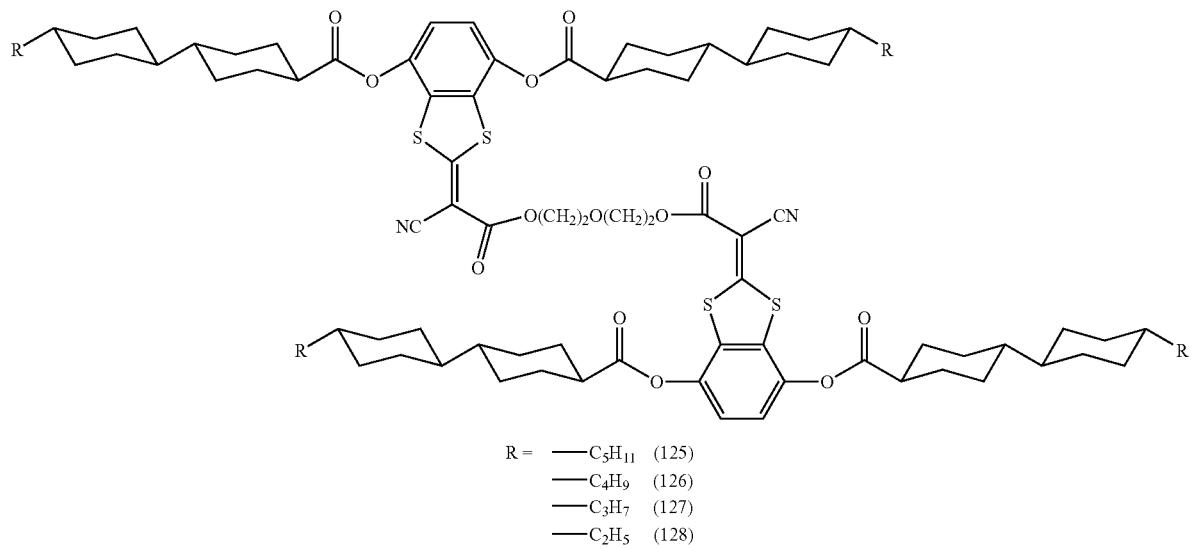
R = —C₅H₁₁ (125)
—C₄H₉ (126)
—C₃H₇ (127)
—C₂H₅ (128)
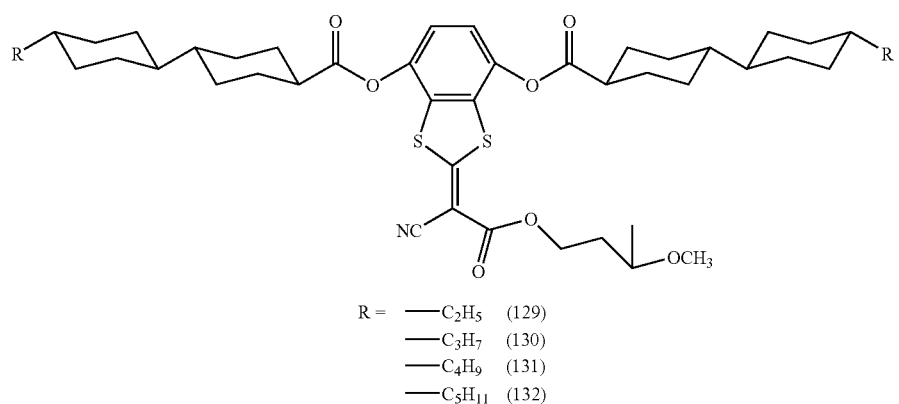
R = —C₂H₅ (129)
—C₃H₇ (130)
—C₄H₉ (131)
—C₅H₁₁ (132)
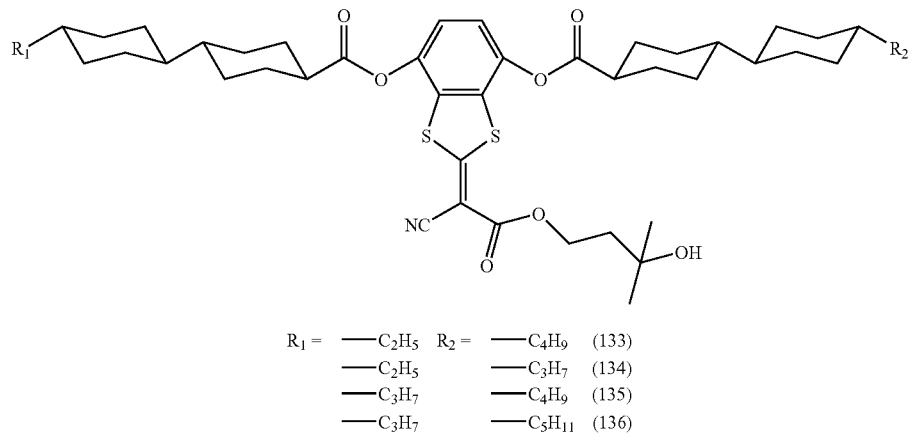
R₁ = —C₂H₅  R₂ = —C₄H₉ (133)
—C₂H₅  —C₃H₇ (134)
—C₃H₇  —C₄H₉ (135)
—C₃H₇  —C₅H₁₁ (136)

-continued
R₁ = 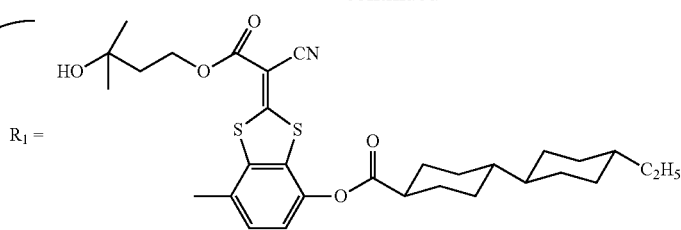
R₂ = 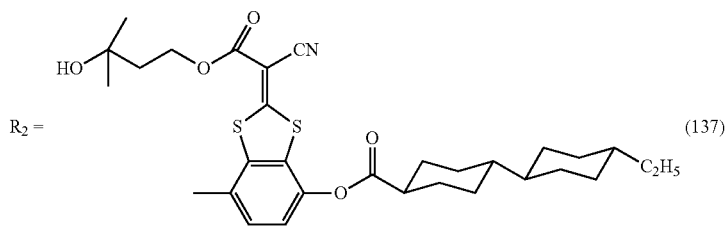
(137)
R₁ = 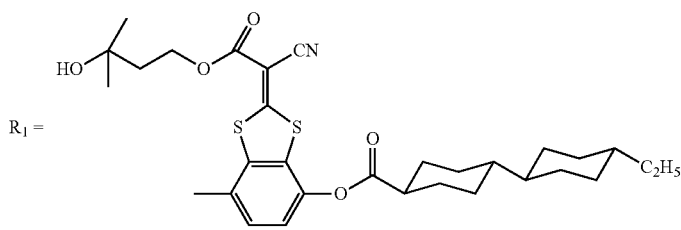
R₂ = 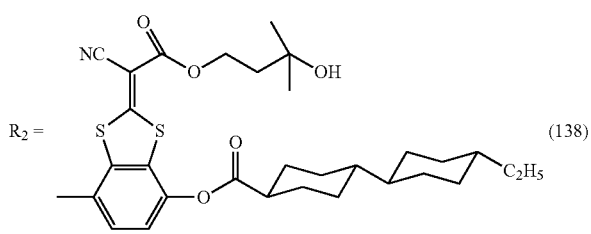
(138)
R₁ = 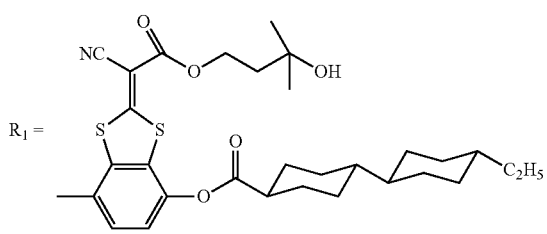
R₂ = 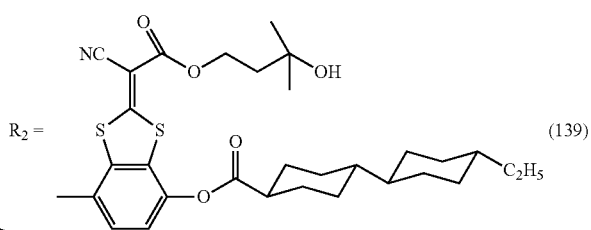
(139)

R₁ = 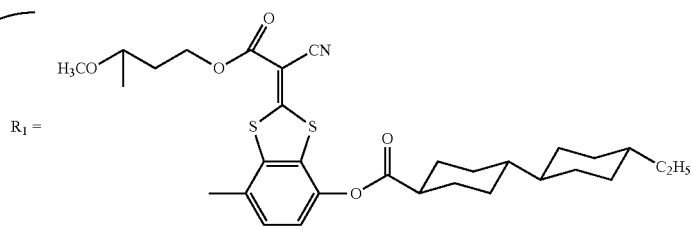
R₂ = 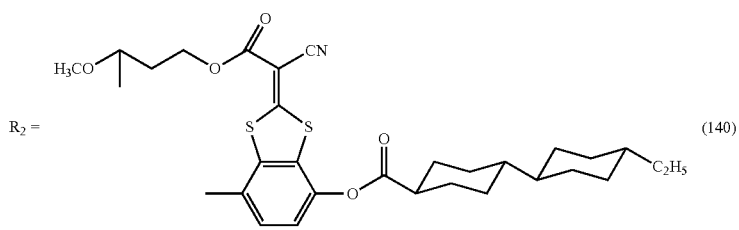
(140)
R₁ = 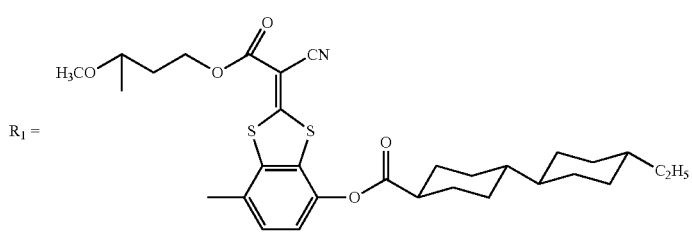
R₂ = 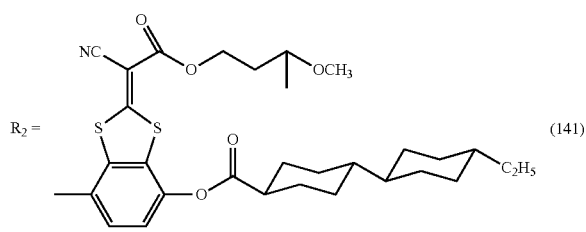
(141)
R₁ = 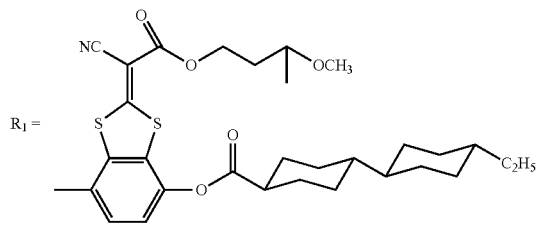
R₂ = 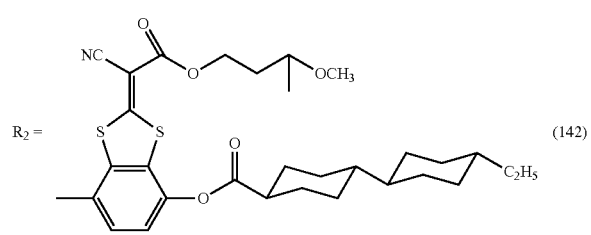
(142)

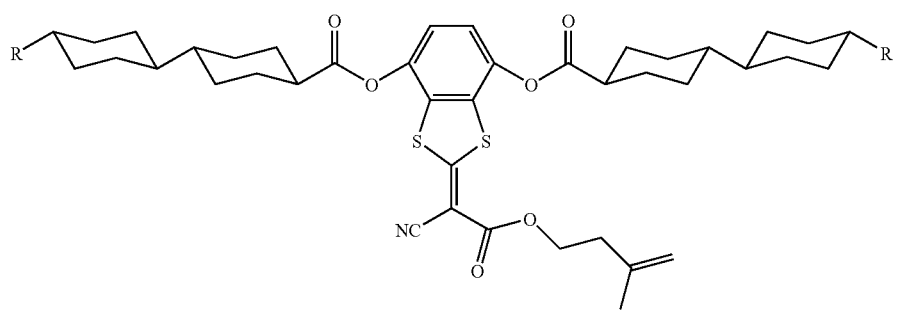
R = —C₂H₅ (143)
—C₃H₇ (144)
—C₄H₉ (145)
—C₅H₁₁ (146)
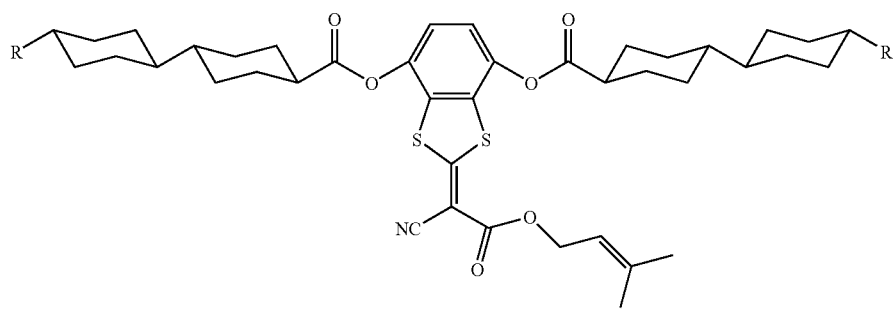
R = —C₂H₅ (147)
—C₃H₇ (148)
—C₄H₉ (149)
—C₅H₁₁ (150)
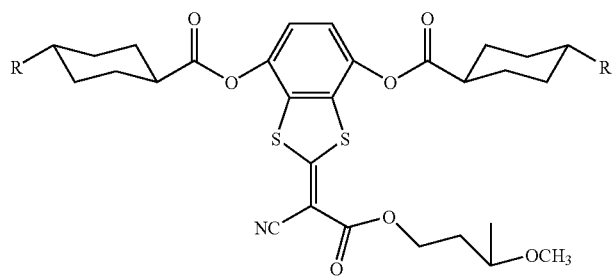
R = —H (151)
—C₄H₉ (152)
—C₅H₁₁ (153)
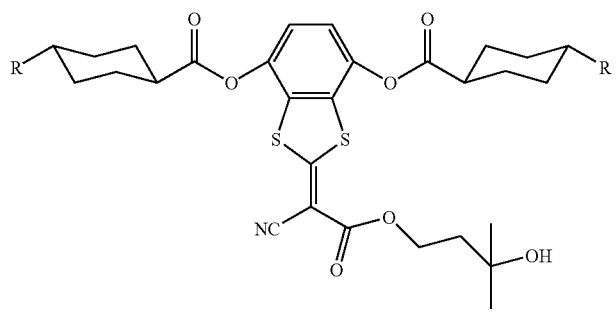
R = —H (154)
—C₄H₉ (155)
—C₅H₁₁ (156)

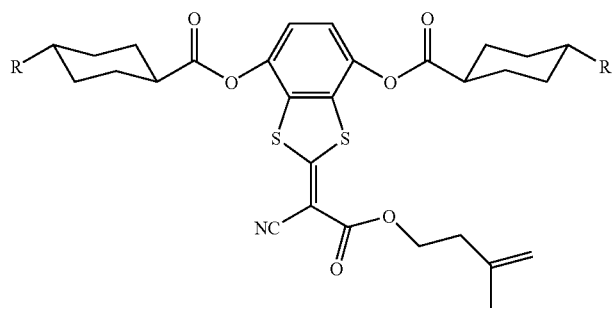
R = —H (157)
—C$_4$H$_9$ (158)
—C$_5$H$_{11}$ (159)
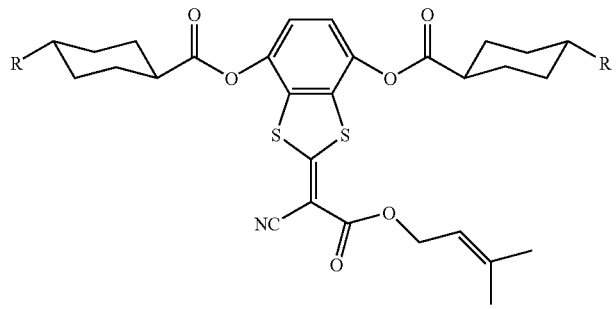
R = —H (160)
—C$_4$H$_9$ (161)
—C$_5$H$_{11}$ (162)
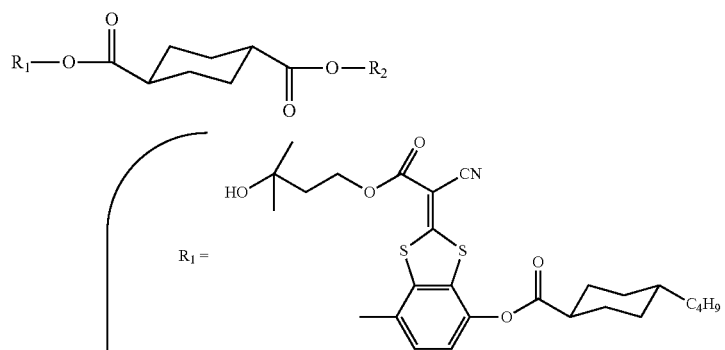
(163)

-continued
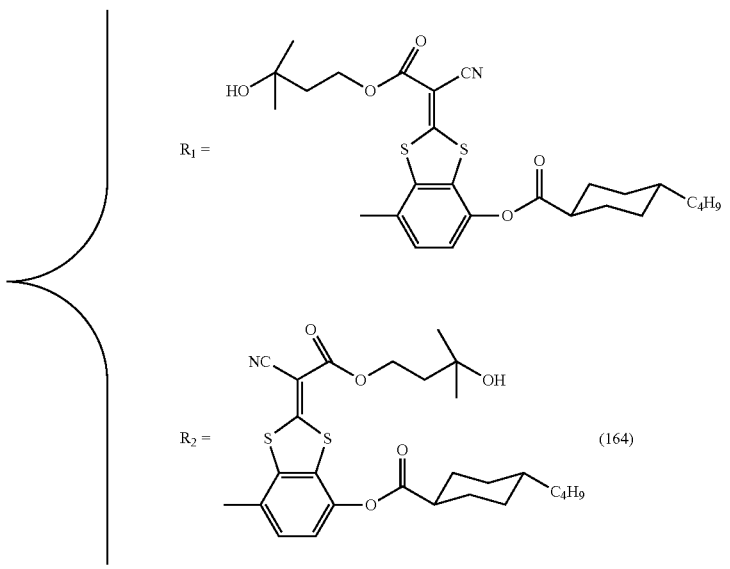
(164)
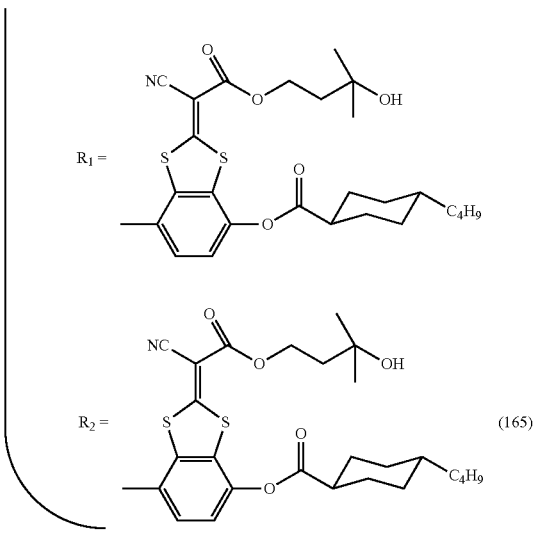
(165)
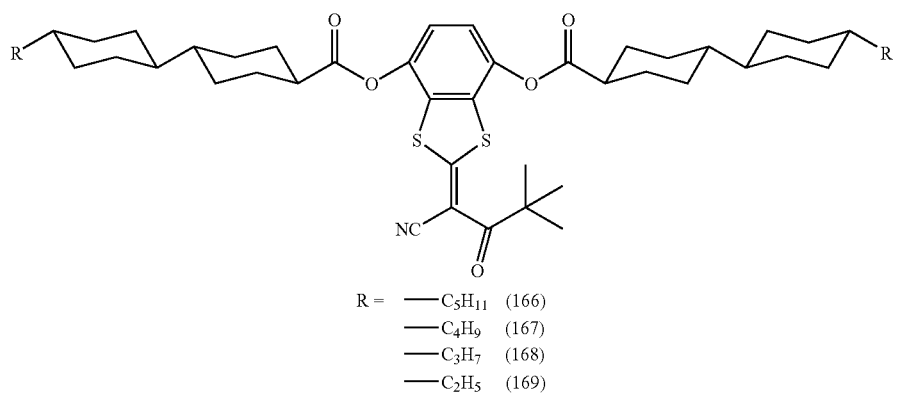
R =  —C$_5$H$_{11}$ (166)
    —C$_4$H$_9$ (167)
    —C$_3$H$_7$ (168)
    —C$_2$H$_5$ (169)

-continued
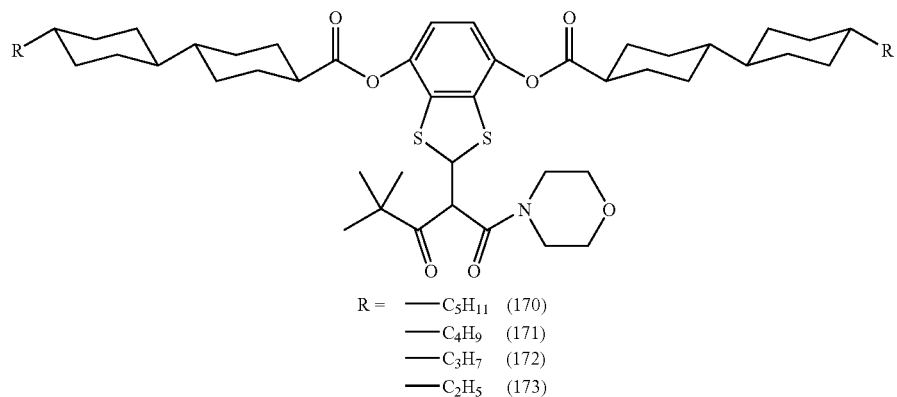
R = —C$_5$H$_{11}$ (170)
—C$_4$H$_9$ (171)
—C$_3$H$_7$ (172)
—C$_2$H$_5$ (173)
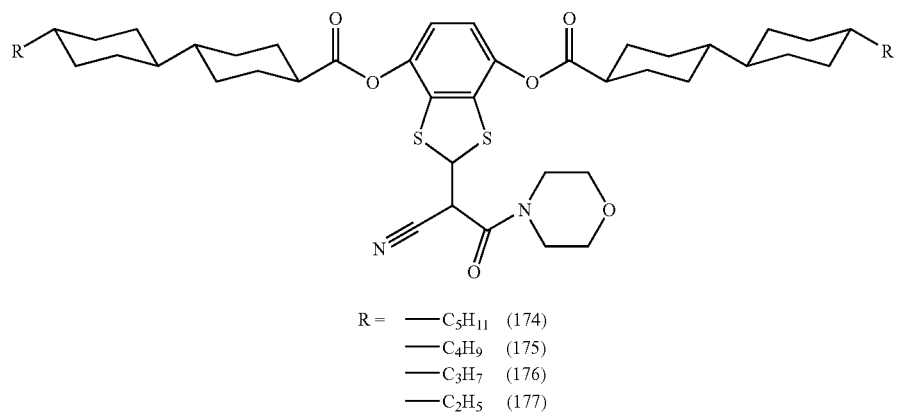
R = —C$_5$H$_{11}$ (174)
—C$_4$H$_9$ (175)
—C$_3$H$_7$ (176)
—C$_2$H$_5$ (177)
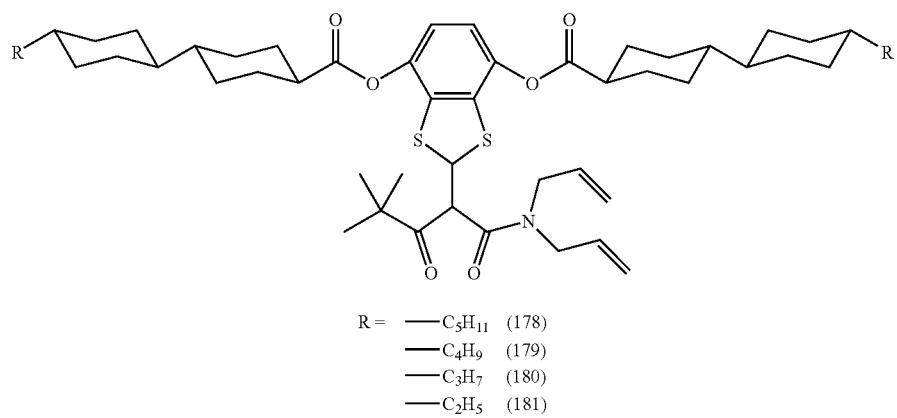
R = —C$_5$H$_{11}$ (178)
—C$_4$H$_9$ (179)
—C$_3$H$_7$ (180)
—C$_2$H$_5$ (181)
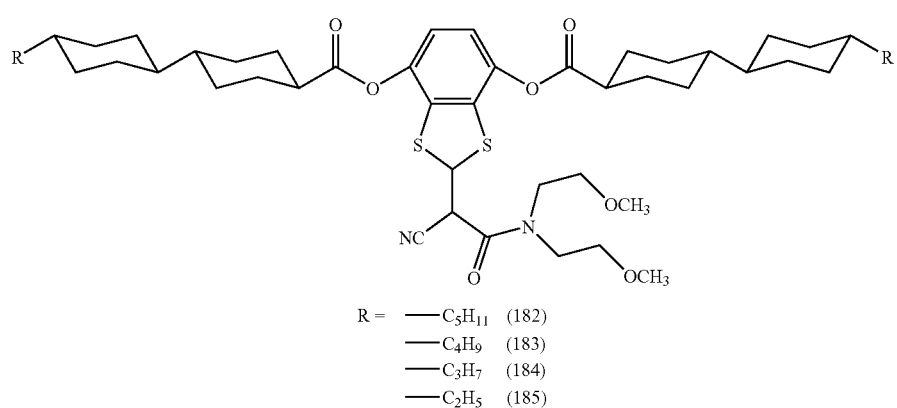
R = —C$_5$H$_{11}$ (182)
—C$_4$H$_9$ (183)
—C$_3$H$_7$ (184)
—C$_2$H$_5$ (185)

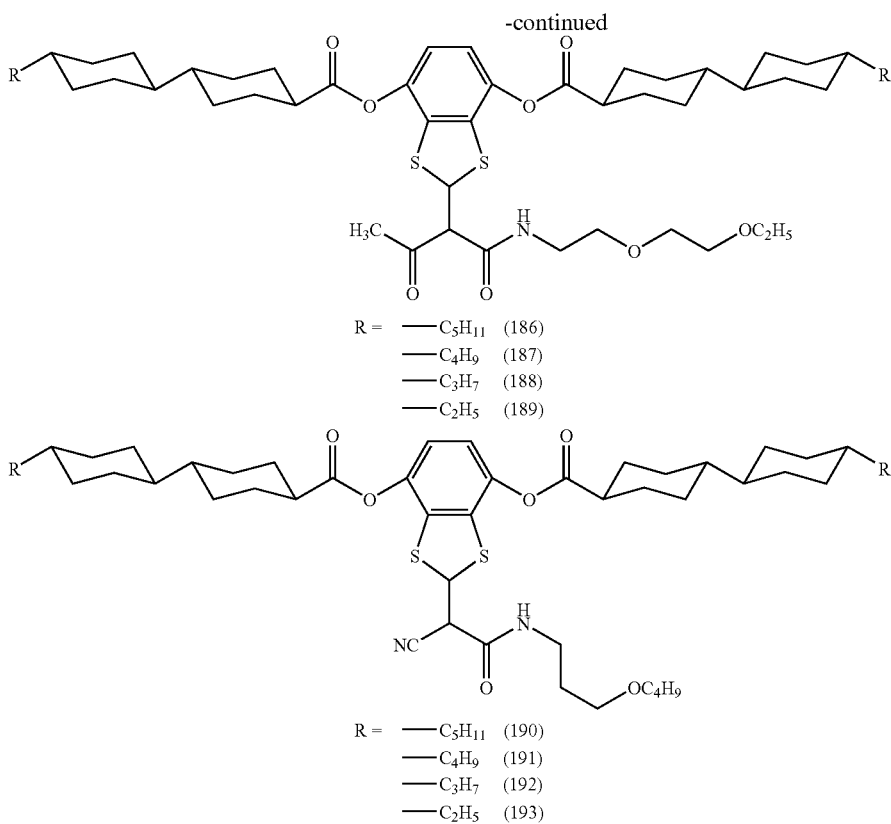

R = —C₅H₁₁ (186)
—C₄H₉ (187)
—C₃H₇ (188)
—C₂H₅ (189)

R = —C₅H₁₁ (190)
—C₄H₉ (191)
—C₃H₇ (192)
—C₂H₅ (193)

The compound represented by formula (I) or (II) can be synthesized in reference to known methods. For example, the exemplified compound (1) can be synthesized on the basis of the following scheme.

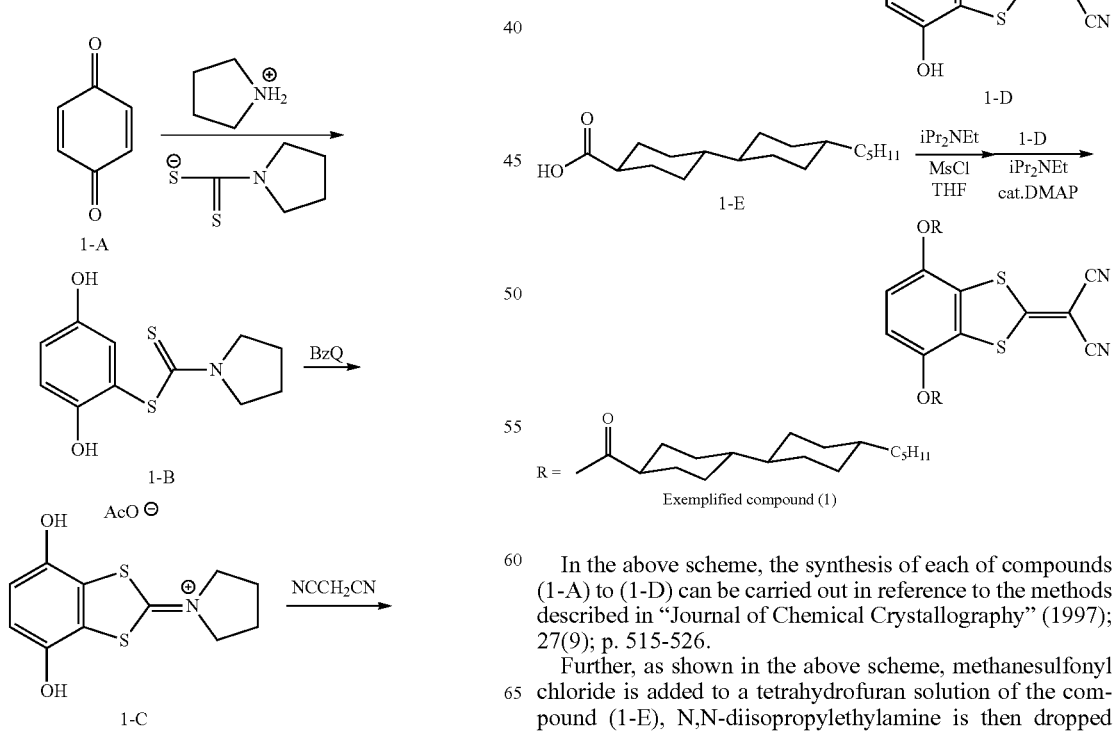

In the above scheme, the synthesis of each of compounds (1-A) to (1-D) can be carried out in reference to the methods described in "Journal of Chemical Crystallography" (1997); 27(9); p. 515-526.

Further, as shown in the above scheme, methanesulfonyl chloride is added to a tetrahydrofuran solution of the compound (1-E), N,N-diisopropylethylamine is then dropped therein, and the mixture was stirred. After that, N,N-diisopropylethylamine is added thereto, and a tetrahydrofuran solution of the compound (1-D) is dropped, followed by dropping a tetrahydrofuran solution of N,N-dimethylaminopyridine (DMAP), to thereby obtain the exemplified compound (1).

The compound represented by formula (I) or (II) serves as a retardation-controlling agent for an optical film (particularly, retardation-increasing and wavelength dispersion-controlling agent). In particular, it suitably serves as a retardation-controlling agent for obtaining a film having excellent wavelength dispersion property and Re-expression property with stretching.

Further, the compound represented by formula (I) or (II) can be also employed as a compound showing a liquid crystallinity, and a liquid crystal composition containing such a compound can be given. The content of the compound represented by formula (I) or (II) in the liquid crystal composition is properly determined depending on the need of reverse wavelength dispersion to be required.

[Polymer Composition]

The compound represented by formula (I) or (II) is preferably contained in a polymer composition. The polymer composition is not particularly limited as far as it is any of polymers generally used in the art. Examples thereof include polymer compositions composed of ester, carbonate, olefin, acetylene, cycloolefin, norbornene or the like, or cellulose compounds. It is preferable that the polymer composition comprises a cellulose compound as a main component.

Here, the phrase "comprises a cellulose compound as a main component" means that the content of the cellulose compound in the whole polymer composition is preferably 50 mass % or more, more preferably 75 mass %.

Further, in the present invention, the term "cellulose compound" refers to a compound having cellulose as a basic structure. In the present invention, the cellulose compound also means a compound having a cellulose skeleton obtained by introducing a functional group biologically or chemically into a cellulose to be used as a raw material. The cellulose compound is preferably a cellulose ester, and more preferably a cellulose acylate (examples thereof include a cellulose triacylate and a cellulose acylate propionate). Further, in the present invention, two or more cellulose acylates different from each other may be blended to use.

The composition that can be preferably used in the present invention is a cellulose compound composition comprising: at least one cellulose compound; and at least one of the compound represented by formula (I) or (II).

In the present invention, the content of the compound represented by formula (I) or (II) is preferably 0.1 to 50% by mass, more preferably 0.1 to 30% by mass, further preferably 0.5 to 30% by mass, and most preferably 1 to 30% by mass, to the cellulose compound.

The cellulose compound that can be used in the present invention is preferably a cellulose acylate.

A preferred embodiment of the cellulose compound that can be used in the present invention will be explained below, in which a cellulose acylate is to be an exemplified example.

<Cellulose Acylate Raw Cotton>

Examples of the cellulose of the cellulose acylate raw material that can be used in the present invention include cotton linter and wood pulp (broadleaf pulp, and conifer (needleleaf) pulp). Any cellulose acetate obtained from any raw cellulose may be used, and a plurality of celluloses may be used in combination of two or more thereof according to the need. There are detailed descriptions of these raw celluloses in, for example, "Plastic Material Lectures (17) Cellulose Resin" (Marusawa and Uda, The Nikkan Kogyo Shimbun, Ltd., published in 1970); and Japan Institute of Invention and Innovation, Kokai Giho (Open Technical Report) 2001-1745 (pp. 7 to 8), and the raw celluloses described in these publications may be used in the present invention, but these examples are not intended to be limiting of the cellulose acylate that can be used in the invention.

The aforementioned specific cellulose acylate is preferably a mixed fatty acid ester of a cellulose obtained by substituting a hydroxyl group of the cellulose with an acetyl group and a cellulose obtained by substituting a hydroxyl group with an acyl group having 3 or more carbon atoms, in which degree of substitution for a hydroxyl group of the cellulose satisfies the following expressions (5) and (6).

$$2.0 \leq A+B \leq 3.0 \qquad \text{Expression (5)}$$

$$0 < B \qquad \text{Expression (6)}$$

Herein, A represents the degree of substitution of an acetyl group substituting for a hydroxyl group of the cellulose, and B represents the degree of substitution of an acyl group having 3 or more carbon atoms substituting for a hydroxyl group of the cellulose.

Each of the glucose units, which constitute cellulose by bonding through β-1,4-glycoside bond, has free hydroxyl groups at the 2-, 3-, and 6-positions thereof. A cellulose acylate is a polymer obtained by esterifying a part or the whole of these hydroxyl groups with an acyl group(s). Herein, the "substitution degree" means the ratio of esterification at the 2-, 3-, or 6-positions in the cellulose. Specifically, the 100% esterification of any one of the 2-, 3-, and 6-positions is a substitution degree of 1.

<Degree of Polymerization of Cellulose Acylate>

The degree of polymerization of cellulose acylate that can be used in the present invention is preferably 180 to 700 in terms of viscosity average degree of polymerization. In the case of cellulose acetate, the degree of polymerization is preferably 180 to 550, more preferably 180 to 400, and particularly preferably 180 to 350, in terms of viscosity average degree of polymerization. By adjusting the degree of polymerization to 700 or less, the viscosity of a dope solution of cellulose acylate becomes an adequate one and the production of a film by flow casting then tends to be facilitated. In addition, adjusting the degree of polymerization to 180 or more is preferable because the strength of a film formed can be further increased. The average polymerization degree can be measured by a limiting viscosity method by Uda et al., (Kazuo Uda and Hideo Saito, "The Journal of the Society of Fiber Science and Technology, Japan", Vol. 18, No. 1, pp. 105 to 120, 1962). Specifically, it can be determined according to the method described in JP-A-9-95538.

Further, the distribution of molecular weight of a cellulose acylate that can be used in the present invention is evaluated by gel permeation chromatography. It is preferable that the polydisperse index Mw/Mn (Mw, mass average molecular weight; and Mn, number average molecular weight) be small and the distribution of molecular weight be narrow. Specifically, the value of Mw/Mn is preferably from 1.0 to 3.0, more preferably from 1.0 to 2.0, and particularly preferably from 1.0 to 1.6.

If a low molecular weight component(s) is removed from the cellulose acylate, the average molecular weight (polymerization degree) thereof becomes higher, but the viscosity thereof becomes lower than that of ordinary cellulose acylate, which means that the removal is useful. A cellulose acylate containing a low molecular weight component(s) at a small ratio can be obtained by removing the low molecular weight component(s) from a cellulose acylate synthesized in a usual manner. The removal of the low molecular weight component(s) can be carried out by washing the cellulose acylate with an appropriate organic solvent. When the cellulose acylate containing a small amount of the low molecular weight component(s) is to be produced, the amount of a sulfuric acid catalyst in the acetylation reaction is preferably adjusted to 0.5 to 25 parts by mass to 100 parts by mass of the cellulose. When the amount of the sulfuric acid catalyst is set within the range, a cellulose acylate having a preferable molecular weight distribution (uniform molecular weight distribution) can be synthesized. In the case that the cellulose acylate is used when the cellulose acylate film is produced, the percentage of water content in the cellulose acylate is preferably 2 mass % or less, more preferably 1 mass % or less, particularly preferably 0.7 mass % or less. It is known that cellulose acylate generally contains water in an amount of 2.5 to 5% by mass. Thus, in order to set the percentage of water content in the cellulose acylate within the range, it is preferably to dry ordinary cellulose acylate. The method for the drying is not particularly limited as far as the target percentage of water content can be attained.

About the cellulose acylate that can be used in the present invention, the starting cotton thereof, and the synthesis method thereof are described in detail in, for example, "Kokai Giho" by Japan Institute of Invention & Innovation (Kogi No. 2001-1745, published on Mar. 15, 2001), pp. 7 to 12, and they can be applied to the present invention.

<Additive to Cellulose Acylate>

To a cellulose acylate solution that can be used in the present invention, in addition to the compound represented by formula (I) or (II), any of various additives (for example, a ultraviolet absorber, a plasticizer, a deterioration preventing agent, fine particles, and an optical-characteristic controlling agent) may be added. As to the timing at which the compound represented by formula (I) or (II) and the other additive(s) is added, they may be added in any of the dope production steps. They may be added in the last step (as a control step) of the dope preparation steps.

The additive(s) may be in a solid or oily state. That is, there is no particular limitation to the melting points or boiling points of the additives. For example, a ultraviolet absorber having a melting point of less than 20° C. and a ultraviolet absorber having a melting point of 20° C. or more are used in combination; or, similarly, plasticizers may be used in combination. Specifically, the method described in JP-A-2001-151901 can be applied to the present invention.

(Ultraviolet Absorber)

Any kind of ultraviolet absorber can be selected according to the purpose of use, and examples of the UV absorber that can be used include those of salicylate ester-series, benzophenone-series, benzotriazole-series, benzoate-series, cyanoacrylate-series, and nickel complex-series; and a benzophenone-series, benzotriazole-series, or salicylate ester-series UV absorber is preferable.

Examples of the benzophenone-series ultraviolet absorber include 2,4-dihydroxybenzophenone, 2-hydroxy-4-acetoxybenzophenone, 2-hydroxy-4-methoxybenzophenone, 2,2'-di-hydroxy-4-methoxybenzophenone, 2,2'-di-hydroxy-4,4'-methoxybenzophenone, 2-hydroxy-4-n-octoxybenzophenone, 2-hydroxy-4-dodecyloxybenzophenone, and 2-hydroxy-4-(2-hydroxy-3-methacryloxy)propoxybenzophenone.

Examples of the benzotriazole-series ultraviolet absorber include 2-(2'-hydroxy-3'-tert-butyl-5'-methylphenyl)-5-chlorobenzotriazole, 2-(2'-hydroxy-5'-tert-butylphenyl)benzotriazole, 2-(2'-hydroxy-3',5'-di-tert-amylphenyl)benzotriazole, 2-(2'-hydroxy-3',5'-di-tert-butylphenyl)-5-chlorobenzotriazole, and 2-(2'-hydroxy-5'-tert-octylphenyl)benzotriazole.

Examples of the salicylate ester-series ultraviolet absorber include phenyl salicylate, p-octylphenyl salicylate, and p-tert-butylphenyl salicylate.

Of the ultraviolet absorbers as enumerated in the above, in particular, 2-hydroxy-4-methoxybenzophenone, 2,2'-di-hydroxy-4,4'-dimethoxybenzophenone, 2-(2'-hydroxy-3'-tert-butyl-5'-methylphenyl)-5-chlorobenzotriazole, 2-(2'-hydroxy-5'-tert-butylphenyl)benzotriazole, 2-(2'-hydroxy-3',5'-di-tert-amylphenyl)benzotriazole, 2-(2'-hydroxy-3',5'-di-tert-butylphenyl)-5-chlorobenzotriazole are particularly preferable.

It is preferable to use two or more ultraviolet absorbers having different absorption wavelength in combination, because great shielding ability can be obtained in a wide wavelength range. As the ultraviolet absorber for liquid crystal, preferable one is a ultraviolet absorber which is excellent in absorption ability for ultraviolet ray of wavelength 370 nm or lower, from the viewpoint of prevention of degradation of the liquid crystal, and which has less absorption of visible light of wavelength 400 nm or higher, from the viewpoint of displaying ability of the liquid crystal. Examples of the particularly preferable ultraviolet absorber include the aforementioned benzotriazole-series compounds, benzophenone-series compounds, and salicylate ester-series compounds. Among these, benzotriazole-series compounds are especially preferable, because of little coloration which is unnecessary against cellulose ester.

Further, as the UV absorber, use can also be made of any of the compounds described in JP-A-60-235852, JP-A-3-199201, JP-A-5-1907073, JP-A-5-194789, JP-A-5-271471, JP-A-6-107854, JP-A-6-118233, JP-A-6-148430, JP-A-7-11056, JP-A-7-11055, JP-A-7-11056, JP-A-8-29619, JP-A-8-239509, and JP-A-2000-204173.

The amount of the ultraviolet absorber to be added is preferably 0.001 to 5 mass %, more preferably 0.01 to 1 mass %, to the cellulose acylate. When the amount to be added is not less than 0.001 mass %, the addition effect can be sufficiently exhibited, which is preferable, and when the amount to be added is not more than 5 mass %, the ultraviolet absorber can be prohibited from being bleed out on the film surface, which is preferable.

Further, the ultraviolet absorber may be added at the same time upon dissolving a cellulose acylate, or may be added into the cellulose acylate solution (dope) after dissolution. It is particularly preferred that an ultraviolet absorber solution is added to the dope immediately before casting, by means of a static mixer or the like, thereby optical absorption characteristics can be easily controlled.

(Deterioration Preventing Agent)

The deterioration preventing agent may be added to prevent cellulose triacetate etc. from its degradation and decomposition. As the deterioration preventing agent, butyl amine, hindered amine compounds (JP-A-8-325537), guanidine compounds (JP-A-5-271471), benzotriazole-series UV absorbers (JP-A-6-235819), benzophenone-series UV absorbers (JP-A-6-118233), or the like can be used.

(Plasticizer)

The plasticizer that can be used in the present invention is preferably a phosphate and/or a carboxylate. Preferred examples of the phosphate-series plasticizer include triphenyl phosphate (TPP), tricresyl phosphate (TCP), cresyl diphenyl phosphate, octyl diphenyl phosphate, biphenyl diphenyl phosphate (BDP), trioctyl phosphate, and tributyl phosphate. Preferred examples of the carboxylate-series plasticizer include dimethyl phthalate (DMP), diethyl phthalate (DEP), dibutyl phthalate (DBP), dioctyl phthalate (DOP), diphenyl phthalate (DPP), diethyl hexyl phthalate (DEHP), triethyl o-acetylcitrate (OACTE), tributyl o-acetylcitrate (OACTB), triethyl acetyl citrate, tributyl acetyl citrate, butyl oleate, methyl acetyl ricinoleate, dibutyl sebacate, triacetin, tributyrin, butyl-phthalyl-butyl glycolate, ethyl phthalyl ethyl glycolate, methyl phthalyl ethyl glycolate, and butyl-phthalyl-butyl glycolate. Further, the plasticizer is preferably a (di)pentaerythritol ester, a glycerol ester, or a diglycerol ester.

(Peeling Accelerator)

Examples of the peeling accelerator include ethyl esters of citric acid.

(Infrared Absorber)

Preferred examples of the infrared absorber include those described in, for example, JP-A-2001-194522.

(Dye)

Further, in the present invention, a dye may be added, to adjust the hue of the resultant film. The amount to be added of the dye is preferably 10 to 1,000 ppm, more preferably 50 to 500 ppm, in terms of ratio by mass to the cellulose acylate. The light piping of the cellulose acylate film can be reduced and the yellowish feel of the cellulose acylate film can be improved, by adding the dye(s) in this manner. The dye may be added together with a cellulose acylate or a solvent, when the cellulose acylate solution is prepared; or alternatively the dye may be added during or after the preparation of the solution. Further, the dye may be added in the ultraviolet absorber solution, which is to be in-line-added. The dyes described in, for example, JP-A-5-34858 may also be used.

(Matting Agent Fine-Particles)

To the cellulose acetate film according to the present invention, fine particles as a matting agent may be added. Examples of the fine particles that can be used in the present invention include silicon dioxide, titanium dioxide, aluminum oxide, zirconium oxide, calcium carbonate, talc, clay, calcined kaolin, calcined calcium silicate, hydrated calcium silicate, aluminum silicate, magnesium silicate, and calcium phosphate. The fine particles are preferably those containing silicon, from the viewpoint of obtaining low turbidity, and particularly silicon dioxide is preferable. Fine particles of silicon dioxide are preferably those having a primary average particle diameter of 20 nm or less and an apparent specific gravity of 70 g/L or more. Particles having a primary average particle diameter as small as 5 to 16 nm are able to reduce the haze of the film, and are hence more preferable. The apparent specific gravity is preferably 90 to 200 g/L, and more preferably 100 to 200 g/L. A larger apparent specific gravity makes it possible to prepare a high concentration dispersion, to thereby better haze and coagulation, which is preferable.

The fine particles generally form secondary particles having an average particle diameter (size) of 0.1 to 3.0 μm; and the fine particles exist in the form of a coagulate of primary particles in the film, to thereby being capable of forming irregularities having 0.1 to 3.0 μm in size on the surface of the film. The secondary average particle diameter is preferably 0.2 μm or more and 1.5 μm or less, more preferably 0.4 μm or more and 1.2 μm or less, and most preferably 0.6 μm or more and 1.1 μm or less. Herein, the primary particle diameter and the secondary particle diameter are determined in the following manner: Particles in the film are observed by a scanning type electron microscope to measure the diameter of a circumscribed circle of a particle as a particle diameter. Further, 200 particles each in a different site or place are observed, to calculate an average of the diameters of these particles to determine an average particle diameter.

As the fine particles of silicon dioxide, for example, commercially available products under such trade names as Aerosil R972, R972V, R974, R812, 200, 200V, 300, R202, OX50, TT600 (manufactured by Nippon Aerosil Co., Ltd.) may be used. The fine particles of zirconium oxide are commercially available, for example, under such trade names as Aerosil R976 and R811 (manufactured by Nippon Aerosil Co., Ltd.), which may be used in the present invention.

Of those fine particles, Aerosil 200V and Aerosil R972V are particularly preferable, since they are fine particles of silicon dioxide having an average primary particle diameter of 20 nm or less and an apparent specific gravity of 70 g/L or more, and having a large effect of dropping friction coefficient, while maintaining the low turbidity of a resulting optical film.

In the present invention, to obtain a cellulose acylate film containing particles having a small secondary average particle diameter, several methods can be applied in the process of preparing a dispersion of fine particles. For example, in one method, a fine-particle dispersion obtained by mixing and stirring a solvent and fine particles, is prepared in advance. This fine particle dispersion is added into a small amount of a cellulose acylate solution which is separately prepared, and the mixture is dissolved with stirring. Then, the obtained mixture is further mixed in a main cellulose acylate dope solution. This method is a preferable preparation method in the point that the silicon dioxide fine-particles are well dispersed and are scarcely re-coagulated. Besides the above method, there is a method in which a small amount of a cellulose ester is added to a solvent, dissolved with stirring, fine particles are added thereto, and followed by dispersing by a dispersing apparatus, to obtain a fine-particle addition solution, which is sufficiently mixed with a dope solution by using an inline mixer. The present invention is not particularly limited by those methods, but the concentration of silicon dioxide when silicon dioxide fine-particles are mixed with and dispersed in, for example, a solvent is preferably 5 to 30 mass %, more preferably 10 to 25 mass %, and most preferably 15 to 20 mass %. The higher the concentration of the dispersion is, the lower the liquid turbidity in relation to the amount to be added is and the more greatly the haze and coagulate are bettered, and thus a higher concentration of silicon dioxide is preferable. The amount of the matting agent to be added in the final dope solution of the cellulose acylate is preferably 0.01 to 1.0 $g/m^2$, more preferably 0.03 to 0.3 $g/m^2$, and most preferably 0.08 to 0.16 $g/m^2$.

Preferable examples of a lower alcohol to be used as the solvent include methyl alcohol, ethyl alcohol, propyl alcohol, isopropyl alcohol, and butyl alcohol. As the solvent other than the lower alcohol, a solvent which is usually used for forming a cellulose ester film is preferably used, though not particularly limited to these solvents.

(Ratios of Compounds to be Added)

In the cellulose acylate film of the present invention, the total amount of compounds having a molecular weight of 3,000 or less is preferably 5 to 45 mass %, more preferably 10 to 40 mass %, and further preferably 15 to 30 mass %, to the mass of the cellulose acylate. These compounds include, as mentioned above, compounds lowering optical anisotropy, agents for controlling wavelength dispersion, ultraviolet absorbers (preventives), plasticizers, deterioration preventing agents, fine particles, releasing agents (peeling accelerators), and infrared absorbers. Further, it is preferable that the total amount of compounds having molecular weights of 2,000 or less be in the above ranges. By adjusting the total amount of the compounds to 5 mass % or more, it becomes difficult to expose the nature of cellulose acylate as a single substance.

For instance, the optical characteristics or physical strength of the film are hardly varied due to the change of temperature and humidity. In addition, it is preferable to adjust the total amount of those compounds to 45 mass % or less, because the amount of the compounds does not exceed the limit in which the compounds are compatible in the cellulose acylate film, and as a result, the film is prevented from being whitened or whitely turbid by precipitation of the compounds on the surface of the film (flow or bleed out from a film).

<Organic Solvent of Cellulose Acylate Solution>

In the present invention, the cellulose acylate film is preferably prepared according to a solvent cast method. In the solvent cast method, it is preferable that a solution (dope) in which a cellulose acylate is dissolved in an organic solvent is used, to prepare a film. The organic solvent, which is preferably used as a main solvent in the present invention, is preferably one selected from a ketone, an ether and an ester having 3 to 12 carbon atoms, and a halogenated hydrocarbon having 1 to 7 carbon atoms. The ester, ketone, or ether may have a cyclic structure. A compound having two or more functional groups of ester, ketone or ether (i.e. —O—, —CO—, or —COO—) can also be used as a main solvent. The organic solvent may have another functional group, such as an alcoholic hydroxyl group. If the main solvent is a compound having two or more functional groups, the number of carbon atoms can be within any of the above ranges defined for the compound having any of the functional groups.

In the present invention, for a cellulose acylate film, a chlorine-containing halogenated hydrocarbon may be used as a main solvent, or a non-chlorine-containing solvent may be used as a main solvent, as described in, for example, "Kokai Giho" by Japan Institute of Invention and Innovation, 2001-1745 (pp. 12 to 16).

A solvent for the cellulose acylate solution and film of the present invention, including a dissolving method, is described, as preferred embodiments, in following patent literatures: JP-A-2000-95876, JP-A-12-95877, JP-A-10-324774, JP-A-8-152514, JP-A-10-330538, JP-A-9-95538, JP-A-9-95557, JP-A-10-235664, JP-A-12-63534, JP-A-11-21379, JP-A-10-182853, JP-A-10-278056, JP-A-10-279702, JP-A-10-323853, JP-A-10-237186, JP-A-11-60807, JP-A-11-152342, JP-A-11-292988, JP-A-11-60752 and JP-A-11-60752.

These patent literatures describe not only a solvent preferable for the cellulose acylate that can be used in the present invention but also properties of the solution and co-existence materials that are made to coexist, and constitute preferable embodiments also in the present invention.

[Optical Film]

A method of producing a film by using the cellulose acylate solution will be explained. As the method and equipment for producing the cellulose acylate film of the present invention, the same solution casting film-producing method and solution casting film producing apparatus that are used in the production of the conventional cellulose triacetate film may be used.

<Producing Process of Cellulose Acylate Film>
(Dissolution Step)

With regard to the preparation of the cellulose acylate solution (dope), there is no particular limitation to a method used to dissolve cellulose acylate. The dissolution may be carried out at the room temperature, or alternatively the dissolution may be carried out by a cooling dissolution method, a high-temperature dissolution method, or a combination of these methods. As to the preparation of the cellulose acylate solution, and the concentration and filtration of the solution associated with the dissolution step, the production processes described in detail in "Kokai Giho" by Japan Institute of Invention and Innovation Kogi No. 2001-1745, published on Mar. 15, 2001, pp. 22 to 25 are preferably used.

In the present invention, the dope transparency of the cellulose acylate solution is preferably 85% or more, more preferably 88% or more, and further preferably 90% or more. In the present invention, it can be thereby confirmed that various additives are sufficiently dissolved in the cellulose acylate dope solution. As to a specific method to calculate the dope transparency, the dope solution is injected into a glass cell which is 1 cm by 1 cm square, to measure the absorbance of the solution at a wavelength of 550 nm by using a spectrophotometer (UV-3150, trade name, manufactured by Shimadzu Corporation). The absorbance of the solvent may be measured as a control in advance, to calculate the transparency of the cellulose acylate solution from the ratio of the absorbance of the solution to that of the control.

(Casting, Drying and Winding Steps)

A dope (a cellulose acylate solution) prepared in a dissolution machine (pot) is once stored in a storage pot, and, after defoaming to remove the foams in the dope, the dope is subjected to the final preparation. The dope is discharged from a dope exhaust and fed into a pressure die via, for example, a pressure constant-rate gear pump whereby the dope can be fed at a constant flow rate at a high accuracy depending on a rotational speed. From a pipe sleeve (slit) of the pressure die, the dope is uniformly cast onto a metallic support continuously running in the casting section. At the peeling point where the metallic support has almost rounded in one cycle, the half-dried dope film (also called a web) is peeled from the metallic support. The obtained web is clipped at both ends and dried by conveying with a tenter while maintaining the width at a constant level. Subsequently, the thus-obtained web film is mechanically conveyed with rolls in a dryer, to complete the drying, followed by winding with a winder into a rolled shape in a given length. Combination of the tenter and rolls in the dryer may vary depending on the purpose. In the solvent cast film-forming method utilized to produce a silver halide photographic light-sensitive material or a functional protective film that is an optical part for electronic displays, which are major application usages of cellulose acylate films of the present invention, a coater is additionally employed in many cases, in addition to the solvent cast film-forming apparatus, so as to treat the film surface by providing, for example, an undercoat layer, an antistatic layer, an anti-halation layer or a protective layer. These production steps are described in detail in "Hatsumei Kyokai Kokai Giho" (Journal of Technical Disclosure) (Kogi No. 2001-1745, published Mar. 15, 2001, Japan Institute of Invention and Innovation), pp. 25 to 30, and they are classified into casting (including co-casting), metal supports, drying, releasing (peeling), etc., which can be preferably used in the present invention, (Stretching)

The cellulose acetate film that can be used in the present invention is preferably subjected to stretching, to adjust the retardation. In particular, when the in-plane retardation value of a cellulose acetate film is to be made a high value, use may be made of a method of positively stretching said film in the transverse direction, for example, a method of stretching the produced film, as described, for example, in JP-A-62-115035, JP-A-4-152125, JP-A-4-284211, JP-A-4-298310, and JP-A-11-48271.

Stretching of the film is carried out under the condition of the ordinary temperature or under heating. The temperature to be attained under the heating is preferably the same to or lower than the glass transition temperature of the film. The stretching of the film may be carried out by uniaxial stretching only in the longitudinal or transverse direction, or biaxial stretching in a simultaneous or successive manner. The stretching is preferably in the range of from 1 to 200%, more preferably in the range of from 1 to 100%, and particularly preferably in the range of from 1 to 50%.

In order to suppress light leakage when a polarizing plate is viewed from a slant direction, it is necessary to arrange the transmission axis of a polarizer in parallel to the in-plane slow-phase axis (retardation axis) of the cellulose acylate film. Generally, the transmission axis of a roll film-shaped polarizer which is continuously produced, is parallel to the transverse direction of the roll film. Thus, in order to apply the roll film-shaped polarizer continuously to a protective film composed of the roll film shaped cellulose acylate film to make lamination of them, it is necessary that the in-plane slow-phase axis of the roll film-shaped protective film is parallel to the transverse direction of the film. Thus, it is preferable to stretch the cellulose acylate film much in the transverse direction. Further, the stretching may be carried out in the course of the film-forming step, or a roll of raw film formed and wound may be stretched. In the former case, the film may be stretched in the condition that the film contains a residual solvent. The film can be preferably stretched when the amount of the residual solvent is 2 to 30% by mass.

The film thickness of the cellulose acylate film, that is preferably used in the present invention, obtained after drying may vary depending on the purpose of use, but it is generally in a range, preferably from 5 to 500 μm, more preferably 20 to 300 μm, and particularly preferably 30 to 150 μm. Further, the film thickness of the cellulose acylate film is preferably 40 to 110 μm, when the film is applied to optical devices, particularly VA liquid crystal displays. In order to control the thickness of the film, it is sufficient to control, for example, the concentration of the solid contained in the dope, the slit gap of a die nozzle, the extrusion pressure from the die, and the speed of the metal support, to attain a target thickness.

The width of the cellulose acylate film obtained in the above manner is preferably 0.5 to 3 m, more preferably 0.6 to 2.5 in and further preferably 0.8 to 2.2 m. The film is wound in a length of preferably 100 to 10,000 in, more preferably 500 to 7,000 m, and further preferably 1,000 to 6,000 m, per roll. When the film is wound, at least one end of the roll is preferably knurled. The width of the knurl is preferably 3 mm to 50 mm, and more preferably 5 mm to 30 mm, and the height of the knurl is preferably 0.5 to 500 μm, and more preferably 1 to 200 μm. The film may be knurled on one side or both sides.

The dispersion (scattering) of a Re(590) value in the transverse direction of the film is preferably ±5 nm, and more preferably ±3 nm. Also, the dispersion of a Rth(590) value in the transverse direction is preferably ±10 nm, and more preferably ±5 nm. Further, each dispersion of Re value and Rth value in the longitudinal direction is preferably within the same range as to that of the dispersion in the transverse direction, <Optical Performances of Cellulose Acylate Film>

Herein, in the present specification, the Re($\lambda$) and the Rth($\lambda$) indicate the in-plane retardation and the retardation in the direction of the thickness, respectively, at the wavelength $\lambda$ (nm). The Re($\lambda$) can be measured by making light of wavelength $\lambda$ nm incident in the direction of the normal of the film, in KOBRA 21ADH (trade name, manufactured by Oji Scientific Instruments). The Rth($\lambda$) is a value that can be calculated by KOBRA 21ADH based on: (i) the retardation values measured in total three directions, these retardation values including the above Re($\lambda$), the retardation value measured by allowing light of wavelength $\lambda$ nm to be incident from a direction inclined at an angle of +40° with the direction of the normal of the film by adopting the slow phase axis (which is determined by the KOBRA 21ADH) in the plane as a slant axis (rotation axis), and the retardation value measured by allowing light of wavelength $\lambda$ nm to be incident from a direction inclined at an angle of −40° with the direction of the normal of the film by adopting the slow phase axis in the plane as a slant axis (rotation axis); (ii) an hypothetical value of the average refractive index; and (iii) a film thickness input.

Herein, as the hypothetical value of the average refractive index, use may be made, for example, of values described in "Polymer Handbook" (JOHN WILEY & SONS, INC.) and values described in catalogues of various optical films. Unknown average refractive indexes may be determined by Abbe refractometer. Average refractive indexes of major optical films are exemplified in below: cellulose acylate (1.48), cycloolefin polymer (1.52), polycarbonate (1.59), polymethyl methacrylate (1.49), and polystyrene (1.59). KOBRA 21ADH can calculate nx, ny, and nz, by inputting these hypothetical values of the average refractive index and the film thickness.

It is preferable that the Re($\lambda$) retardation value and the Rth($\lambda$) retardation value satisfy the following expressions (7) and (8), respectively, to widen the angle of field of view of a liquid crystal display, particularly a VA or OCB mode liquid crystal display. Further, this is particularly preferable when the cellulose acylate film is used for the protective film on the liquid crystal cell side of the polarizing plate.

$$0 \text{ nm} \leq Re(590) \leq 200 \text{ nm} \quad \text{Expression (7)}$$

$$0 \text{ nm} \leq Rth(590) \leq 400 \text{ nm} \quad \text{Expression (8)}$$

In the above expressions, Re(590) and Rth(590) each are a value (unit: nm) measured at wavelength of 590 nm.

It is preferable that the Re($\lambda$) retardation value and the Rth($\lambda$) retardation value satisfy the following expressions (7-1) and (8-1), respectively.

$$30 \text{ nm} \leq Re(590) \leq 150 \text{ nm} \quad \text{Expression (7-1)}$$

$$30 \text{ nm} \leq Rth(590) \leq 300 \text{ nm} \quad \text{Expression (8-1)}$$

When the cellulose compound film that is preferably used in the present invention is used in a VA or OCB mode, there are two types of structures: a structure (two-film type) in which the film is applied to each side of a cell, i.e. the total two films are utilized; and a structure (one-film type) in which the film is applied only one side of a cell.

In the case of the two-film type, the Re(590) is preferably 20 to 100 nm, more preferably 30 to 70 nm; and the Rth(590) is preferably 70 to 300 nm, more preferably 100 to 200 nm.

In the case of the one-film type, the Re(590) is preferably 30 to 150 nm, more preferably 40 to 100 nm; and the Rth(590) is preferably 100 to 300 nm, more preferably 150 to 250 nm.

<Moisture Permeability of Film>

The moisture permeability of a cellulose acylate film of the present invention to be used for an optical compensation sheet is preferably 400 to 2,000 g/m$^2$·24 h, more preferably 500 to 1,800 g/m$^2$·24 h, and particularly preferably 600 to 1,600 g/m$^2$·24 h, based on the case where the film thickness be 80 μm in measurement under the conditions of temperature 60° C. under humidity 95% RH (relative humidity) according to JIS Standard, JIS Z0208. Adjusting the moisture permeability to 2,000 g/m$^2$·24 h or less is preferable, because the absolute values of the Re value and Rth value of the film, which values are humidity dependent, hardly exceed 0.5 nm/% RH. In addition, when an optical compensation film is made by laminating an optical anisotropic layer on the cellulose acylate film of the present invention, the absolute values of the Re value and Rth value of the film, which values are humidity dependent, hardly exceed 0.5 nm/% RH, which is preferable. When this optical compensation sheet or polarizing plate is assembled into a liquid crystal display, it hardly causes transformation of color hue or deterioration in the angle of field of view. Further, by adjusting the moisture permeability of the cellulose acylate film to 400 g/m$^2$·24 h or more, an adhesive is inhibited from being dried due to the cellulose acylate film, thereby hardly resulting in inferior adhesion, when, for example, the cellulose acylate film is applied to each side of the polarizing film to make a polarizing plate.

If the film thickness of the cellulose acylate film is thick, the moisture permeability becomes small, whereas if the film thickness is thin, the moisture permeability becomes large. Therefore, in the present invention, the moisture permeability is described as a corresponding value based on that of a standard sample of thickness 80 μm. The conversion of the film thickness is made according to the following equation:

(Moisture permeability converted to thickness 80 μm)=(Measured moisture permeability)×(Measured film thickness μm/80 μm)

As a method of measuring the moisture permeability, the method described in "Properties of Polymers II" (Polymer Experiment Lesson 4, Kyoritsu Shuppan), pp. 285 to 294: Measurement of Amount of Vapor Transmission (Mass method, Temperature gauge method, Vapor pressure method, and Adsorption amount method), may be applied. That is, a 70 mmϕ cellulose acylate film sample according to the present invention is humidity-controlled at 25° C. under humidity 90% RH and at 60° C. under humidity 95% RH, respectively for 24 hours, to measure the amount of water per unit area (g/m$^2$), by using a moisture permeability tester (trade name: KK-709007, manufactured by Toyo Seiki Seisaku-sho, Ltd.), according to JIS Z-0208, and then the moisture permeability is calculated from the following equation:

(Moisture permeability)=(Mass after moisture control)−(Mass before moisture control).

<Amount of Residual Solvent in Film>

In the present invention, it is preferable to dry the cellulose acylate film in the condition that the amount of a residual solvent is decreased to an amount range from 0.01 to 1.5% by mass, more preferably 0.01 to 1.0% by mass, to the cellulose acylate film. In the case that the cellulose acylate film of the present invention is used as a support, when the amount of a residual solvent is set to the above-mentioned range, curling can be effectively suppressed or prevented. This is assumed to be based on that the amount of a residual solvent may be reduced upon the film formation by the aforementioned solvent-casting method, leading to a reduced free volume, which would be a main factor of the effect.

[Coefficient of Hygroscopic Swelling of Film]

The coefficient of hygroscopic swelling (expansion) of the cellulose acylate film is preferably 30×10$^{-5}$/% RH or less, more preferably 15×10$^{-5}$/% RH or less, and further preferably 10×10$^{-5}$/% RH or less. The lower limit is not particularly defined, but smaller the hygroscopic expansion coefficient tends to be preferable, and a value of 1.0×10$^{-5}$/% RH or more is more preferable. The coefficient of hygroscopic swelling indicates an amount of change in the length of a sample when relative humidity is changed under a fixed temperature condition. By controlling the coefficient of the hygroscopic swelling, the cellulose acylate film of the present invention can be used as an optical compensation film support, while maintaining the optical compensation function of the optical compensation film, and with preventing an architrave-like (or frame-like) rise in transmission, i.e. light leakage due to strain.

<Surface Treatment>

A cellulose acylate film may be subjected to a surface treatment, if necessary, in order to achieve enhanced adhesion between the cellulose acylate film and each functional layer (e.g., subbing or undercoat layer, and backing layer). For example, a glow discharge treatment, an ultraviolet ray treatment, a corona discharge treatment, a flame treatment, an acid treatment, and an alkali treatment may be applied. The glow discharge treatment referred to herein may be a treatment with low-temperature plasma (thermal plasma) generated in a low-pressure gas having a pressure of 10$^{-3}$ to 20 Torr (0.133 Pa to 2.67 kPa), or preferably with plasma under the atmospheric pressure. A plasma excitation gas is a gas which can be excited to plasma under conditions as described above, and examples thereof include argon, helium, neon, krypton, xenon, nitrogen, carbon dioxide, flons such as tetrafluoromethane, and a mixture thereof. Details thereof are described in "Hatsumei Kyokai Kokai Giho" (Kogi No. 2001-1745, published Mar. 15, 2001, Japan Institute of Invention and Innovation), pp. 30 to 32, which detailed techniques can be preferably used in the present invention.

<Alkali Saponifying Treatment>

The alkali saponifying treatment is preferably conducted, by directly immersing the cellulose acylate film into a bath of a saponifying solution, or by applying a saponifying solution onto the cellulose acylate film. Examples of the application method include a dip coating method, a curtain coating method, an extrusion coating method, a bar coating method, and an E-type coating method. As the solvent in the alkali saponifying treatment coating solution, it is preferable to employ a solvent which has an excellent wettability appropriate for applying the saponifying solution to a cellulose acylate film, and which can hold a favorable surface state without forming any irregularity on the cellulose acylate film surface due to the saponifying solution solvent. More specifically speaking, it is preferable to use an alcoholic solvent, and isopropyl alcohol is particularly preferable therefor. It is also possible to employ an aqueous solution of a surfactant as the solvent. As the alkali in the alkali saponifying solution, it is preferable to use an alkali soluble in the above-described solvent, and KOH or/and NaOH is further preferable therefor. It is preferable that the saponifying (coating) solution has a pH value of 10 or more, more preferably 12 or more. Concerning the reaction conditions, it is preferable to perform the alkali saponification at room temperature for 1 second or longer but 5 minutes or shorter, more preferably for 5 seconds or longer but 5 minute or shorter, and particularly preferably for 20 seconds or longer but 3 minutes or shorter. After the completion of the alkali saponification reaction, it is preferable to wash with water; or wash with an acid and then wash with water, the face coated with the saponifying solution.

<Functional Layers>

The cellulose acylate film of the present invention can be applied to optical articles or to photographic photosensitive materials, as the usage applications. Particularly, it is preferred that the optical article is a liquid crystal display. Further, it is more preferable that the liquid crystal display has a configuration wherein a liquid crystal cell carrying a liquid crystal between two sheets of electrode substrates, two sheets of polarizers disposed at both sides of the liquid crystal cell one by one, and at least one optical compensating sheet disposed between the liquid crystal cell and the polarizer. As these liquid crystal displays, TN (Twisted Nematic), IPS (In-Plane Switching), FLC (Ferroelectric Liquid Crystal), AFLC (Anti-ferroelectric Liquid Crystal), OCB (Optically Compensatory Bend), STN (Supper Twisted Nematic), ECB (Electrically Controlled Birefringence), VA (Vertically Aligned), and HAN (Hybrid Aligned Nematic) are preferable.

When the cellulose film of the present invention is used for the aforementioned optical articles, any of various kinds of functional layers may be provided on the film. Examples of the functional layer include an antistatic layer, a hardened resin layer (transparent hard coat layer), an anti-reflection layer, an enhanced-adhesion layer, an anti-glare layer, an optical compensating layer, an orientating layer, and a liquid crystal layer. As the functional layer and material therefor, which may be used in the cellulose film of the present invention, a surface-active agent, a sliding agent, a matting agent, an anti-static layer, and a hard-coat layer are enumerated, details of which are described in "Kokai Giho of Japan Institute of Invention & Innovation" (Kogi No. 2001-1745, published on Mar. 15, 2001), pp. 32 to 45, which can be preferably used.

[Polarizing Plate]

The usage applications of the cellulose film of the present invention are described below.

The cellulose film of the present invention is particularly useful for a polarizing plate protective film. When the film is used for a polarizing plate-protective film, the production method of polarizing plate is not particularly limited, but the polarizing plate may be produced in a usual manner. For example, there is a method of producing a polarizing plate, comprising the steps of: alkali-treating the obtained cellulose film; and sticking, with using an aqueous solution of completely saponificated polyvinyl alcohol, the alkali-treated film one by one onto each side of a polarizing film produced by dipping a polyvinyl alcohol film in an iodine solution, followed by stretching. In place of the alkali treatment, an enhanced adhesion processing, as described in JP-A-6-94915 and JP-A-6-118232, may be adopted to the aforementioned production method.

Examples of the adhesive that can be used in adhering the treated side of the protective film and the polarizing film, include polyvinyl alcohol-series adhesives, such as polyvinyl alcohol and polyvinyl butyral; and vinyl-series latexes, such as butyl acrylate.

A polarizing plate is generally composed of a polarizing film and protecting films to protect both surfaces of the polarizing film, and the thus-prepared polarizing plate may be further provided with a protect film stuck to one surface of the polarizing plate, and a separation film stuck to the opposite surface of the polarizing plate. The protect film and the separation film are used, in order to protect the polarizing plate when the polarizing plate is shipped and subjected to a product testing or the like. In this case, the protect film is stuck in order to protect the surface of a polarizing plate, and the film is used at the side of the surface opposite to the surface with which the polarizing plate is stuck to a liquid crystal plate. Meanwhile, the separation film is used to cover an adhesive layer to be stuck to the liquid crystal plate, and the film is used at the same side as the surface with which the polarizing plate is stuck to a liquid crystal plate.

In a liquid crystal display, usually, a substrate containing liquid crystals is disposed between two polarizing plates. A polarizing-plate protective film to which the cellulose film of the present invention is applied can exhibit excellent display performances, regardless of the site the film is to be disposed. In particular, because a transparent hard coat layer, an anti-glare layer, an anti-reflection layer, and the like layers are disposed to a polarizing-plate protective film to be disposed at the outermost surface at the displaying side of a liquid crystal display, employment of the aforementioned polarizing-plate protective film at this site is especially preferable.

[Optical Compensation Film (Phase Difference Plate)]

The cellulose acylate film of the present invention can be utilized in various usage applications. It is especially effective when the cellulose acylate film is used as an optical compensation film for liquid crystal display. Herein, the optical compensation film means an optical material that is generally used in a liquid crystal display to compensate a phase difference, and that has the same meaning, for example, as a phase difference plate and an optical compensation sheet. The optical compensation film has birefringence characteristics, and can be used for the purpose of eliminating coloring on the displaying plane of a liquid crystal display or improving the characteristics of the angle of field of view.

[Liquid Crystal Display]

<Constitution of Generally Liquid Crystal Display>

When the cellulose film is used for an optical compensation film, the transmission axis of the polarizing film and the slow phase axis of the optical compensation sheet composed of the cellulose film can be arranged at any angle. A liquid crystal display has a constitution of a liquid crystal cell carrying liquid crystal between two pieces of electrode substrates, two polarizing films disposed on both surfaces of the liquid crystal cell, and at least one optical compensation film disposed between the liquid crystal cell and the polarizing film.

The liquid crystal layer of the liquid crystal cell is generally formed by sealing a liquid crystal, in the space made by putting a spacer sandwiched between two pieces of substrates. The transparent electrode layer can be formed, for example, on the substrate as a transparent film containing an electric conductive substance. To the liquid crystal cell, for example, a gas barrier layer, a hard coat layer, or an undercoat (or subbing) layer (used for adhesion of the transparent electrode layer) may be further provided. The aforementioned layers can be provided on the substrate. It is preferable that the thickness of the substrate for the liquid crystal cell is generally from 50 µm to 2 mm.

<Kinds of Liquid Crystal Displays>

The cellulose film of the present invention can be applied to liquid crystal cells of various display modes. As for the display modes, proposed are various modes, for example, TN, IPS, FLC, AFLC, OCB, STN, VA, ECB, and HAN. In addition, the cellulose film can be also used for display modes that are obtained by orientation dividing of the aforementioned display modes. Further, the cellulose film of the present invention can be preferably used in any of transparent-type, reflection-type, and semitransparent-type liquid crystal displays.

(TN-Type Liquid Crystal Display)

The cellulose film of the present invention can be used as a support for an optical compensation sheet that is used in TN type liquid crystal displays having the liquid crystal cell of TN mode. The TN mode liquid crystal cell and the TN-type liquid crystal display per se are well known for a long time. The optical compensation sheet that is used in TN-type liquid crystal displays can be prepared in accordance with the method described in, for example, JP-A-3-9325, JP-A-6-148429, JP-A-8-50206, and JP-A-9-26572, and also described in, for example, papers authored by Mori, et al. (Jpn. J. Appl. Phys., Vol. 36 (1997), p. 143, and Jpn. J. Appl. Phys., Vol. 36 (1997), p. 1068).

(STN-Type Liquid Crystal Display)

The Cellulose Film of the Present Invention May be Used as a Support for an Optical Compensation sheet that is employed in STN-type liquid crystal displays installing a STN mode liquid crystal cell. In STN-type liquid crystal displays, generally, cylindrical shape liquid crystal molecules in the liquid crystal cell is twisted in the range of 90 to 360 degrees, and the product (Δnd) of the refractive index anisotropy (Δn) and cell gap (d) of the cylindrical shape liquid crystal molecular is in the range of 300 to 1,500 nm. Regarding optical compensation sheets used for the STN type liquid crystal display, it can be prepared in accordance with the method described in JP-A-2000-105316.

(VA-Type Liquid Crystal Display)

The Cellulose Film of the Present Invention can be Particularly Advantageously Used as a Support for an optical compensation sheet that is used in the VA-type liquid crystal displays installing a VA mode liquid crystal cell. It is preferred that the Re retardation value is controlled to the range of from 0 to 150 nm and the Rth retardation value is controlled to the range of from 70 to 400 nm, respectively, for the optical compensation sheet that is used in the VA-type liquid crystal display. In an embodiment where two sheets of optically anisotropic polymer films are used in a VA-type liquid crystal display, it is preferred that the Rth retardation value of the film is in the range of from 70 to 250 nm. In an embodiment where one sheet of an optically anisotropic polymer film is used in a VA-type liquid crystal display, it is preferred that the Rth retardation value of the film is in the range of from 150 to 400 nm. The VA-type liquid crystal display may have an orientation dividing system, as described in, for example, JP-A-10-123576.

(IPS-Type Liquid Crystal Display and ECB-Type Liquid Crystal Display)

The cellulose film of the present invention may also be advantageously used as the support for the optical compensation sheet or as the protective film of the polarizing plate, in an IPS-type liquid crystal display or ECB-type liquid crystal display in which an IPS-mode or ECB-mode liquid crystal cell is assembled. In these modes, a mesomorphism (liquid crystal) material is oriented almost in parallel when a black color is displayed, and a mesomorphism molecule is oriented in parallel to the surface of the substrate in the condition that no voltage is applied, to display a black color. In these modes, the polarizing plate using the cellulose film of the present invention contributes to improvement in color hue, expansion of the angle of field of view, and improvement in contrast. In these modes, it is preferable that use is made of, for at least one side of the two polarizing plates, a polarizing plate in which the cellulose film of the present invention is used for the protective film (a cell-side protective film) disposed between the liquid crystal cell and the polarizing plate, of the protective films of the above polarizing plates on the upper and lower sides of the liquid crystal cell. It is more preferable that an optical anisotropic layer be disposed between the protective film of the polarizing plate and the liquid crystal cell, and that the retardation value of the disposed optical anisotropic layer be set to a value not more than twice the value of Δn·d of the liquid crystal layer.

(OCB-Type Liquid Crystal Display and HAN-Type Liquid Crystal Display)

The Cellulose Film of the Present Invention can Also be Advantageously Used as a Support for an optical compensation sheet that is used in an OCB-type liquid crystal display having a liquid crystal cell of OCB mode, or used in a HAN-type liquid crystal display having a liquid crystal cell of HAN mode. It is preferable that, in the optical compensation sheet used for an OCB-type liquid crystal display or a HAN-type liquid crystal display, the direction where the magnitude or absolute value of retardation becomes the minimum value exists neither in the optical compensation sheet plane nor in its normal direction. Optical properties of the optical compensation sheet for use in the OCB type liquid crystal display or the HAN type liquid crystal display are also determined by the optical properties of the optical anisotropy layer, by the optical properties of the support, and by the arrangement of the optical anisotropy layer and the support. JP-A-9-197397 describes, regarding the optical compensation sheet for use in the OCB type liquid crystal display or HAN type liquid crystal display. In addition, in accordance with the method described in a paper by Mori et al. (Jpn. J. Appl. Phys., Vol. 38 (1999), p. 2837), it can be prepared.

(Reflection-Type Liquid Crystal Display)

The cellulose film of the present invention can also be advantageously used as an optical compensation sheet for the reflection-type liquid crystal displays of TN-type, STN-type, HAN-type, or GH (Guest-host)-type. These display modes are well known for a long time. The TN-type reflection-type liquid crystal displays can be prepared in accordance with the method described in, for example, JP-A-10-123478, WO 98/48320, and Japanese Patent No. 3022477. The optical compensation sheet for use in a reflection type liquid crystal display can be prepared in accordance with the method described in, for example, WO 00/65384.

(Other Liquid Crystal Displays)

The cellulose film of the present invention can also be advantageously used as a support for an optical compensation sheet for use in ASM (Axially Symmetric Aligned Microcell) type liquid crystal displays having a liquid crystal cell of ASM mode. The liquid crystal cell of ASM mode is characterized in that a resin spacer adjustable with its position maintains the thickness of the cell. Other properties of the liquid crystal cell of ASM mode are similar to the properties of the liquid crystal cell of TN mode. Liquid crystal cells of ASM mode and ASM type liquid crystal displays can be prepared in accordance with the method described in a paper of Kume et al. (Kume et al., SID 98 Digest 1089 (1998)).

<Hardcoat Film, Antiglare Film, and Antireflection Film>

The cellulose film of the present invention may also be preferably applied to a hardcoat film, an antiglare film, and an antireflection film. Any or all of the hardcoat layer, antiglare layer and antireflection layer may be provided on one or both surfaces of the cellulose film of the present invention, for the purposes of improving the visibility of the flat panel displays of LCDs, PDPs, CRTs, ELs, and the like. Preferable embodiments of the antiglare film or antireflection film are described in detail in Japan Institute of Invention and Innovation, "Kokai Giho" Kogi No. 2001-1745, published on Mar. 15, 2001, pp. 54 to 57. The cellulose film of the present invention can be preferably used in these embodiments.

<Photographic Film Support>

The cellulose film of the present invention may be applied as a support of a silver halide photographic photosensitive material. Specifically, in accordance with the techniques concerning color negatives described in JP-A-2000-105445, the cellulose film of the present invention can be preferably used in the aforementioned color negatives. Further, the cellulose film is also preferably applied as the support of a color reversal silver halide photographic photosensitive material, and in accordance with various raw materials, formulations, and processing or treating methods, as described in JP-A-11-282119, it can be prepared.

<Transparent Substrate>

Since the cellulose film of the present invention is close to zero in the optical anisotropy and can have excellent transparency, the cellulose acylate film may be used in place of a liquid crystal cell glass substrate of a liquid crystal display, i.e. it may be used as a transparent substrate that seals a driving liquid crystal.

Because it is necessary that the transparent substrate that seals a liquid crystal be excellent in gas barrier properties, the cellulose film of the present invention may be provided with a gas barrier layer on the surface thereof, if necessary. There is no particular limitation on the shape and material of the gas barrier layer. Specifically, any of the following methods may be given, in which, on at least one of the surfaces of the cellulose film of the present invention, $SiO_2$ or the like is vapor-deposited, or a coating layer of a polymer, such as a vinylidene chloride-series polymer or vinyl alcohol-series polymer, which is relatively high in gas barrier properties, is formed. Any of these methods may be appropriately used in the present invention.

Further, when the cellulose film is used as a transparent substrate that seals a liquid crystal, it may be provided with a transparent electrode(s) to drive the liquid crystal by applying voltage. There is no particular limitation on the transparent electrode, but a metal film, metal oxide film or the like may be laminated, to thereby form the transparent electrode(s), on at least one of the surfaces of the cellulose film of the present invention. Of those, a film of a metal oxide is preferable, from the viewpoints of transparency, electrical conductivity, and mechanical characteristics. In particular, a thin film of indium oxide containing tin oxide primarily and 2 to 15 mass % of zinc oxide, can be preferably used. The details of these techniques are disclosed in, for example, JP-A-2001-125079 and JP-A-2000-227603.

In order to control the Re value and Rth value of the cellulose film of the present invention to be each within the preferable ranges, it is preferable to properly control the type and amount to be added of the compound represented by formula (I) or (II) (herein, which may also be referred to as a retardation controlling agent), as well as a stretching ratio of the film. In the present invention, particularly, among the compounds represented by formula (I) and (II), a suitable retardation-controlling agent capable of attaining a desired Rth value is selected, and the amount of the retardation-controlling agent to be added and the stretching ratio of the film each are properly set, to thereby control the Re value in the target range; and thus a cellulose film having a desired Re value and Rth value can be obtained.

The compound of the present invention can provide a film with reverse wavelength dispersion when the compound is added to a film. Also, an optical film containing the compound of the present invention has reverse wavelength dispersion, so a phase difference plate composed of the optical film is useful as a λ/4 plate and can preferably be applied to a liquid crystal display.

The present invention will be described in more detail based on the following examples. The materials, the amounts to be used, the proportions, the contents and procedures of treatment or processing, which will be shown in the examples, may be appropriately changed or modified, without departing from the spirit of the present invention. Therefore, the following examples are not interpreted as limiting of the scope of the present invention.

EXAMPLES

Example 1

Synthesis of Exemplified Compound (1)

The Exemplified compound (1) was synthesized, according to the following scheme.

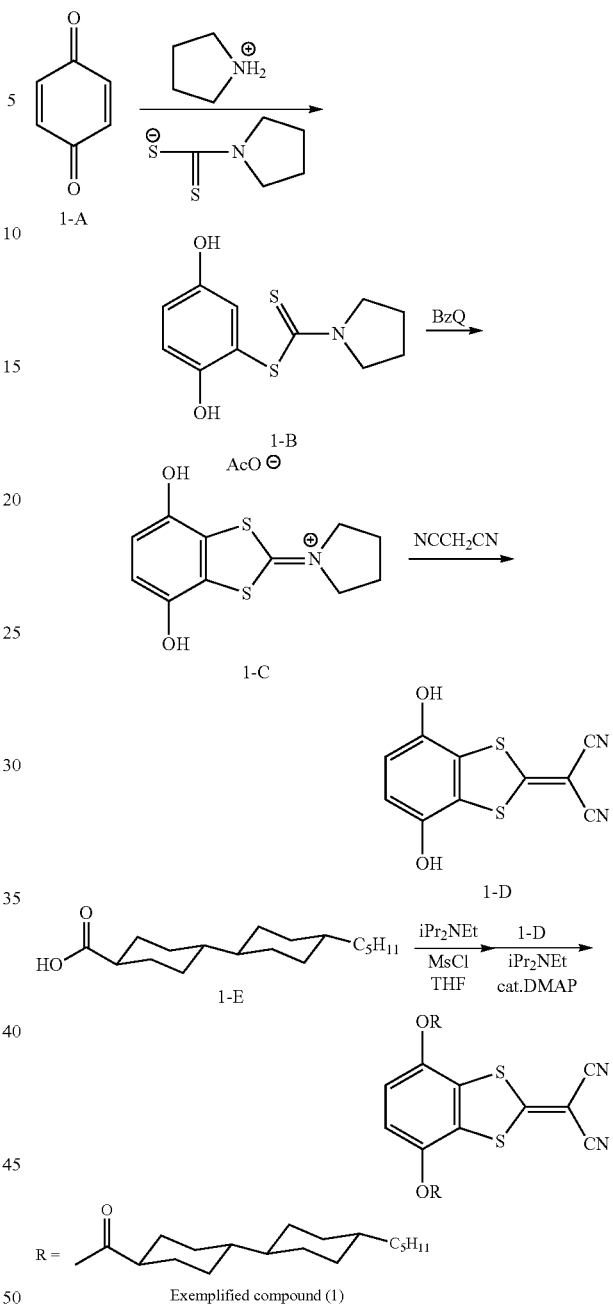

The synthesis of each of compounds (1-A) to (1-D) was carried out by the methods described in "Journal of Chemical Crystallography" (1997); 27(9); p. 515-526.

To 100 ml of a tetrahydrofuran (THF) solution containing 12.34 g (44 mmol) of the compound (1-E) (manufactured by Yantai valiant Fine Chem.), added was 3.4 ml (44 mmol) of methansulfonic acid chloride, under ice-cooling, and to the resultant mixture, added slowly, dropwise, was 8.05 ml (46.2 mmol) of N,N-diisopropylethylamine. After the resultant mixture was stirred for one hour, to the mixture, 8.05 ml (46.2 mmol) of N,N-diisopropylethylamine was added, and then 50 ml of a tetrahydrofuran solution containing 4.97 g of the compound (1-D) was added dropwise. Then, to the mixture, 20 ml of a tetrahydrofuran solution containing 0.05 g of N,N-dimethylaminopyridine (DMAP) was added dropwise, followed by stirring under ice-cooling for one hour, then raising to the room temperature, and further stirring for 6 hours. And then, ethyl acetate and water were added to the mixture, to separate an organic phase. The organic phase was washed with water, 1-N aqueous hydrochloric acid and water, in this order, and then dried over magnesium sulfate, and then the solvents were distilled off under reduced pressure. The resultant was purified by a silica gel column chromatography using a methylene chloride/methanol mixture solvent as an eluting solution, thereby obtaining 5.6 g of the exemplified compound (1) (72 mol % in yield).

Examples 2, 3 and 4

Syntheses of Exemplified Compounds (2), (3), and (4)

The exemplified compounds (2), (3) and (4) were synthesized in the same manner as in Example 1, except that, instead of 4-(trans-4-pentylcyclohexyl)cyclohexane carboxylic acid, 4-(trans-4-butylcyclohexyl)cyclohexane carboxylic acid, 4-(trans-4-propylcyclohexyl)cyclohexane carboxylic acid, or 4-(trans 4-ethylcyclohexyl)cyclohexane carboxylic acid was used.

Example 5

Synthesis of Exemplified Compound (16)

The exemplified compound (16) was synthesized, according to the following scheme.

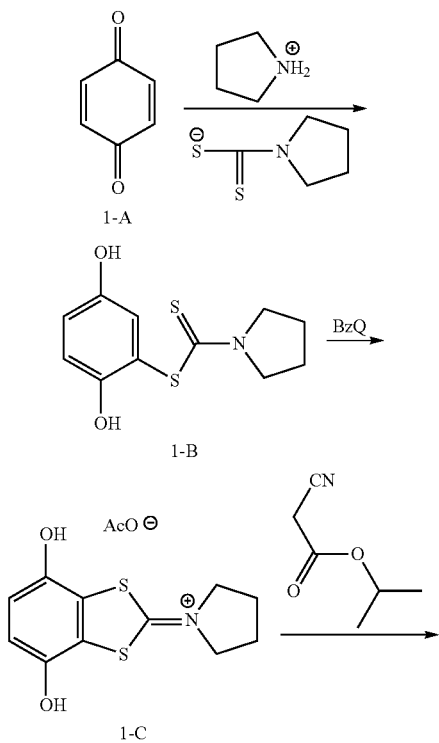

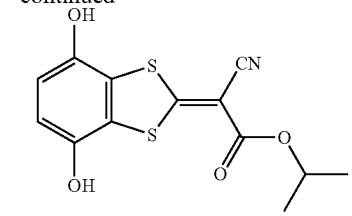

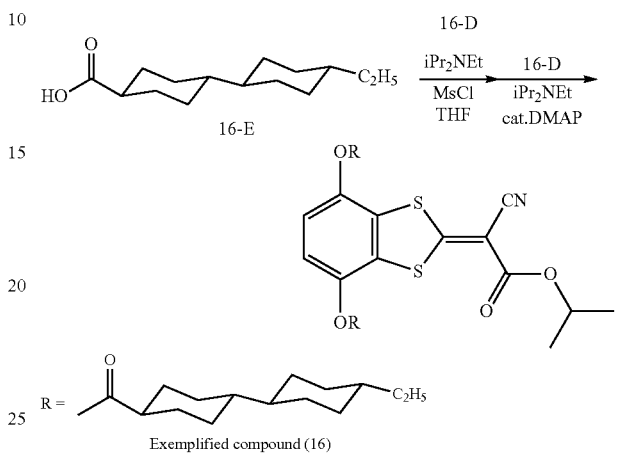

Exemplified compound (16)

The synthesis of each of compounds (1-A) to (1-C) was carried out by the methods described in "Journal of Chemical Crystallography" (1997); 27(9); p. 515-526.

To 500-ml of a N-methylpyrrolidone solution containing 62.7 g (0.2 mol) of the compound (1-C), 30 ml (0.24 mol) of cyanoacetic acid isopropyl ester was added, and the mixture was stirred for 5 hours at an inner temperature of 120° C. After cooling down, ethyl acetate and water were added thereto, to give an organic layer. The organic layer was washed with water and dried over magnesium sulfate, and the solvents were distilled off under reduced pressure, to give a solid. The solid was dispersed in an acetone/hexane mixture solvent and filtration was then repeated two times, thereby obtaining 58.0 g of the compound (16-D) (93 mol % in yield).

To 100 ml of a tetrahydrofuran (THF) solution containing 10.49 g (44 mmol) of the compound (16-E) (manufactured by Yantai valiant Fine Chem.), added was 3.4 ml (44 mmol) of methansulfonic acid chloride, under ice-cooling, and to the resultant mixture, added slowly, dropwise, was 8.05 ml (46.2 mmol) of N,N-diisopropylethylamine. After the resultant mixture was stirred for one hour, to the mixture, 8.05 ml (46.2 mmol) of N,N-diisopropylethylamine was added, and then 50 ml of a tetrahydrofuran solution containing 6.19 g (20 mmol) of the compound (16-D) was added dropwise. Then, to the mixture, 20 ml of a tetrahydrofuran solution containing 0.05 g of N,N-dimethylaminopyridine (DMAP) was added dropwise, followed by stirring under ice-cooling for one hour, then raising to the room temperature, and further stirring for 6 hours. And then, ethyl acetate and water were added to the mixture, to separate an organic phase. The organic phase was washed with water, 1-N aqueous hydrochloric acid and water, in this order, and then dried over magnesium sulfate, and then the solvents were distilled off under reduced pressure. The resultant was purified by a silica gel column chromatography using a methylene chloride/methanol mixture solvent as an eluting solution, thereby obtaining 5.4 g of the exemplified compound (16) (36 mol % in yield).

Example 6

Synthesis of Exemplified Compound (20)

The exemplified compound (20) was synthesized in the same manner as in Example 5, except that, instead of cyanoacetic acid isopropyl ester, cyanoacetic acid 3-methoxybutyl ester was used.

Example 7

Synthesis of Exemplified Compound (49)

The exemplified compound (49) was synthesized, according to the following scheme

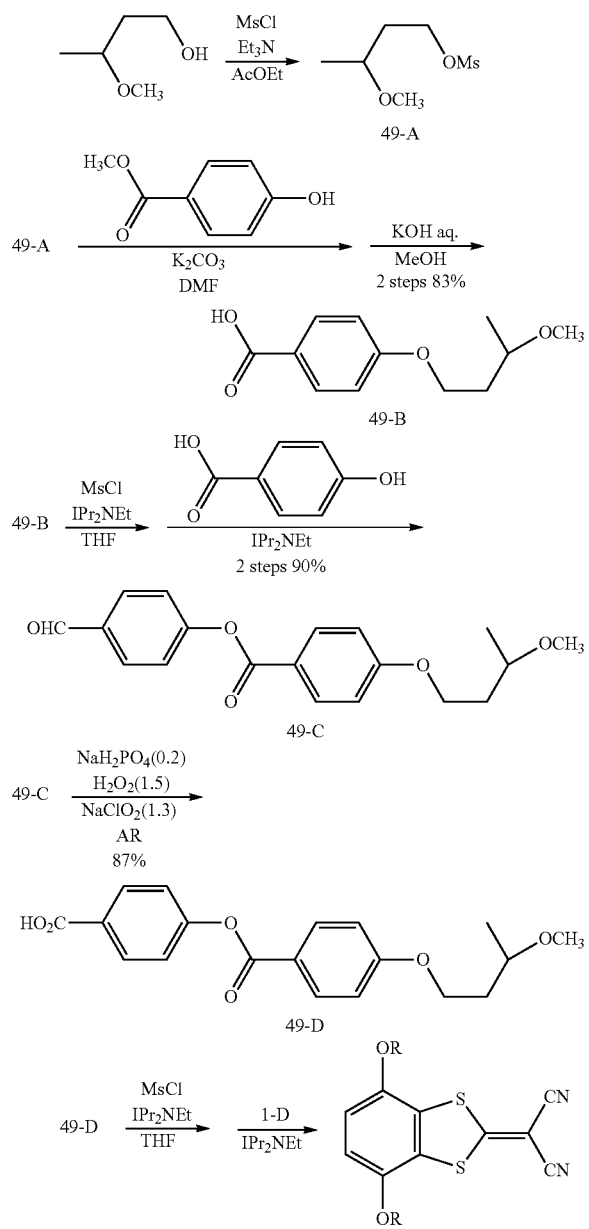

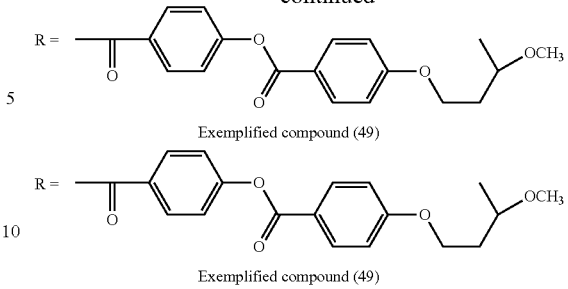

Exemplified compound (49)

Exemplified compound (49)

To an ethyl acetate solution containing 200 g (1.92 mol) of 3-methoxy-1-butanol, added was 185 g (1.83 mol) of triethylamine. After the reaction system was cooled to 2° C., 209 g (1.83 mol) of methanesulfonic acid chloride was added dropwise to the reaction system, while the temperature of the reaction system was kept at 15° C. or lower. After the dropwise addition was completed, the reaction system was stirred at 10° C. or lower for 30 minutes, and then the temperature of the reaction system was raised to the room temperature, followed by stirring for 3 hours. Water was added thereto, to separate the reaction solution, and the separated organic phase was washed with water, 1-N aqueous hydrochloric acid, and water, in this order. The resulting organic phase was dried over magnesium sulfate, and the solvents were distilled off under reduced pressure, to obtain 292.2 g of a crude compound (1-A) (yield 88 mol %).

To 1,600 ml of an N,N-dimethylformamide (DMF) solution containing 60 g (0.394 mol) of methyl parahydroxybenzoate, added was 70.8 g (0.512 mol) of potassium carbonate, and to the resultant mixture, added was 89 g (0.488 mol) of the compound (49-A). The temperature of the reaction system was raised to 100° C., followed by stirring for 6 hours. After the reaction was finished, the system was cooled. To the thus-cooled system, 1 L of ethyl acetate and water were added, to separate the resultant solution. The separated organic phase was washed with water, 1-N aqueous hydrochloric acid, and water, in this order. The organic phase was dried over magnesium sulfate, and the solvents were distilled off under reduced pressure. To the resultant crude product, 85 ml of methanol was added, and 240 ml of an aqueous solution containing 66.4 g (1.182 mol) of potassium hydroxide was added dropwise to the mixture. The reaction system was heated to 50° C., followed by stirring for 4 hours at that temperature. The completion of the reaction was confirmed by TLC, and the reaction system was cooled to 5° C. The reaction solution was slowly added dropwise to 1 L of 1-N aqueous hydrochloric acid cooled to 5° C. The thus-produced crystals were collected by filtration, and dried, to obtain 73.4 g of a compound (49-B) (yield 83 mol %).

To 500 ml of a tetrahydrofuran (THF) solution containing 50 g (0.223 mol) of the compound (49-B), added was 17.3 ml (0.224 mol) of methansulfonic acid chloride, under ice-cooling, and to the resultant mixture, added slowly, dropwise, was 40 ml (0.230 mol) of N,N-diisopropylethylamine. After the resultant mixture was stirred for one hour, 100 ml of a tetrahydrofuran solution containing 30.2 g (0.247 mol) of parahydroxybenzaldehyde, and 40 ml (0.230 mol) of N,N-diisopropylethylamine were added dropwise to the mixture. Then, to the mixture, 100 ml of a tetrahydrofuran solution containing 0.2 g of N,N-dimethylaminopyridine was added dropwise, followed by stirring under ice-cooling for one hour, then raising to the room temperature, and further stirring for 6 hours. To the reaction solution, water was added, to separate the solution, and the separated organic phase was washed with water, 1-N aqueous hydrochloric acid, and water, in this order. The resultant organic phase was dried over magnesium sulfate, and the solvents were distilled off under reduced pressure, to obtain 66 g of a crude compound (49-C) (yield 90 mol %).

Two hundred milliliters of an acetonitrile solution containing 43 g (0.13 mol) of the compound (49-C) was cooled to 10° C., and thereto 25 ml of an aqueous solution containing 4.21 g (0.027 mol) of sodium dihydrogenphosphate was added dropwise, and then 23 ml (0.195 mol) of a 30% aqueous hydrogen peroxide was added dropwise. To the mixture, 125 ml of an aqueous solution containing 15.9 g of sodium chlorite was slowly added dropwise. The temperature of the reaction system was raised to 50° C., followed by stirring for 3 hours. The completion of the reaction was confirmed by TLC, and the reaction system was cooled to 10° C. The reaction solution was slowly added dropwise to 1.5 L of 1-N aqueous hydrochloric acid cooled to 5° C. The thus-produced crystals were collected by filtration, and dried, to obtain 38.8 g of a compound (49-D) (yield 87 mol %).

To 430 ml of a tetrahydrofuran (TFH) solution containing 30 g (88 mmol) of the compound (49-D), added was 6.8 ml (88 mmol) of methanesulfonyl chloride, under ice-cooling, and to the resultant mixture, added slowly, dropwise, was 17 ml (97 mmol) of N,N-diisopropylethylamine. After the resultant mixture was stirred for one hour, to the mixture, 17 ml (97 mmol) of N,N-diisopropylethylamine was added, and then a tetrahydrofuran solution containing 9.9 g (40 mmol) of the compound (1-D) was added dropwise. Then, to the mixture, 50 ml of a tetrahydrofuran solution containing 0.1 g of N,N-dimethylaminopyridine was added dropwise, followed by stirring under ice-cooling for one hour, then raising to the room temperature, and further stirring for 6 hours. And then, ethyl acetate and water were added to the mixture, to separate an organic phase. The organic phase was washed with water, 1-N aqueous hydrochloric acid and water, in this order, and then dried over magnesium sulfate, and then the solvents were distilled off under reduced pressure. The resultant was purified by a silica gel column chromatography using a methylene chloride/methanol mixture solvent as an eluting solution, thereby obtaining 26.7 g of the exemplified compound (49) (74 mol % in yield).

Example 8

Synthesis of Exemplified Compound (129)

The exemplified compound (129) was synthesized, according to the following scheme.

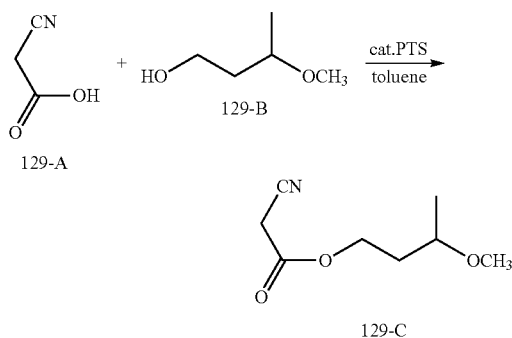

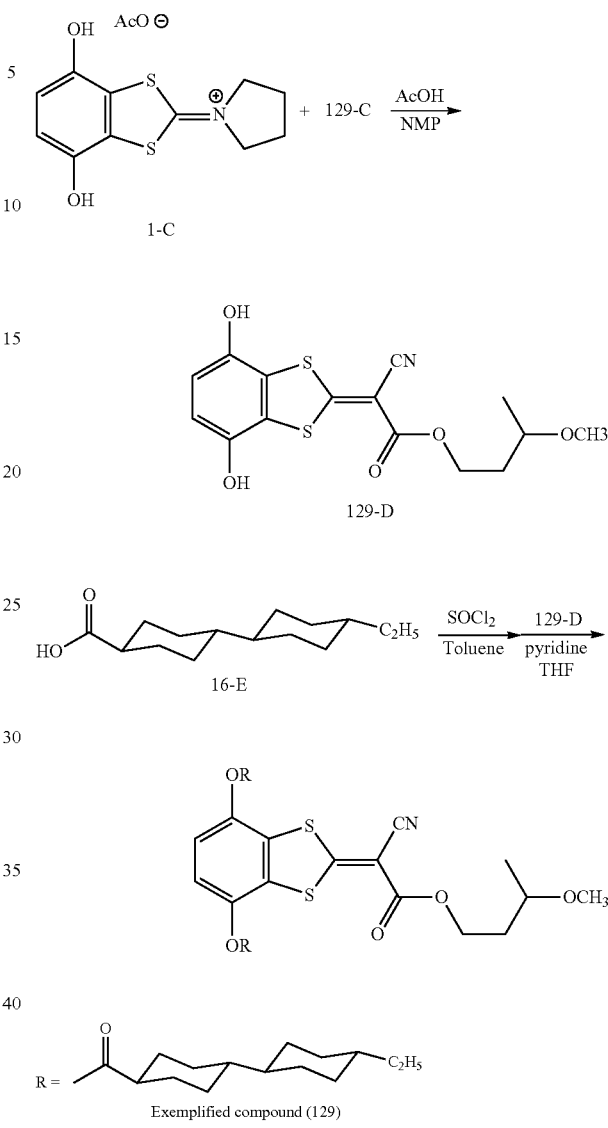

To a 1.4-liter toluene solution containing 377 g (4.43 mol) of the compound (129-A) and 460 g (4.43 mol) of 2-methoxybutanol (129-B), was added 2.7 g of paratoluenesulfonic acid (PTS), and the mixture was then dehydrated by refluxing with a Dean-Stark. After completion of the reaction, 1 L of toluene was distilled off. The temperature of the reaction system was cooled to room temperature and ethyl acetate and water were then added, to separate an organic layer. The organic layer was washed with water, a saturated sodium hydrogencarbonate solution, a 1-N hydrochloric acid solution, and water, in the stated order. The organic layer was dried over magnesium sulfate and the solvents were then distilled off under reduced pressure, thereby obtaining 651 g of a crude product of the compound (129-C).

To a 800-ml N-methylpyrrolidone (NMP) solution containing 101 g (0.322 mol) of the compound (1-C), was added 66.2 (0.387 mol) of the crude product of the compound (129-C), and the mixture was then stirred for 2 hours at an inner temperature of 120° C. After cooling down, the reaction solution was flown into 3 L of an ice-cold 1-N hydrochloric acid. The obtained solid was filtrated and then dried. The solid was dispersed in an acetone/hexane mixed solvent and then filtration was repeated two times. The solid was recrystallized with acetic acid (AcOH), filtrated, and dried, thereby obtaining 112 g of the compound (129-D) (98 mol % in yield).

To a 500-ml toluene solution containing 134 g (562 mmol) of the compound (16-E) (manufactured by Yantai valiant Fine Chem.), was added 62.4 ml (855 mmol) of thionyl chloride, and the mixture was then subjected to reflux under heat. The consumption of the carboxylic acid was confirmed by TLC and the solvents were then distilled off. The product itself was added dropwise into a 700-ml tetrahydrofuran solution containing 83 g (235 mmol) of the compound (129-D) and 46.1 ml (570 mmol) of pyridine under ice-cooling. After completion of the reaction, the resultant was flown into 5 L of methanol and then subjected to a filtration. The obtained solid was dissolved in methylene chloride. Subsequently, purification was carried out with a silica-gel column chromatography using methylene chloride as an eluting solution, thereby obtaining 164 g of the exemplified compound (129) (88 mol % in yield).

Example 9

Synthesis of Exemplified Compound (124)

According to the following scheme, the exemplified compound (124) was synthesized in the same manner as in Example 8, except that 2-methyl-2,4-butanediol (124-B) was used instead of 2-methoxybutanol (129-B).

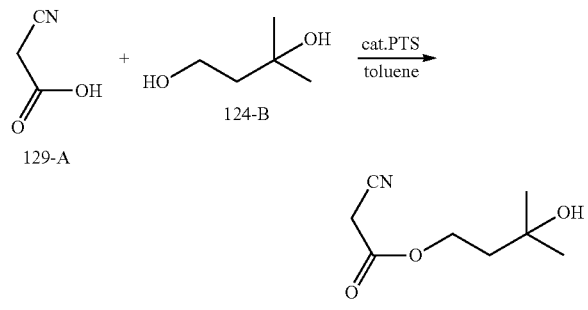

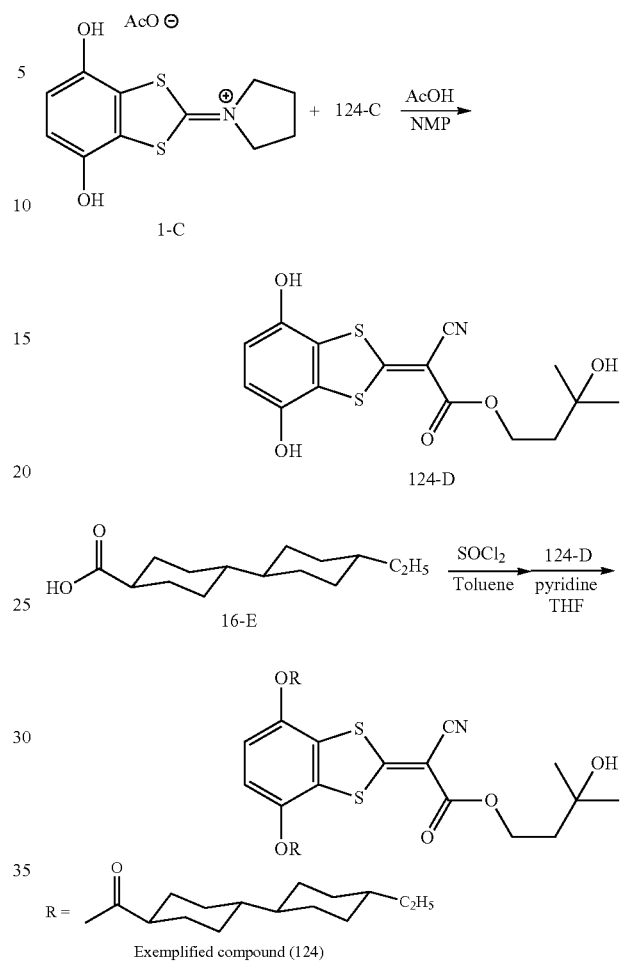

Example 10

Preparation of Mixture of Exemplified Compounds (140), (141) and (142)

According to the following scheme, a mixture of the exemplified compounds (140), (141) and (142) was prepared.

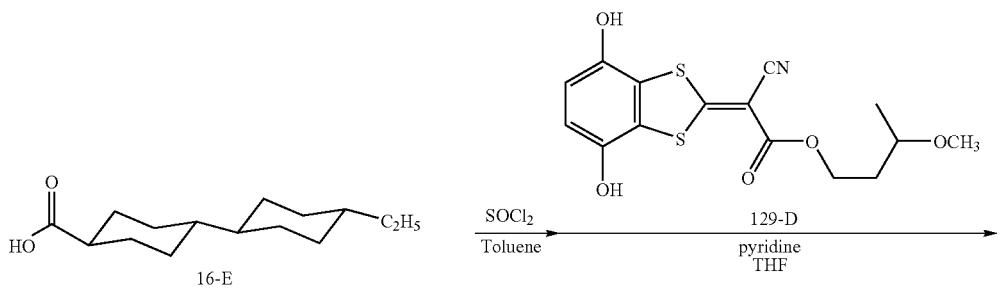

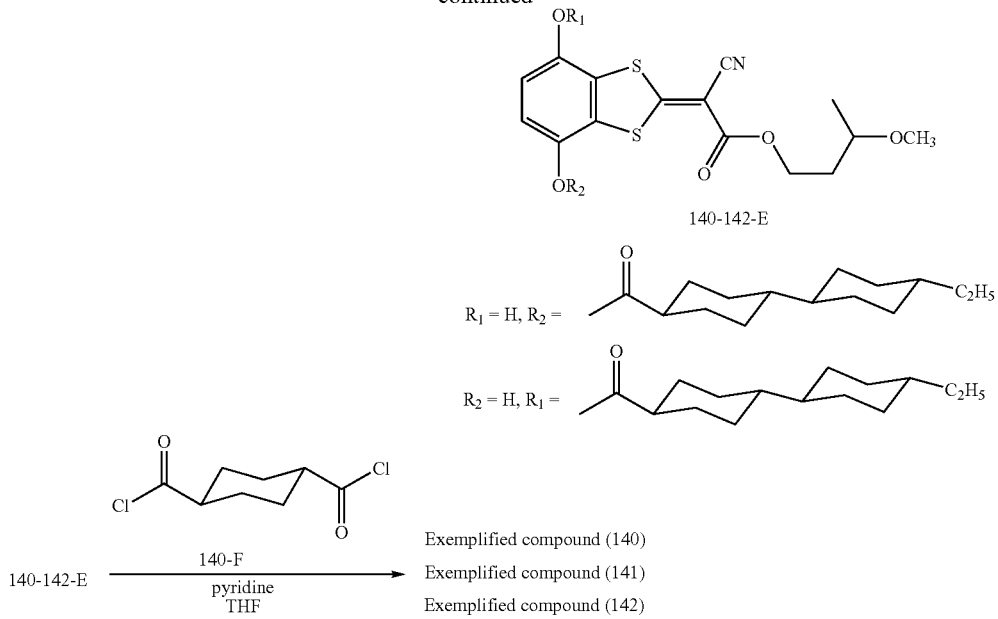

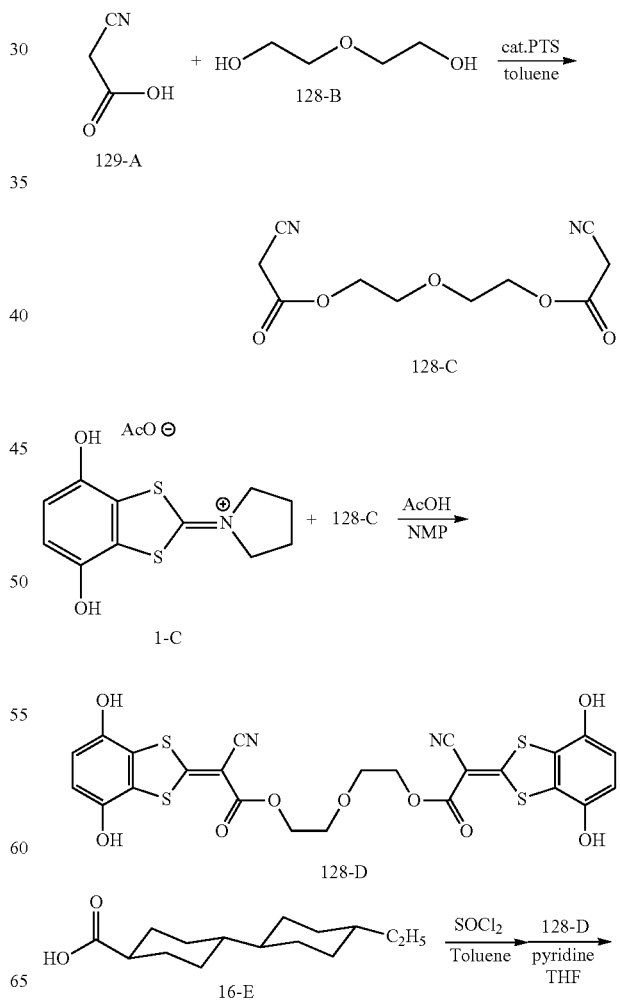

To a 50-ml toluene solution containing 13.3 g (56 mmol) of the compound (16-E) (manufactured by Yantai valiant Fine Chem.), was added 6.1 ml (84 mmol) of thionyl chloride, and the mixture was then subjected to reflux under heat. The consumption of the carboxylic acid was confirmed by TLC and the solvents were then distilled off. The product itself was added dropwise into a 200-ml tetrahydrofuran solution containing 20 g (56.6 mmol) of the compound (129-D) and 4.5 ml (56 mmol) of pyridine under ice-cooling. After completion of the reaction, ethyl acetate and water were added to separate an organic layer, and the organic layer was washed with water, a 1-N hydrochloric acid solution, and water, in the stated order. The organic layer was dried over magnesium sulfate and the solvents were then distilled off under reduced pressure. The resultant was purified with a silica gel column chromatography using an ethyl acetate/hexane mixed solvent as an eluting solution, thereby obtaining 9.6 g of the compounds (140-142-E) (30 mol % in yield).

To a 100-ml tetrahydrofuran solution containing 5 g (8.73 mmol) of the compounds (140-142-E) and 0.7 ml (8.73 mmol) of pyridine, was added dropwise, under ice-cooling, a 10-ml tetrahydrofuran solution containing 0.8 g (3.8 mmol) of the compound (144-F) synthesized by the method described in Synthesis (1991); p 441. After completion of the reaction, the reaction solution was flown into methanol and then the mixture was subjected to a filtration. The obtained solid was crystallized in ethyl acetate, thereby obtaining 3.4 g of a mixture of the exemplified compounds (140), (141) and (142) (70 mol % in yield).

Example 11

Synthesis of Exemplified Compound (128)

The exemplified compound (128) was synthesized, according to the following scheme.

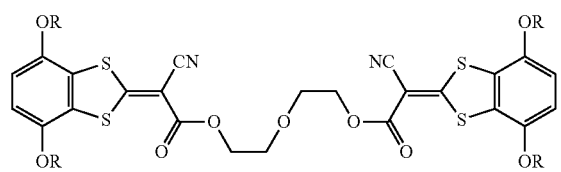

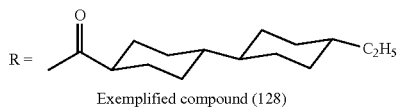

Exemplified compound (128)

To a 300-ml toluene solution containing 93.6 g (1.1 mol) of the compound (129-A) and 53 g (0.5 mol) of the compound (128-B), was added 2.0 g of paratoluenesulfonic acid, and the mixture was then dehydrated by refluxing with a Dean-Stark. After completion of the reaction, 200 mL of toluene was distilled off. The temperature of the reaction system was cooled to room temperature and ethyl acetate and water were then added, to separate an organic layer. The organic layer was washed with water, a saturated sodium hydrogen carbonate solution, a 1-N hydrochloric acid solution, and water, in the stated order. The organic layer was dried over magnesium sulfate and the solvents were then distilled off under reduced pressure, thereby obtaining 86.2 g of a crude product of the compound (128-C) (72 mol % in yield).

To a 350-ml N-methylpyrrolidone solution containing 35 g (112 mmol) of the compound (1-C) and 6.4 ml of acetic acid, was added 12.2 (51 mmol) of the crude product of the compound (128-C), and the mixture was then stirred for 5 hours at an inner temperature of 100° C. After cooling, the remaining solid was removed by Celite and the obtained filtrate was then flown into 1.5 L of water. The obtained solid was collected by filtration and then dried. Ethyl acetate was added to the solid and then the mixture was heated to boiling. After leaving as it was to cool down, the solid was filtrated and dried, thereby obtaining 22.8 g of the compound (128-D) (74 mol % in yield).

To a 300-ml toluene solution containing 34.7 g (146 mmol) of the compound (16-E) (manufactured by Yantai valiant Fine Chem.), was added 16 ml (220 mmol) of thionyl chloride, and the mixture was then subjected to reflux under heat. The consumption of the carboxylic acid was confirmed by TLC and the solvents were then distilled off. The product itself was added dropwise into a 200-ml tetrahydrofuran solution containing 20 g (33 mmol) of the compound (128-D) and 11.5 ml (146 mmol) of pyridine under ice-cooling. After completion of the reaction, the resultant was flown into 1.5 L of methanol and then subjected to a filtration. The obtained solid was dissolved in methylene chloride. Subsequently, purification was carried out with a silica-gel column chromatography using methylene chloride as an eluting solution, thereby obtaining 26 g of the exemplified compound (128) (53 mol % in yield).

Example 12

Preparation of Mixture of Exemplified Compounds (100) and (116)

According to the following scheme, a mixture of the exemplified compounds (100) and (116) was prepared.

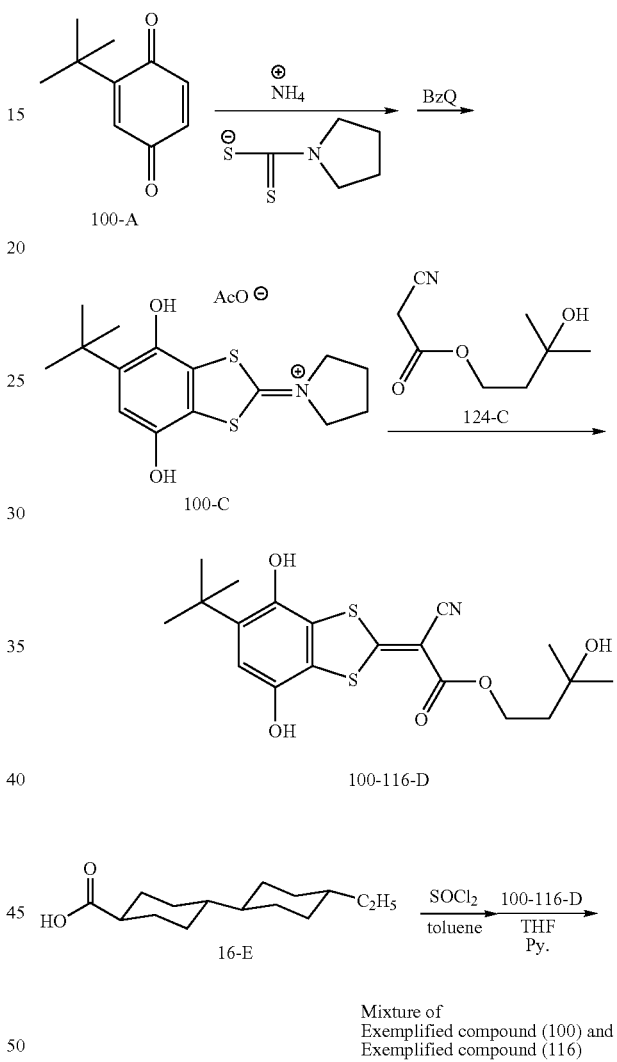

Mixture of
Exemplified compound (100) and
Exemplified compound (116)

To a 600-ml dimethylformamide solution containing 100 g (0.61 mmol) of pyrrolidine-dithiocarbamate ammonium salt, was added an acetic acid solution containing 100 g (0.61 mol) of the compound (100-A) was added dropwise at an external temperature of 5° C. After completion of the dropping, the mixture was heated to room temperature to complete the reaction. After that, 66 g (0.61 mol) of benzoquinone (BzQ) was added thereto in fractional amounts, and the mixture was then additionally stirred for 2 hours at room temperature. After completion of the reaction, the obtained solid was collected by filtration and then rinsed with acetic acid and acetone. After drying the resultant, 155 g of the compound (100-C) was obtained (69 mol % in yield).

To a 400-ml N-methylpyrrolidone solution containing 47 g (127 mmol) of the compound (100-C), was added 28.3 g (165 mmol) of the crude product of the compound (124-C) obtained in Example 9, and the mixture was then stirred for 3 hours at an inner temperature of 100° C. After completion of the reaction, the mixture was cooled and the remaining solid was then removed by Celite, followed by separating an organic layer with addition of ethyl acetate and water. The organic layer was washed with water, a 1-N hydrochloric acid solution, and water, in the stated order. The organic layer was dried over magnesium sulfate and the solvents were then distilled off under reduced pressure. The resultant was purified with a silica gel column chromatography using an ethyl acetate/hexane mixed solvent as an eluting solution, thereby obtaining 40 g of the compounds (100-116-D) (77 mol % in yield).

To a 240-ml toluene solution containing 55.9 g (235 mmol) of the compound (16-E) (manufactured by Yantai valiant Fine Chem.), was added 25.8 ml (353 mmol) of thionyl chloride, and the mixture was then subjected to reflux under heat. The consumption of the carboxylic acid was confirmed by TLC and the solvents were then distilled off. The product itself was added dropwise into a 430-ml tetrahydrofuran solution containing 40 g (97.7 mmol) of the compounds (100-116-D) and 18.8 ml (232 mmol) of pyridine (Py.) under ice-cooling. After completion of the reaction, ethyl acetate and water were added to separate an organic layer, and the organic layer was washed with water, a 1-N hydrochloric acid solution, and water, in the stated order. The organic layer was dried over magnesium sulfate and the solvents were then distilled off under reduced pressure. Crystallization was carried out using an ethyl acetate/hexane mixed solvent, thereby obtaining 73 g of a mixture of the exemplified compounds (100) and (116) (88 mol % in yield).

Example 13

Preparation of Mixture of Exemplified Compounds (124), (122) and (133)

According to the following scheme, a mixture of the exemplified compounds (124), (122) and (133) was prepared in the same similar as in Example 9, except that the compound (16-E) was replaced with an equimolar mixture of the compounds (16-E) and (16'-E).

Example 14

Preparation 1 of Cellulose Acetate Film

The following components of a cellulose acetate solution composition were charged into a mixing tank, followed by stirring under heating, to dissolve the components each other. Thus, a cellulose acetate solution was prepared.

| (Composition of a cellulose acetate solution) | |
|---|---|
| Cellulose acetate (acetylation degree 60.9%) | 100 mass parts |
| Triphenyl phosphate (plasticizer) | 7.8 mass parts |
| Biphenyl diphenyl phosphate (plasticizer) | 3.9 mass parts |
| Methylene chloride (first solvent) | 318 mass parts |
| Methanol (second solvent) | 47 mass parts |

To another mixing tank, the exemplified compound (16), (20), (124) or (129) or the compound for comparison (1), 87 mass parts of methylene chloride, and 13 mass parts of methanol were charged, followed by stirring under heating, to prepare a retardation controlling agent solution, respectively.

Then, 36 mass parts of the above-prepared retardation controlling agent solution was mixed with 474 mass parts of the cellulose acetate solution, and the resultant mixture was thoroughly stirred, to prepare a dope.

The exemplified compounds and the compound for comparison each were added in an amount in terms of mass parts, as shown in Table 1, to 100 mass parts of the cellulose acetate, to prepare the retardation controlling agent solutions.

The thus-obtained dope was cast, using a band casting machine. The resultant film in which the residual solvent amount was 15 mass %, was laterally oriented by free-end uniaxial stretching, under the conditions of 150° C., at an orientation ratio of 15%, to prepare a cellulose acetate film (thickness: 92 μm).

With respect to the thus-produced cellulose acetate films, the Re retardation values at wavelengths of 450 nm, 550 nm and 630 nm were measured by making light of each wavelength incident in the direction of the normal of the film using KOBRA 21ADH (trade name, manufactured by Oji Scientific Instruments Co., Ltd.). The results are shown in Table 1. Note that, the sample No. 1 in Table 1 was a cellulose acetate film produced in a manner similar to the others, except that no retardation-controlling agent solution was added.

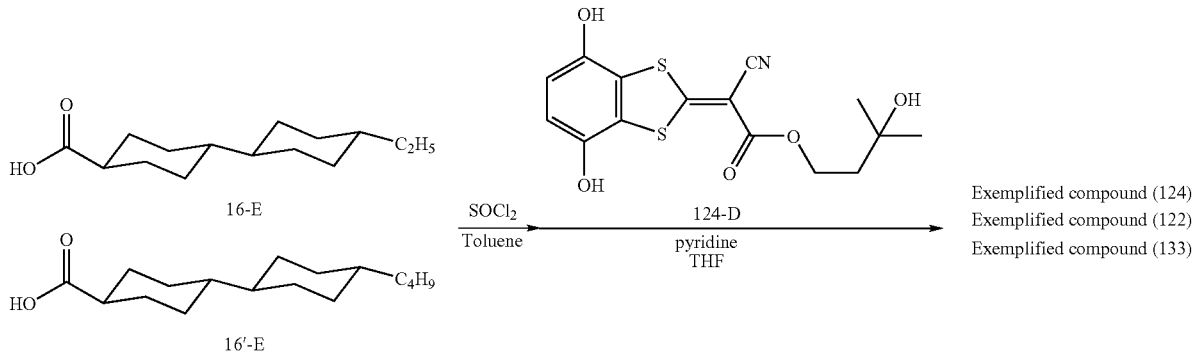

TABLE 1

| No. | Additive | Amount to be added (mass parts) | Re(450) (nm) | Re(550) (nm) | Re(630) (nm) | $\Delta n(450)/\Delta n(550)$ | $\Delta n(630)/\Delta n(550)$ |
|---|---|---|---|---|---|---|---|
| 1 | None | 0 | 0.8 | 7.7 | 11.7 | 0.10 | 1.52 |
| 2 | Exemplified compound (16) | 2.0 | 12.6 | 24.9 | 29.9 | 0.51 | 1.20 |
| 3 | Exemplified compound (16) | 3.5 | 38.9 | 56.9 | 63.8 | 0.68 | 1.12 |
| 4 | Exemplified compound (16) | 4.0 | 42.8 | 62.1 | 68.3 | 0.69 | 1.10 |
| 5 | Exemplified compound (20) | 3.5 | 40.4 | 56.8 | 63.4 | 0.71 | 1.12 |
| 6 | Exemplified compound (124) | 2.0 | 43.0 | 65.2 | 75.6 | 0.66 | 1.16 |
| 7 | Exemplified compound (124) | 5.0 | 62.7 | 91.2 | 104.0 | 0.69 | 1.14 |
| 8 | Exemplified compound (129) | 2.0 | 44.1 | 64.8 | 74.5 | 0.68 | 1.15 |
| 9 | Exemplified compound (129) | 5.0 | 61.0 | 88.4 | 99.9 | 0.69 | 1.13 |
| 10 | Compound for comparison (1) | 3.5 | 63.8 | 63.4 | 64.9 | 1.01 | 1.02 |
| 11 | Compound for comparison (1) | 5.0 | 75.1 | 69.5 | 67.1 | 1.08 | 0.97 |

Compound for Comparison (1)

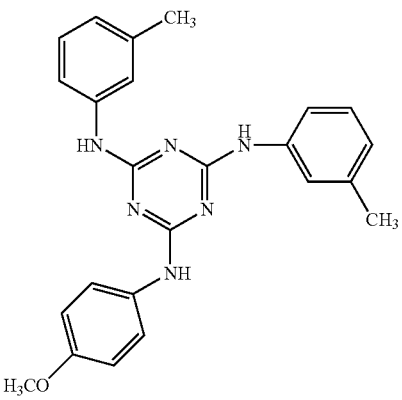

As is evident from Table 1, it was found that the sample No. 1 in which the retardation-controlling agent solution was not used had an extremely small Re value and thus the ability of Re expression by stretching was not obtained. In addition, it was also found that the sample No. 1 did not satisfy the above expressions (1) and (2), thereby resulting in poor wavelength dispersion of birefringence Δn. Further, it was found that though the sample Nos. 10 and 11 added with the compound for comparison (1) showed large Re values at the respective wavelengths, they did not satisfy the above expressions (1) and (2), thereby resulting in poor wavelength dispersion of birefringence Δn.

In contrast, it was found that the samples according to the present invention (sample Nos. 2 to 9) had large Re values at the respective wavelengths and satisfied the above expressions (1) and (2), thereby resulting in good wavelength dispersion of birefringence Δn.

Comparing the sample No. 10, in which the compound for comparison (1) was added, with the sample Nos. 3 and 5, in which the exemplified compound (16) or (20) was added in parts by mass equal to that of the compound for comparison (1) in the sample No. 10, it was found that though there was no large difference in values of Re(550 nm), the sample Nos. 3 and 5 satisfied the expressions (1) and (2) but the sample No. 10 did not satisfy them. In addition, comparing the sample No. 11, in which the compound for comparison (1) was added, with the sample Nos. 7 and 9, in which the exemplified compound (124) or (129) was added in parts by mass equal to that of the compound for comparison (1) in the sample No. 11, it was found that though they each had a large Re(550 nm) value, the sample Nos. 7 and 9 satisfied the expressions (1) and (2) but the sample No. 11 did not satisfy these expressions.

Further, comparing the sample Nos. 2, 3, and 4 having different amounts of the exemplified compound (16) with each other, it was found that the more the amount added increased the more the Re value increased.

Example 15

Preparation 2 of Cellulose Acetate Film

The dope prepared in Example 14 was cast, using a band casting machine. The resultant film in which the residual solvent amount was 15 mass %, was laterally oriented by fixed-end uniaxial stretching, under the conditions of 150° C., at an orientation ratio of 15%, to prepare a cellulose acetate film (thickness: 80 μm).

With respect to the thus-produced cellulose acetate films, the Re retardation values at wavelengths of 450 nm, 550 nm and 630 nm were measured by making light of each wavelength incident in the direction of the normal of the film using KOBRA 21ADH (trade name, manufactured by Oji Scientific Instruments Co., Ltd.). The results are shown in Table 2. Note that, the sample No. 21 in Table 2 was a cellulose acetate film produced in a manner similar to the others, except that no retardation-controlling agent solution was added.

TABLE 2

| No. | Additive | Amount to be added (mass parts) | Re(450) (nm) | Re(550) (nm) | Re(630) (nm) | $\Delta n(450)/\Delta n(550)$ | $\Delta n(630)/\Delta n(550)$ |
|---|---|---|---|---|---|---|---|
| 21 | None | 0 | −6.4 | −0.5 | 2.0 | 12.8 | −4 |
| 22 | Exemplified compound (124) | 3.3 | 27.1 | 39.8 | 44.6 | 0.68 | 1.12 |
| 23 | Exemplified compound (124) | 6.0 | 49.2 | 72.3 | 81.7 | 0.68 | 1.13 |
| 24 | Exemplified compound (129) | 3.3 | 25.6 | 37.2 | 41.0 | 0.69 | 1.10 |
| 25 | Exemplified compound (129) | 6.0 | 51.2 | 74.2 | 83.8 | 0.69 | 1.13 |
| 26 | Compound for comparison (1) | 3.3 | 33.2 | 34.7 | 35.6 | 0.96 | 1.03 |
| 27 | Compound for comparison (1) | 6.0 | 66.1 | 61.2 | 59.7 | 1.08 | 0.98 |

Just as in the case with Example 14, as is evident from the results shown in Table 2, it was found that the sample No. 21, in which a retardation-controlling agent solution was not used, and the sample Nos. 26 and 27, in which the compound for comparison (1) was used, did not satisfy the expressions (1) and (2) and showed poor wavelength dispersion of birefringence Δn. In contrast, each of the samples according to the present invention (sample Nos. 22 to 25) had large Re values, respectively, and also satisfied the expressions (1) and (2), thereby resulting in excellent wavelength dispersion of birefringence Δn.

Example 16

Preparation of Polarizing Plate

A polarizing film was prepared by adsorbing iodine on a stretched polyvinyl alcohol film.

The cellulose acylate film (Sample No. 4 in Table 1) prepared in Example 14 was attached on one side of the polarizing film using a polyvinyl alcohol-based adhesive agent. A saponification treatment was carried out under the following conditions.

A 1.5-mol/liter aqueous sodium hydroxide solution was prepared and then kept warm at 55° C. A 0.01-mol/l aqueous diluted sulfuric acid solution was prepared and kept warm at 35° C. The prepared cellulose acylate film was dipped in the aqueous sodium hydroxide solution for 2 minutes, and then dipped in water to sufficiently wash out the aqueous sodium hydroxide solution. Subsequently, after dipping in the above aqueous diluted sulfuric solution for 1 minute, the film was dipped in water to sufficiently wash out the diluted sulfuric solution. Finally, the sample was sufficiently dried at 120° C.

A commercially available cellulose triacylate film (trade name: Fujitack TD80UF, manufactured by Fuji Photo Film Co., Ltd.) was subjected to a saponification treatment and then bonded on the opposite side of the polarizer using a polyvinyl alcohol-based adhesive agent, followed by drying at 70° C. for 10 minutes or more.

The transmission axis of the polarizing film and the slow phase axis of the cellulose acylate film prepared as described above were arranged in parallel. The transmission axis of the polarizing film and the slow phase axis of the commercially available cellulose triacylate film were perpendicularly arranged.

(Production of Liquid Crystal Cell)

A liquid crystal cell was manufactured in the following manner: A cell gap between substrates was set to 3.6 μm, and a liquid crystal material (trade name: MLC 6608, manufactured by Merck Co., Ltd.) having negative dielectric anisotropy was injected dropwise into and sealed in the gap between these substrates, to form a liquid crystal layer between these substrates. The retardation of the liquid crystal layer (namely, the product Δn·d of the thickness d (μm) of the liquid crystal layer and the refractive index anisotropy Δn) was set to 300 nm. The liquid crystal material was oriented such that it was vertically oriented.

(Deposing on VA Panel)

A commercially available polarizing plate (trade name: HLC2-5618, manufactured by Sanritz Corporation) was used, as the upper-side polarizing plate (observer side) of the above liquid crystal display which had the vertical orientation type liquid crystal cell. As the lower-side polarizing plate (back light side), a polarizing plate provided with any one of the films (sample Nos. 4, 6, and 8 in Table 1) prepared in Example 14 and the films (sample Nos. 23 and 25 in Table 2) prepared in Example 15 was disposed so that the cellulose acylate film was located on the liquid crystal cell side. The upper polarizing plate and the lower polarizing plate were laminated to the liquid crystal cell through an adhesive. These polarizing plates were disposed in cross nicol state such that the transmission axis of the upper polarizing plate was arranged in a vertical direction and the transmission axis of the lower polarizing plate was arranged in a horizontal direction.

A rectangular wave voltage of 55 Hz was applied to the liquid crystal cell. The liquid crystal cell was put in a normally black mode (white display 5 V, and black display 0 V). A black display at a view angle under the conditions of an orientation angle of 45 degrees and a polar angle of 60 degrees; and a color shift between under the conditions, in which an orientation angle was 45 degrees and an polar angle was 60 degrees, and under the conditions, in which an orientation angle was 180 degrees and polar angle was 60 degrees, were observed.

As a result of observing the prepared liquid crystal displays, it was confirmed that a liquid crystal display using the film of the present invention was able to realize a neutral black display in any front direction and view angle direction.

Example 17

Evaluation of Reverse Dispersion Liquid Crystal Compound

The exemplified compound (16) of the present invention was injected into a wedge-shaped liquid crystal cell (trade name: N-Wedge NLCD-057, manufactured by NIPPON DENKI Co., Ltd.) at 200° C. and Δn values were then measured at 450 nm, 550 nm, and 650 nm at 180° C., respectively. As a result, the resultant Δn values were as follows: Δn(450 nm)=0.037; Δn(550 nm)=0.046; and Δn(650 nm)=0.051. In other words, it was found that: Δn(450 nm)/Δn(550 nm)=0.80; and Δn(650 mm)/Δn(550 nm)=1.11. The results were shown in Table 3 below.

For the exemplified compound (20) of the present invention, Δn values were measured at 450 mm, 550 nm, and 650 nm, respectively, in the same manner as described above. As a result, the resultant Δn values were as follows: Δn(450 nm)=0.036; Δn(550 nm)=0.044; and Δn(650 nm)=0.051. In other words, it was found that: Δn(450 nm)/Δn (550 nm)=0.82; and Δn(650 nm)/Δn(550 nm)=1.16. The results were shown in Table 3 below.

With respect to the exemplified compounds (4), (28), (124), (128) and (169), the values of Δn(450 nm), Δn (550 nm) and Δn(650 nm) were measured in the same manner as in the exemplified compound (16). The results were shown in Table 3 below.

(Comparison with Typical Rod-Shaped Liquid Crystal Compound)

A rod-shaped liquid crystal compound (compound for comparison (A)), which could be synthesized by a routine method, was injected into a wedge-shaped liquid crystal cell (trade name: N-Wedge NLCD-057, manufactured by NIPPON DENKI Co., Ltd.) at 210° C. and Δn values were then determined at 450 nm, 550 μm, and 650 nm at 150° C., respectively. As a result, the resultant Δn values were as follows: Δn(450 nm)=0.126; Δn(550 nm)=0.111; and Δn(650 nm)=0.108. In other words, it was found that: Δn(450 nm) Δn(550 nm)=1.14; and Δn(650 nm)/Δn(550 nm)=0.97. The results were shown in Table 3 below.

TABLE 3

| No. | Liquid crystal compound | Δn(450) | Δn(550) | Δn(650) | Δn(450)/Δn(550) | Δn(650)/Δn(550) |
|---|---|---|---|---|---|---|
| 31 | Exemplified compound (16) | 0.037 | 0.046 | 0.051 | 0.80 | 1.11 |
| 32 | Exemplified compound (20) | 0.036 | 0.044 | 0.051 | 0.82 | 1.16 |
| 33 | Exemplified compound (4) | 0.041 | 0.061 | 0.065 | 0.68 | 1.08 |
| 34 | Exemplified compound (28) | 0.30 | 0.048 | 0.052 | 0.63 | 1.08 |
| 35 | Exemplified compound (124) | 0.036 | 0.047 | 0.050 | 0.77 | 1.06 |
| 36 | Exemplified compound (128) | 0.036 | 0.052 | 0.054 | 0.71 | 1.04 |
| 37 | Exemplified compound (169) | 0.026 | 0.037 | 0.039 | 0.70 | 1.07 |
| 38 | Compound for comparison (A) | 0.126 | 0.111 | 0.108 | 1.14 | 0.97 |

Compound for Comparison (A)

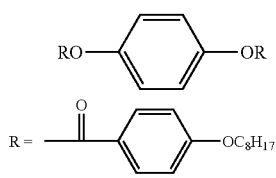

As is evident from Table 3, the wavelength dispersion of the typical rod-shaped liquid crystal compound (compound for comparison (A)) was normal dispersion that tended downward (the slope of Δn when smaller wavelengths were on the left side and larger wavelengths were on the right side). In contrast, it was found that the exemplified compounds (4), (16), (20), (28), (124), (128), and (169) of the present invention were reverse dispersion liquid crystal compounds that tended upward, respectively.

Please note that in Example 17, Δn(450 nm), Δn(550 nm) and Δn(650 nm) each means birefringent of the liquid crystal compound at a wavelength of 450 nm, 550 nm and 650 nm, respectively.

Example 18

Liquid Crystal Composition Containing Liquid Crystal Compound Having Normal Dispersion for Wavelength Dispersion Δn The liquid crystal compound (20) of the present invention and the typical liquid crystal compound (the above compound for comparison (A)) were once dissolved in dichloroethane and the dichloroethane was then removed under reduced pressure, thereby obtaining a liquid crystal composition.

The liquid crystal composition was subjected to the same procedures as described above to determine Δn values at 450 nm, 550 nm, and 650 nm in nematic phase, respectively. As a result, the composition was found to be a reverse dispersion liquid crystal composition that tends upward. In other words, by mixing the liquid crystal compound where the wavelength dispersion Δn is reverse dispersion and a liquid crystal compound where the wavelength dispersion is normal dispersion, it becomes possible to obtain a liquid crystal composition which is intermediate in wavelength dispersion between them.

INDUSTRIAL APPLICABILITY

The compound of the present invention can provide reverse wavelength dispersion to a film. Therefore, the compound of the present invention can be suitably used for an optical film. Also, the phase difference plate of the present invention has reverse wavelength dispersion of birefringence. Therefore, the phase difference plate of the present invention can be suitably used as a broadband λ/4 plate. Further, the phase difference plate of the present invention can be suitably used for a polarizing plate and a liquid crystal display.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2006-030004 filed in Japan on Feb. 7, 2006, and Patent Application No. 2006-263335 filed in Japan on Sep. 27, 2006, each of which is entirely herein incorporated by reference.

The invention claimed is:

1. An optical film, which has been subjected to an orientation treatment, comprising at least one low-molecular weight compound, wherein a birefringence Δn(550 nm) is larger than zero (0) in an orientation direction, wherein the optical film satisfies the following expressions (1) and (2):

$$0.5 < \Delta n(450 \text{ nm})/\Delta n(550 \text{ nm}) < 1.0; \text{ and} \qquad \text{Expression (1)}$$

$$1.05 < \Delta n(630 \text{ nm})/\Delta n(550 \text{ nm}) < 1.5, \text{ and} \qquad \text{Expression (2)}$$

wherein the low-molecular weight compound is a compound represented by formula (I):

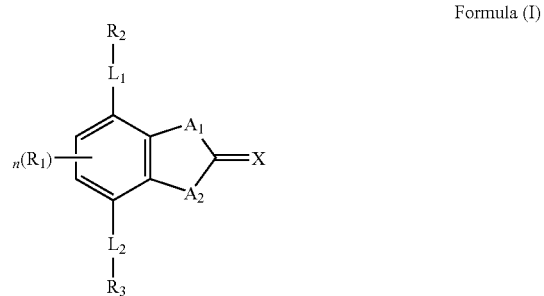

Formula (I)

wherein $L_1$ and $L_2$ each independently represents a group selected from the group consisting of

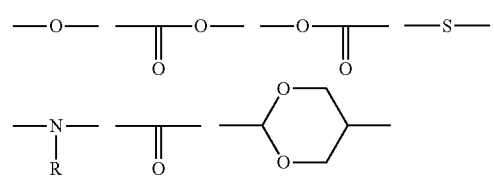

$A_1$ and $A_2$ each independently represent a group selected from the group consisting of —O—, —NR— (in which R represents a hydrogen atom or a substituent), —S—, and —CO—; $R_1$ represents a substituent; $R_2$ and $R_3$ each independently represent a benzene ring having a substituted or unsubstituted benzoyloxy group at the 4-position, a benzene ring having a substituted or unsubstituted cyclohexyl group at the 4-position, a cyclohexane ring having a substituted or unsubstituted benzene ring at the 4-position, or a cyclohexane ring having a substituted or unsubstituted cyclohexyl group at the 4-position; X represents a nonmetallic atom belonging to any of Groups 14 to 16, and may have a hydrogen atom or a substituent; and n represents an integer of 0 to 2.

2. The optical film according to claim 1, wherein the low-molecular weight compound has a molecular weight of 100 to 1,500.

3. The optical film according to claim 1, wherein the low-molecular weight compound is contained in an amount of 0.1 to 50 mass % with respect to the mass of the film.

4. The optical film according to claim 1, wherein the optical film satisfies the following expressions (1') and (2'):

$0.7 < \Delta n(450 \text{ nm})/\Delta n(550 \text{ nm}) < 0.9$;   Expression (1')

$1.05 < \Delta n(630 \text{ nm})/\Delta n(550 \text{ nm}) < 1.25$.   Expression (2')

5. The optical film according to claim 1, wherein the low-molecular weight compound is a compound represented by formula (II):

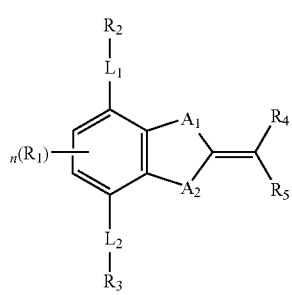

Formula (II)

wherein $L_1$ and $L_2$ each independently represent a group selected from the group consisting of

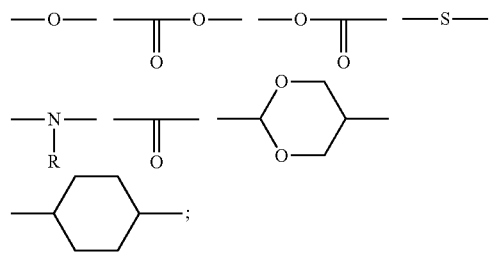

$A_1$ and $A_2$ each independently represent a group selected from the group consisting of —O—, —NR— (in which R represents a hydrogen atom or a substituent), —S—, and —CO—; $R_1$, $R_4$ and $R_5$ each independently represent a substituent; $R_2$ and $R_3$ each independently represent a benzene ring having a substituted or unsubstituted benzoyloxy group at the 4-position, a benzene ring having a substituted or unsubstituted cyclohexyl group at the 4-position, a cyclohexane ring having a substituted or unsubstituted benzene ring at the 4-position, or a cyclohexane ring having a substituted or unsubstituted cyclohexyl group at the 4-position; and n represents an integer of 0 to 2.

6. The optical film according to claim 1, wherein the compound represented by formula (I) is a compound showing liquid crystallinity.

7. The optical film according to claim 1, which is formed of a polymer composition comprising a cellulose compound as a main component.

8. The optical film according to claim 7, wherein the cellulose compound is a cellulose acylate.

9. A phase difference plate, comprising the optical film according to claim 1.

10. A polarizing plate, comprising the phase difference plate according to claim 9.

11. A liquid crystal display, comprising the phase difference plate according to claim 9.

12. The optical film according to claim 5, wherein the compound represented by formula (II) is a compound showing liquid crystallinity.

13. A liquid crystal display, comprising the polarizing plate according to claim 10.

14. The optical film according to claim 5, wherein $R_4$ and $R_5$ each independently represent an electron-withdrawing substituent having a Hammett substituent constant $\sigma_p$ of more than zero.

* * * * *